(12) United States Patent
Shuhendler et al.

(10) Patent No.: US 11,696,960 B2
(45) Date of Patent: Jul. 11, 2023

(54) METHODS AND COMPOUNDS FOR DETECTION AND BINDING OF ALDEHYDES

(71) Applicant: UNIVERSITY OF OTTAWA, Ottawa (CA)

(72) Inventors: Adam Shuhendler, Ottawa (CA); Mojmir Suchy, Ottawa (CA); Trina Dang, Mississauga (CA)

(73) Assignee: UNIVERSITY OF OTTAWA, Ottawa (CA)

( * ) Notice: Subject to any disclaimer, the term of this patent is extended or adjusted under 35 U.S.C. 154(b) by 498 days.

(21) Appl. No.: 16/482,492

(22) PCT Filed: Feb. 5, 2018

(86) PCT No.: PCT/CA2018/050125
§ 371 (c)(1),
(2) Date: Jul. 31, 2019

(87) PCT Pub. No.: WO2018/141069
PCT Pub. Date: Aug. 9, 2018

(65) Prior Publication Data
US 2020/0376144 A1    Dec. 3, 2020

Related U.S. Application Data

(60) Provisional application No. 62/455,132, filed on Feb. 6, 2017.

(51) Int. Cl.
| A61K 49/10 | (2006.01) |
| A61K 51/04 | (2006.01) |
| C07C 251/76 | (2006.01) |
| C07C 309/46 | (2006.01) |

(52) U.S. Cl.
CPC .............. *A61K 49/10* (2013.01); *A61K 51/04* (2013.01); *C07C 251/76* (2013.01); *C07C 309/46* (2013.01)

(58) Field of Classification Search
CPC ...... A61K 49/10; A61K 51/04; C07C 251/76; C07C 309/49
USPC ......................................................... 424/9.3
See application file for complete search history.

(56) References Cited

U.S. PATENT DOCUMENTS

| 6,359,111 B1 | 3/2002 | Meyer et al. |
| 8,772,487 B2 | 7/2014 | Chen et al. |
| 2010/0291547 A1* | 11/2010 | Chen ................. C07F 9/65522 436/86 |
| 2014/0294772 A1 | 10/2014 | Levy et al. |
| 2016/0082133 A1 | 3/2016 | Gilad et al. |

FOREIGN PATENT DOCUMENTS

| WO | 2005030744 A1 | 4/2005 |
| WO | WO-2015085005 A1 * | 6/2015 ........... A61K 49/103 |

OTHER PUBLICATIONS

Kool et al. Org. Lett. 2014, 16, 1454-1457. (Year: 2014).*
Matveychuk et al. Bull Clin. Psychopharmacol. 2011, 21, 277-288. (Year: 2011).*
Hlozek et al. Taianta 2014, 130, 470-474. (Year: 2014).*
Bergstrom et al. Eur. J. Clin. Pharmacol. 2003, 59, 357-366. (Year: 2003).*
Wood et al. Brain Res. 2006, 1095, 190-199. (Year: 2006).*
Conklin et al. Int. Cancer Therap. 2004, 3, 294-300. (Year: 2004).*
Leonarduzzi et al. Mol. Nutr. Food Res. 2005, 49, 1044-1049. (Year: 2005).*
Dirksen et al., "Rapid Oxime and Hydrazone Ligations with Aromatic Aldehydes for Biomolecular Labeling," Bioconjugate Chemistry, Dec. 2008, vol. 19 (12), pp. 2543-2548.
Gong et al., "Recent Advances in Bioorthogonal Reactions for Site Specific Protein Labeling and Engineering," Tetrahedron Letters, vol. 56 (17), Apr. 2015, pp. 2123-2132.
International Patent Application No. PCT/CA2018/050125, International Preliminary Report on Patentability dated Aug. 15, 2019.
International Patent Application No. PCT/CA2018/050125, International Search Report and Written Opinion dated Apr. 27, 2018.

(Continued)

*Primary Examiner* — Michael G. Hartley
*Assistant Examiner* — Sean R Donohue
(74) *Attorney, Agent, or Firm* — Borden Ladner Gervais LLP; Kathleen E. Marsman

(57) ABSTRACT

Methods of detecting an aldehyde-containing compound in a subject or in a sample from a subject are described herein, comprising administering an aldehyde-binding compound of Formula I to the subject, or combining such a compound with the sample; and detecting the product of the compound of Formula I and the aldehyde-containing compound. Detection of the product may involve imaging, such as MRI, CEST-MRI or positron emission tomography (PET) imaging; or may involve fluorescence or an electrochemical detection method. Biologically relevant aldehydes detected according to the described method can be used to monitor conditions such as brain injury, neurodegenerative disorders such as Alzheimer's disease, diabetes, heart disease, and cancer.

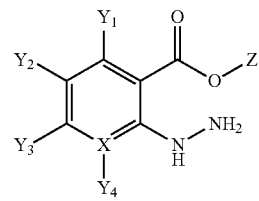

Formula (I)

11 Claims, 30 Drawing Sheets

(56) References Cited

OTHER PUBLICATIONS

Junior et al., "Serum Oxidative Stress Markers and Genotoxic Profile Induced by Chemotherapy in Patients with Breast Cancer: A Pilot Study," Oxidative Medicine and Cellular Longevity, Mar. 2015, 11 pages.

Kool et al., "Fast Hydrazone Reactants: Electronic and Acid/Base Effects Strongly Influence Rate at Biological PH," Journal of the American Chemical Society, Nov. 2013, vol. 135(47), pp. 17663-17666.

Mita et al., "Ruthenium-Catalyzed C—H Silylation of 1-Arylpyrazole Derivatives and Fluoride-Mediated Carboxylation: Use of Two Nitrogen Atoms of the Pyrazole Group," Synlett, 2014, vol. 25 (9), pp. 1291-1294.

Mukherjee et al., "Benzocoumarin Hydrazine: A Large Stokes Shift Fluorogenic Sensor for Detecting Carbonyls in Isolated Biomolecules and in Live Cells," ACS Sensors, Jan. 2017, vol. 2 (1), pp. 128-134.

Mukherjee et al., "Detection of Oxidative Stress-Induced Carbonylation in Live Mammalian Cells," Free Radical Biology and Medicine, Jul. 2015, vol. 84, pp. 11-21.

Shieh et al., "Design Strategies for Bioorthogonal Smart Probes," Organic and Biomolecular Chemistry, Dec. 2014, vol. 12 (46), pp. 9307-9320.

Wu et al., "An Overview of CEST MRI for Non-MR Physicists," EJNMMI Physics, Dec. 2016, vol. 3(1), 21 pages, Published online Aug. 2016, doi: 10.1186/s40658-016-0155.

\* cited by examiner

A)

B)

| | R¹ |
|---|---|
| 1a | H |
| 1b | I |
| 1c | NO₂ |
| 1d | SO₃H |
| 1e | OH |
| 1f | OCH₃ |

| | R¹ | R² |
|---|---|---|
| 2a | H | H |
| 2b | I | H |
| 2c | NO₂ | H |
| 2d | SO₃H | H |
| 2e | OH | H |
| 2f | OCH₃ | H |
| 7 | OCH₃ | CH₃ |

| | R¹ | R² |
|---|---|---|
| 3a | H | 2-SO₃H-Ph |
| 3b | I | 2-SO₃H-Ph |
| 3c | NO₂ | 2-SO₃H-Ph |
| 3d | SO₃H | 2-SO₃H-Ph |
| 3e | OH | 2-SO₃H-Ph |
| 3f | OCH₃ | 2-SO₃H-Ph |
| 4a | H | CH₃ |
| 4b | I | CH₃ |
| 4c | NO₂ | CH₃ |
| *4d | SO₃H | CH₃ |
| 4e | OH | CH₃ |
| 4f | OCH₃ | CH₃ |

| | R¹ | R² |
|---|---|---|
| 5a | H | CH₂CH₂NH₂ |
| 5b | H | CH=CHCH₃ |
| 5c | H | CH(OH)CH₂OH |
| 5d | H | CH₂OH |
| 6a | CH₃ | CH₃ |
| 6b | CH₃ | COOH |

| | R¹ |
|---|---|
| 8a | 2-SO₃H-Ph |
| 8b | CH₃ |

9

| | R¹ |
|---|---|
| 10a | 2-SO₃H-Ph |
| *10b | CH₃ |

11

12

METHODS AND COMPOUNDS FOR DETECTION AND BINDING OF ALDEHYDES

CROSS REFERENCE TO RELATED APPLICATIONS

This application claims the benefit of priority of U.S. Provisional Patent Application No. 62/455,132 filed Feb. 6, 2017, which is hereby incorporated by reference.

FIELD

The present disclosure relates generally to compounds that bind carbonyl-containing molecules such as aldehydes and ketones, in particular: aldehydes, and uses therefor. Such compounds are useful in imaging, in vitro diagnostics and treatment methods.

BACKGROUND

Carbonyls, such as aldehydes and ketones, can serve as markers of physiological conditions. However, there are few available aldehyde detection technologies for diagnostic applications, such as for imaging.

While there are some blood and breath testing systems available for detection of carbonyls in conditions such as diabetes (ketones), other types of testing often involves intrusive methods. For instance, studies linking aldehyde production to Alzheimer's disease may involve post mortem tissue sampling for testing by spectrophotometric methods. While reactive aldehydes formed in vitro as a result of oxidative stress are associated with neurodegenerative processes (Wood et al., 2006), there remains a need to detect and quantify such aldehydes.

Aldehyde species released in vivo as a result of the killing of cancer cells when a patient undergoes cancer chemotherapy may be indicators of the efficacy of a chemotherapy regime. See, for example Gomez Junior et al., (2015) in which serum oxidative stress markers were evaluated in chemotherapy patients.

Chemical Exchange Saturation Transfer magnetic resonance imaging (CEST-MRI) shows promise in detection of functional groups of physiological interest. CEST-MRI imaging can detect endogenous biomolecules that exchange protons with water. It remains a challenge for this technology to detect reactions with biologically significant functional groups such as carbonyls, under physiological conditions. For an overview of CEST-MRI see Wu et al., 2016.

Other detection methods used in CEST-MRI are described, for example, in US Patent Publication No. 2016/0082133 A1 entitled "Chemical Exchange Saturation Test (CEST) Based MRI using Reporter Genes and Substrates and Methods Thereof" in which polypeptide based reporters are employed to generate contrast in MRI imaging using the product of an enzyme.

US Patent Publication No. 2014/0294772 A1 entitled "Thymidine Kinase Diagnostic Assay for Gene Therapy Applications" describes an assay using nucleic acid sequences encoding thymidine kinases as reporters.

It is desirable to provide compounds and methods useful in detection or binding of aldehyde groups present in biologically relevant molecules.

SUMMARY

It is an object of the present disclosure to obviate or mitigate at least one disadvantage of previous diagnostic or therapeutic technologies pertaining to biologically relevant aldehyde-containing molecules. It is desirable to provide compounds and methods useful in detection or binding of carbonyl groups.

In a first aspect, the present disclosure provides method of detecting an aldehyde-containing compound in a subject comprising administering an aldehyde-binding compound of Formula I to the subject and detecting the product of the compound of Formula I and the aldehyde-containing compound, wherein the detecting employs imaging, such as MRI, CEST-MRI or positron emission tomography (PET) imaging;

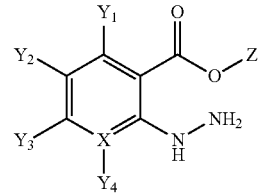

Formula (I)

wherein:

X is C or N;

Z is H, alkyl, cycloalkyl, or aryl; and $Y_1$, $Y_2$, $Y_3$ and $Y_4$ are independently: H; one or two substituents selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine; or $Y_1$ and $Y_2$, $Y_2$ and $Y_3$, or $Y_3$ and $Y_4$ join to form a 6-membered cycloalkyl or cycloaryl ring unsubstituted or substituted with one or two substituents selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine.

Further, there is described herein a method of detecting an aldehyde-containing compound in a sample comprising combining an aldehyde-binding compound of Formula I with the sample, and detecting the product of the compound of Formula I and the aldehyde-containing compound. The sample may be a tissue sample or biological fluid sample from a subject. Further, the detecting of the product may comprise using fluorescence or an electrochemical detection method. A printed chip may be used for detection.

Other uses, methods, compositions for use, and kits are described involving the compounds of Formula I for use in detecting aldehydes resulting from brain injury, neurodegenerative conditions such as Alzheimer's disease, detecting cell death, visualizing atherosclerotic plaque, inflammation, cardiac injury, atherosclerosis, detecting or treating ethylene glycol consumption, treating macular degeneration, or for conditions in which distinctive aldehyde or ketone production patterns can be detected.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
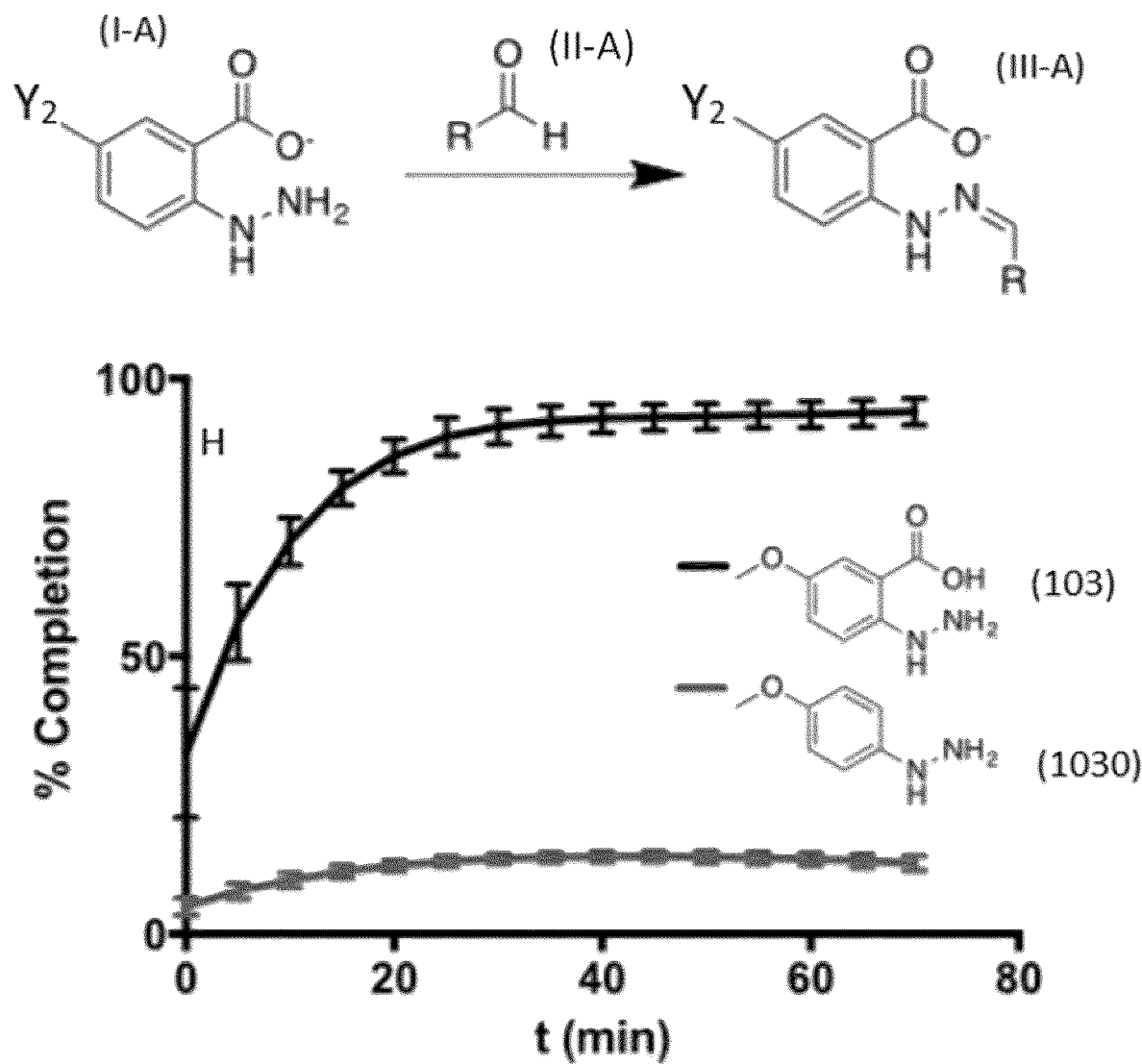
FIG. 1 shows a generalized reaction of hydrazine compounds of Formula I-A with aldehydes of Formula II-A, forming hydrazone compounds represented as Formula III-A.

The compounds of Formula I are capable of binding to compounds containing a carbonyl moiety, in particular, an aldehyde-containing moiety. Applications and advantages of this binding are described herein, for detection, as a probe or contrast agent, to cause fluorescence, or for binding in a manner that promotes treatment or prevention of undesirable diseases or conditions. Some of these compounds may be referred to as N-amino anthranilic acid compounds and derivatives. Compounds of Formula I may be used as small molecule probes for detecting aldehydes, for targeted delivery of linked compounds to a carbonyl-specific site, or for competitive binding to carbonyls in a physiological context. The compounds described herein bind to the carbonyl component of aldehydes under physiological conditions. The following specific applications are discussed in further detail herein. The compounds of Formula III, so formed, may be used as markers of the presence of subject aldehydes or other aldehyde-containing compounds of physiological interest. Applications of the compounds described herein are not limited to the applications and advantages described below.

In the aldehyde-binding compound according to Formula I, X is C or N; Z is H, alkyl, cycloalkyl, or aryl; and $Y_1$, $Y_2$, $Y_3$ and $Y_4$ are independently: H; a substituent selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine, with the caveat that no more than two of $Y_1$, $Y_2$, $Y_3$ and $Y_4$ be substituted; or $Y_1$ and $Y_2$, $Y_2$ and $Y_3$, or $Y_3$ and $Y_4$ join to form a 6-membered cycloalkyl or cycloaryl ring, unsubstituted or substituted with one or two substituents selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine.

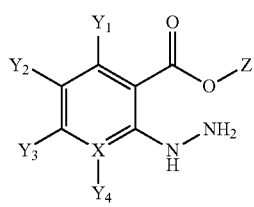

Formula I

In Formula I, $Y_2$ may be substituted with I, nitro, sulfo, carboxy, hydroxyl, alkoxy, cycloalkoxy, aryloxy, C1-6 alkyl, aryl, cycloalkyl, alkyne, tetrazine, or propargyl group. For example, $Y_2$ may be —OH, $CH_3$—O—, —I, —$SO_3$, or —$NO_2$.

In Formula I, Z may be H or $CH_3$.

Examples of formulae within the scope of Formula I are: Formula I-A, Formula I-B, Formula I-C, and Formula I-D, as depicted herein. In these formulae, substituents X, Z, and $Y_1$, $Y_2$, $Y_3$ and $Y_4$ are as defined for Formula I. When present in Formula 1-C or Formula 1-D, substituents $Y_5$, $Y_6$, $Y_7$, and $Y_8$ are selected from the group consisting of Br, Cl, I, nitro, sulfo, carboxy, hydroxyl, alkoxy, cycloalkoxy, aryloxy, C1-6 alkyl, aryl, cycloalkyl, alkyne, tetrazine, and propargyl; with the proviso that no more than two of $Y_5$, $Y_6$, $Y_7$, and $Y_8$ are present on Formula I-C or Formula I-D.

The compounds, or products thereof upon reaction with an aldehyde, may be modified or substituted in a manner that is appropriate for detection, such as by using click chemistry substituents, or by adding a detectable or reactive substituent.

The aldehyde-binding compounds described herein may be used as a CEST-MRI probe, as a fluorescent marker, or may be radio-labelled for use in positron emission tomography imaging (PET scan). The aldehyde-binding compounds or their counterpart products may be modified, or substituted. Such modifications may include a substituent.

The compounds described herein according to Formula I have numerous applications, such detecting a brain injury in a subject or in a biological sample from the subject. The brain injury to be detected or monitored may be as a result of a concussion, traumatic brain injury, anoxic brain injury, or may have occurred for other reasons.

The compounds of Formula I may be used for detecting or monitoring neurodegeneration in a subject or in a biological sample from the subject, for example, in a subject suffering from or at risk of suffering from Alzheimer's Disease or Parkinson's disease.

The compounds of Formula I may be used for detecting cell death in a subject or in a biological sample from the subject. Such a subject may be experiencing cell death as a result of chemotherapeutic killing of a tumour cell. In this way treatment efficacy for cancer patients undergoing chemotherapy can be monitored.

The compounds according Formula I may be used in visualizing atherosclerotic plaque in a subject, for example when a subject is suspected of having atherosclerosis, or is being monitored for atherosclerotic treatment efficacy. Inflammation, and other damage due to heart disease may also be detected using the methods described.

The compounds according Formula I may be used for diagnosing or treating ethylene glycol consumption in a subject. An aqueous antifreeze composition can be prepared, containing one or more of the aldehyde-binding compounds according to Formula I, as an additive together with and ethylene glycol. Such a composition may employ the compounds of Formula I to a competitive bind, and thereby lessen or avoid the poisoning effects of ethylene glycol consumption.

The compounds according Formula I may be used for treating macular degeneration in a subject.

A compound having a structure selected according to any one of Compounds 301 to 327, 4, or 5, as depicted herein can be formed by binding a compound according to Formula I with an aldehyde-containing compound. Such compounds are useful as a detectable marker of the presence, amount, and/or type of aldehyde-containing compound present in a subject or a sample.

A method is described herein for preparing a compound such as any one of compounds 301 to 327, 4 or 5. The method comprises reacting a compound according to Formula I with an aldehyde-containing compound under physiologic conditions. The method may be conducted in vitro or in vivo.

A method of detecting an aldehyde-containing compound in a subject is described herein which involves administering or providing the compound of Formula I to a subject, and subsequently detecting the product of the compound of Formula I and the aldehyde-containing compound using MRI, such as CEST-MRI, or with a PET scan.

Further, a method of detecting an aldehyde-containing compound in a tissue or biological fluid sample from a subject is described herein, the method comprising combining the compound of Formula I with the sample, and detecting the product of the compound of Formula I and the aldehyde-containing compound, for example by using fluorescence. The detected product may be, for example, one or more of compounds 301 to 327, or 4 or 5. The sample to be tested for the presence of an aldehyde may be comprised of a sample other than a subject's biological tissue or fluid, and may be an extracted sample, or a non-biological sample that is derived from a source other than a subject. Aldehydes from any source and any sample may be detected according to the described method.

In the methods described, the aldehyde-containing compound to be detected may be one or more of glycolic acid, acetone, $H_2N$—CH—CH—CO—H, malondialdehyde, crotonaldehyde, pyruvate, glyoxal, glyceraldehyde, DL-glyceraldehyde, glycoaldehyde, acetaldehyde, o-sulfobenzaldehyde, a secosterol, or 3-aminopropanal.

There is described herein a method of detecting a concussion or other brain injury in a subject comprising providing to the subject the aldehyde-binding compound according to Formula I for detecting an aldehyde-containing compound indicative of concussion or of another brain injury, and detecting a level of the aldehyde-containing compound indicative of said brain injury at or above a threshold level. Further, a method of detecting a concussion or other brain injury in a subject may involve exposing a biological sample from the subject to the aldehyde-binding compound according to Formula I, for detecting an aldehyde-containing compound indicative of concussion, and detecting a level of said aldehyde-containing compound at or above a threshold level.

A method of detecting Alzheimer's disease or disease progression in a subject is described herein, comprising providing to the subject the aldehyde-binding compound according to Formula I for detecting an aldehyde-containing compound indicative of Alzheimer's disease neurodegeneration, and detecting a level of said aldehyde-containing compound at or above a threshold level. Further, a method of detecting Alzheimer's disease or disease progression may comprise: exposing a biological sample from the subject to the aldehyde-binding compound according to Formula I for detecting an aldehyde-containing compound indicative of Alzheimer's disease, and detecting a level of said aldehyde-containing compound at or above a threshold level.

A method of determining treatment efficacy in a subject undergoing cancer chemotherapy is described herein comprising providing to the subject the aldehyde-binding compound according to Formula I for detecting an aldehyde-containing compound indicative of cell death, and detecting a level of said aldehyde-containing compound at or above a threshold level. Further, a method of determining treatment efficacy in a subject undergoing cancer chemotherapy may comprise exposing a biological sample from the subject to the aldehyde-binding compound according to Formula I for detecting an aldehyde-containing compound indicative of cell death, and detecting a level of said aldehyde-containing compound at or above a threshold level.

A method of visualizing atherosclerotic plaque in a subject is described herein, comprising providing to the subject the aldehyde-binding compound according to Formula I for detecting an aldehyde-containing compound indicative of atherosclerotic plaque, and detecting a level of said aldehyde-containing compound at or above a threshold level.

A method of detecting ethylene glycol toxicity in a subject is described herein, comprising providing to the subject the aldehyde-binding compound according to Formula I for detecting glycolic acid, and detecting a level of glycolic acid above a threshold level. Further, a method of detecting ethylene glycol toxicity in a subject may comprise exposing a biological sample from the subject to the aldehyde-binding compound according to Formula I for detecting glycolic acid, and detecting a level of said glycolic acid above a threshold level.

Additionally, uses of the compounds of Formula I are described herein for detecting a condition selected from the group consisting of: brain injury, concussion, neurodegeneration, Alzheimer's disease, Parkinson's disease, ethylene glycol poisoning, macular degeneration, or atherosclerosis in a subject, or for preparation of an imaging composition for detecting such conditions. A kit for detecting or monitoring these conditions is also described, wherein the kit comprises an aldehyde-binding compound according Formula I, together with instructions for use.

CEST-MRI Contrast Agent.

The resulting hydrazone formed from binding of the compounds described herein with a ketone or aldehyde group, containing the aldehyde to be bound, effectively through reaction or bond formation. A high CEST-MRI signal is produced when binding occurs with an aldehyde group. The signal so produced indicates the localized aldehyde carbonyl group in the body. Thus, the contrast agent according to Formula I may be used as a probe to detect localized aldehyde production within the body. Whole body imaging may be achieved if the contrast agent is circulating. Localized detection is possible through such imaging methods.

Fluorescent Screening of Samples In Vitro, Such as Point of Care Diagnostics.

Patient samples, such as biological fluids, may be screened to detect the systemic presence of elevated aldehydes, such as compounds containing ester functionalities. This may permit point-of-care screening for a variety of indications. Further, in vitro analysis of body fluids or tissues may be used to identify candidate patients who may require further testing such as the CEST-MRI test. Point of care in vitro diagnostic methodologies can be used as a companion blood screen to determine which subjects should go on to CEST-MRI testing, or may be used for stand-alone monitoring of a variety of conditions.

Labelling Compounds for Detection Using Other Technologies.

The compounds described herein may be labeled, such as by using radiolabeling. This permits visualization of aldehydes or other aldehyde-containing compounds in a subject using other methods, such as with positron emission tomography (PET) scanning, in which case the radioactive tracer binds to aldehyde-containing compounds, permitting visualization.

Detection of Conditions Characterized by Aldehydes.

Testing individuals for the presence of aldehydes, generally or specifically, may be useful in detecting or monitoring diseases such as degenerative neurological conditions (Alzheimer's, Parkinson's), brain injury (including but not limited to concussion, traumatic brain injury, anoxic brain injury), cancer, cardio-vascular disease, infectious disease, and diabetes. Different aldehydes and ketones present in body fluids, such as blood, serum, and plasma, as the different compounds possess different emission spectra. Quantification to aldehyde-containing compounds, as well as qualification to elucidate which compounds are present, can be undertaken.

Markers of Cellular Stress.

Carbonyl groups, generally, such as those found in biologically significant aldehydes, are released from dying cells as indicative of cellular stress. Disease states or conditions characterized by cellular stress can be monitored using the compounds or methods described.

Cancer Treatment Monitoring.

Death of cancer cells, occurring as a result of effective chemotherapy, results in an increase in aldehyde production. Detection of aldehydes so produced can lead to accurate and personalized monitoring of individuals undergoing treatment for cancer.

Brain Injury Detection and Monitoring.

There is a need for brain injury detection, for example in contact sports, extreme sports, following trauma or automobile accidents, or during cardiovascular surgery. The damaged brain shows an increased presence of aldehydes. There is a great need for tests that can contribute measurable parameters to brain injury detection protocols. Exemplary brain injury-related conditions include concussion, traumatic brain injury, and anoxic brain injury.

Alzheimer's Disease and Other Neurodegenerative Conditions.

Previous research has illustrated that Alzheimer's Disease patients have an increase in 4-hydroxy-2-nonenal (HNE) or 3-aminopropanal, cytotoxic lipid-derived aldehydes. This increase can be found early in the disease progression. Detection of aldehydes through imaging could detect this increase within subjects suspected of having Alzheimer's, or to detect disease progression. In Alzheimer's disease, there are imaging tracers that allow the visualization of beta-amyloid plaques in the brain using PET, but there is a need for blood or cerebrospinal fluid markers. Parkinson's disease is another example of a neurodegenerative condition for which detection of early stages and monitoring of disease progression would benefit from the instant methodologies using the compounds described herein.

Diabetes, Inflammation, Heart Disease, and Altered Metabolic Conditions.

While there are commercial blood and breath tests available for monitoring of diabetes, monitoring through carbonyl or aldehyde detection, such as monitoring of ketones, could be used as an alternative to or in conjunction with glucose monitors.

Visualizing Atherosclerotic Plaques.

Aldehydes present in atherosclerotic plaques would bind to the compounds of Formula I, permitting imaging of plaque presence, amount, and changes over time in individuals known or suspected to be susceptible to heart disease or stroke.

Derivatization of Aldehydes in Living Subjects.

The compounds described herein advantageously permit reaction with aldehydes or imaging aldehydes in vivo, within living subjects. The capability to derivatize aldehydes in vivo and thereby provide a 'turn-on' CEST-MRI probe would enable imaging of these molecules in living subjects. Further, probe analogs could be used to derivatize aldehydes in vivo, isolate the aldehyde conjugates ex vivo and characterize the structure of the aldehydes present in tissues. Advantageously, avoiding ex vivo derivatization can avoid generation of aldehydes during the derivatization process, which can in turn avoid false-positive aldehyde identification.

Diagnostic, Therapeutic and Preventative Applications Relating to Consumption of Ethylene Glycol.

The consumption of ethylene glycol, a component of fluids often used in automobiles as antifreeze or windshield wiper fluid, can lead to toxicity and even death. Upon consumption, the taste of the fluid is sweet, thereby seeming attractive to animals and unsuspecting humans. However, ethylene glycol is broken down by the body into toxic components including glycolaldehyde (3-hydroxyethanal or $HOCH_2CHO$) which contains an aldehyde group detectable with the compounds of Formula I. The instant compounds and methods may be used to ascertain poisoning as a result of ethylene glycol consumption. Further, because the compounds of Formula I bind to the toxic aldehyde-containing metabolites formed from ethylene glycol, the use of the instant compounds to avert the toxic effects of ethylene glycol consumption can be beneficial. Adding compounds of Formula I to fluids sold to the public, which contain ethylene glycol, may proactively avert damaging downstream effects of from occurring, should an animal or human inadvertently consume such a product The compounds described herein can be used as a diagnostic to detect such poisoning after it occurs in a body fluid of a subject, may be used as a treatment or antidote after such a fluid is consumed, or may be used as a preventative additive that is included in the product as sold so that a compound capable of binding to an aldehyde-containing toxin would be proactively present for individuals who may consume the product.

One antidote to ethylene glycol poisoning is alcohol, which displaces the toxic metabolites. Compounds according to Formula I may permit another therapeutic option.

Product Compounds of Formula III as a Signal.

While some of the applications of the technology focus on detection and quantification of aldehyde-containing compounds, it is possible to utilize the product of the reaction as a means to label other molecules for detection by CEST-MRI.

Therapeutic Applications for Bound Aldehyde Groups.

The compounds of Formula I can additionally be formed for therapeutic purposes, not simply diagnostic or imaging purposes. By binding harmful ketones or aldehydes, the damage associated with these effects can be minimized.

Macular Degeneration.

The degeneration of the macula may be caused by a variety of unavoidable aspects of ageing. Aldehyde-containing compounds are present in the eye of a subject with macular degeneration. By reducing exposure to agents known to enhance macular degeneration, for example by binding such agents or by binding aldehyde-containing compounds formed in macular degeneration using compounds according to Formula I, the associated damage can be ameliorated. Application directly as eye drops would permit direct contact to the eye.

Flow Cytometry for Detection of Aldehyde-Containing Compounds.

Sorting and imaging cells on an individual level is a powerful tool to ascertain different cell types and cell characteristics. By attachment of compounds of Formula I to cells possessing certain surface markers, or utilizing radio-labeled compounds of Formula I to ascertain other characteristics of cells, the compounds provide a highly sensitive tool for cell sorting and characterization. For example, malondialdehyde is a cellular breakdown product indicative of the cell death process. Compounds of Formula I which are able to bind to this particular aldehyde, permit a visualization of a cell's overall health and viability characteristics.

Compounds

The compounds, described herein as aldehyde-binding compounds, are useful for reactions with aldehydes resulting in the formation of a product. By "aldehyde-binding", as used herein, the term encompasses binding and/or chemically reacting with aldehyde-containing compounds to form a detectable product. Such aldehyde-binding compounds are those represented by Formula I, defined below:

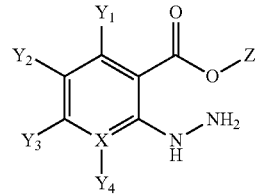

Formula I wherein:

X is C or N;

Z is H, alkyl, cycloalkyl, or aryl; and $Y_1$, $Y_2$, $Y_3$ and $Y_4$ are independently: H; one or two substituents selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine; or $Y_1$ and $Y_2$, $Y_2$ and $Y_3$, or $Y_3$ and $Y_4$ join to form a 6-membered cycloalkyl or cycloaryl unsubstituted or substituted ring with one or two substituents selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine.

The key features of Formula I are represented in all exemplary structures described and depicted herein. Below are select structures based on Formula I, labelled as Formula I-A, I-B, I-C and I-D.

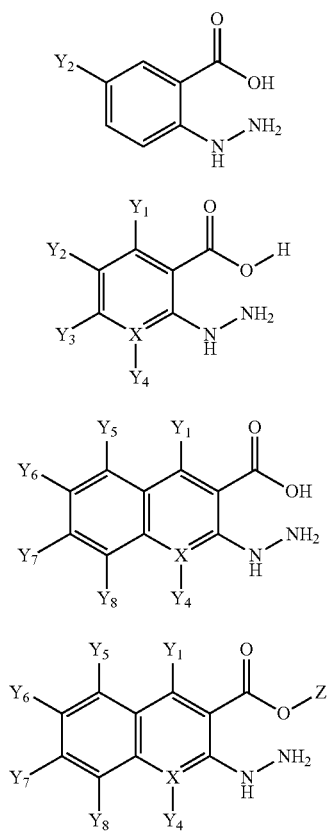

Formula I-A

Formula I-B

Formula I-C

Formula I-D

In compounds according to Formula I-C and I-D, or other hydrazine compounds according for Formula I in which $Y_1$ and $Y_2$, $Y_2$ and $Y_3$, or $Y_3$ and $Y_4$ are joined to form a 6-membered cycloalkyl or cycloaryl (conjugated) ring, in which up to two of the ring carbons may have substituents. Thus, zero, one, or two of the substituents $Y_5$, $Y_6$, $Y_7$ and $Y_8$ may be present and are selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine.

In structure of Formulae I-B, I-C and I-D, the structure permits "X" to be carbon or nitrogen. In certain examples described herein, it is illustrated that when X is N, reaction kinetics may be slower (than in comparable compounds where X is C), but the signal output for detection is much higher (i.e more sensitive detection). Different applications may require a higher sensitivity of signal, and speed of reaction kinetics may be less of a concern for certain application. However, for compounds that are somewhat transient, the speed of reaction kinetics may be a priority. Tailoring the compound of Formula I to suit the needs of the application is possible.

Compounds according to Formula I represent small molecules for imaging carbonyl groups, for example in aldehydes, under physiological conditions. This imaging may be done using chemical exchange saturation transfer magnetic resonance imaging (CEST-MRI), or may be done by fluorescence. The compounds include analogs of N-amino anthranilic acid (Compound 101), with one or more ring substituents.

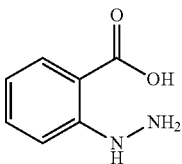

Compound 101

For example, a compound according to Formula I may have a substituent in the meta position to the carboxylic acid, examples of which are shown as Compounds 102-106.

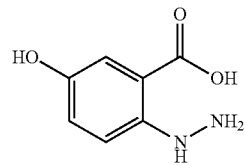

Compound 102

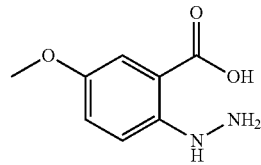

Compound 103

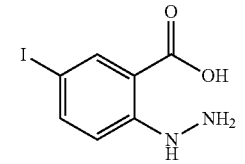

Compound 104

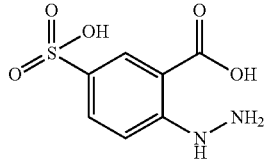

Compound 105

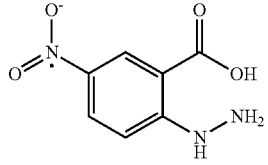

Compound 106

It is shown herein that N-amino anthranilic acid (Compound 101) and analogs thereof, such as Compounds 102-106, can rapidly bind to aldehydes to form a hydrazone under physiological conditions and, upon binding to an aldehyde, can generate CEST-MRI contrast.

Aldehyde-containing compounds have the Formula II: R—CO—R, wherein each R is independently H or a more complex substituent. Compounds of Formula II include aldehydes R—CO—H (Formula II-A) which may bind to the compounds of Formula I, and/or be detected by compounds of Formula I. Exemplary compounds to be bound or otherwise reacted with for detection include but are not limited to: glycolic acid (for example from ethylene glycol metabolism), acetone, $H_2N$—CH═CH—CO—H, malondialdehyde O═C—CH═C═O, crotonaldehyde, pyruvate, glyoxal, glyceraldehyde, DL-glyceraldehyde, glycoaldehyde, acetaldehyde, o-sulfobenzaldehyde, secosterols, or 3-aminopropanal.

Formula II

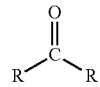

Formula II-A

Once an aldehyde-containing compound of Formula II binds to the compound of Formula I, the product formed is detectable, but may be transient or have a short stability. Thus, the product may be further reacted or functionalized as desired for detection.

The compounds formed as a result of reaction and/or binding of a compound of Formula I with aldehyde-containing compound according to Formula II, and as described herein, are represented by the product shown as Formula III, defined below, wherein Z, R, and $Y_1$ to $Y_4$ are defined as above.

Formula III

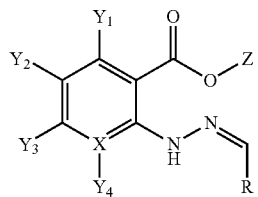

Compounds formed having a structure according to Formula III include, but are not limited to, the following structures having compound numbers 301 to 327, 4, or 5 below.

301-Z

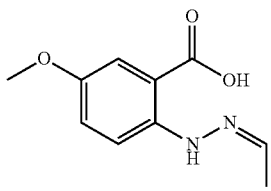

301-E

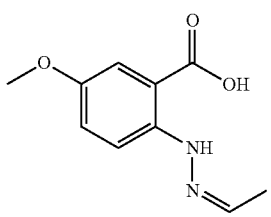

-continued

302

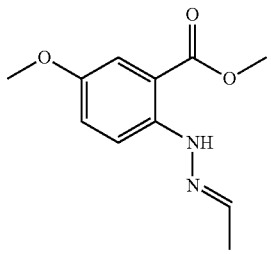

303

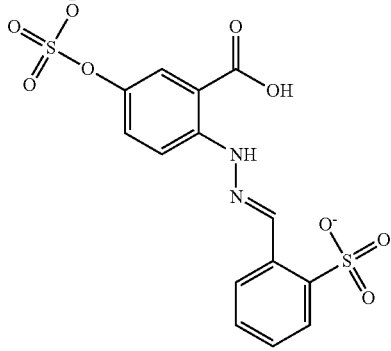

304

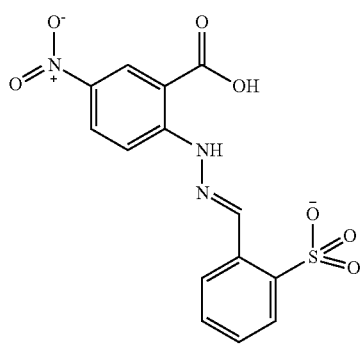

305

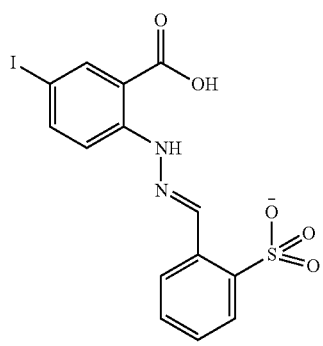

306

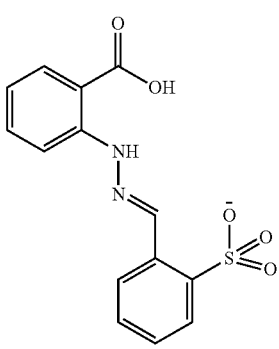

-continued
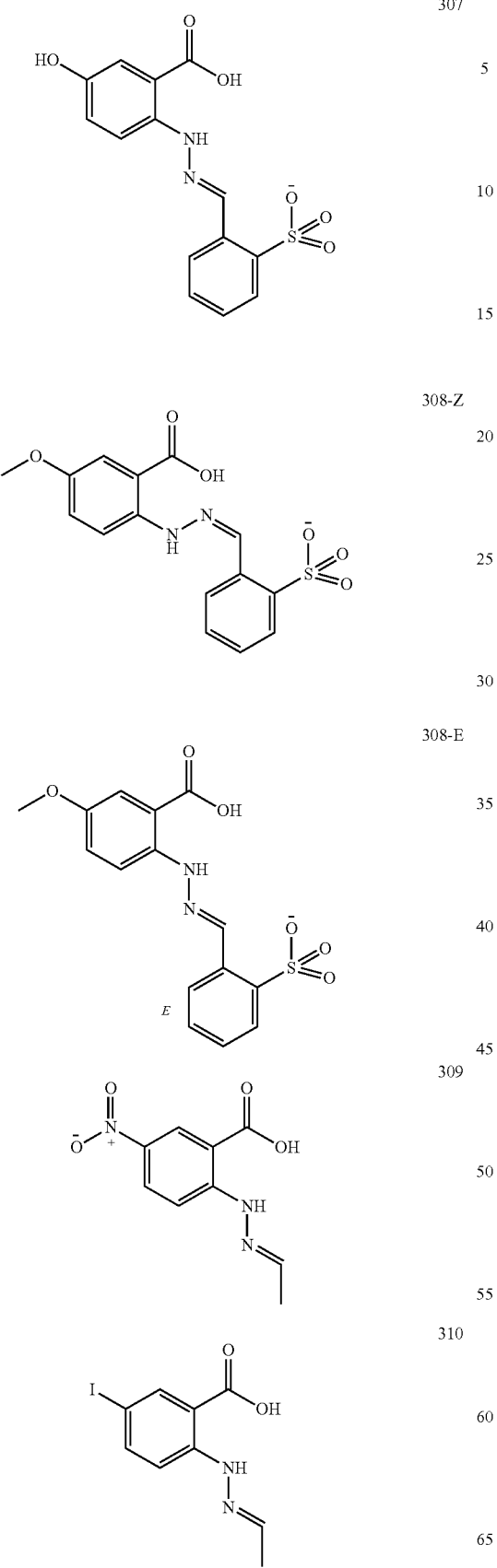
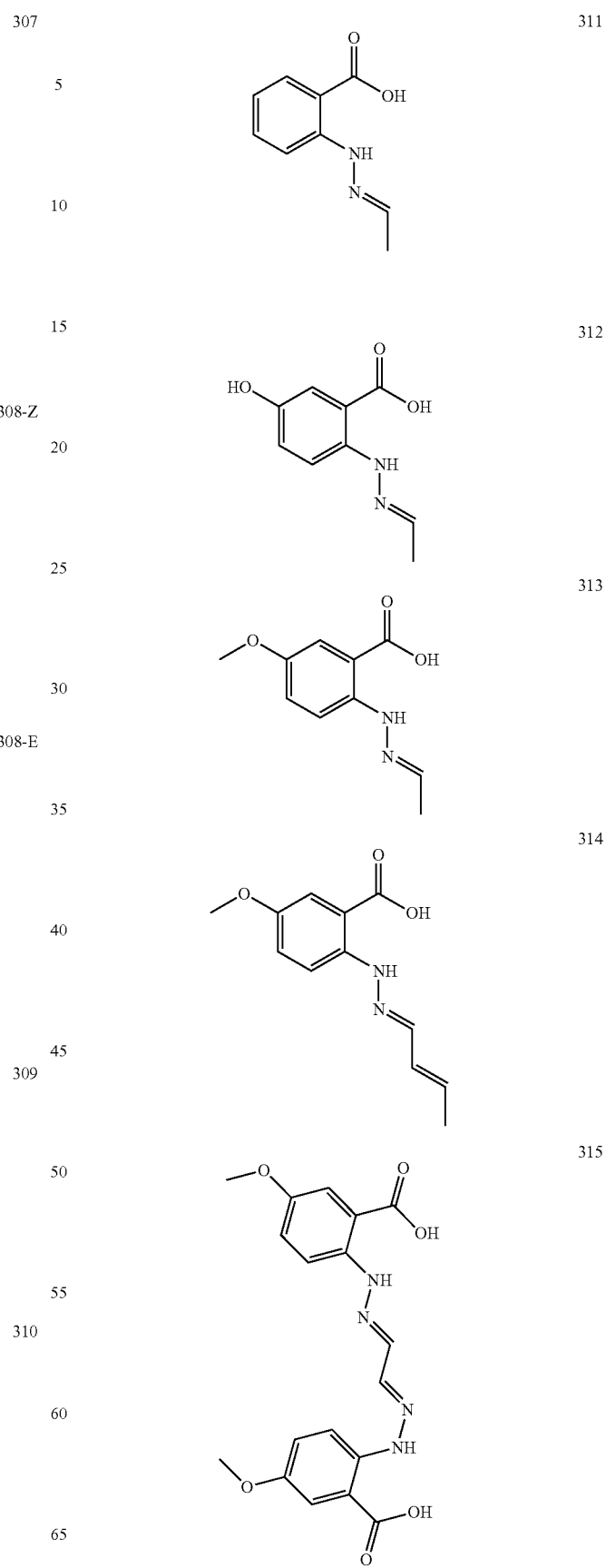

| | |
|---|---|
| 316 | 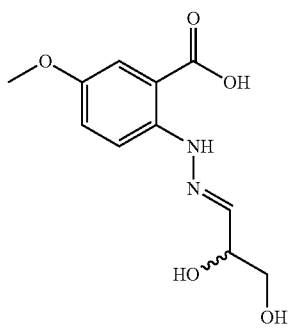 |
| 317 | 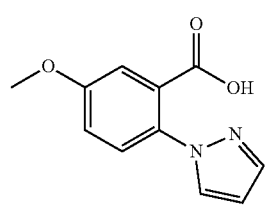 |
| 318 | 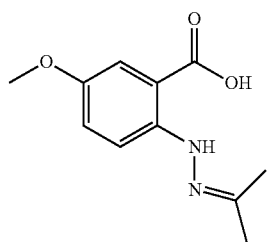 |
| 319 | 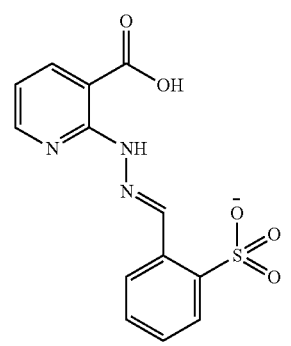 |
| 320 | 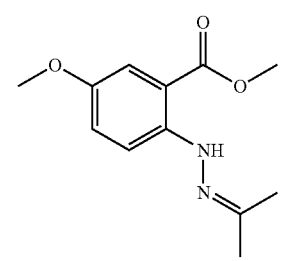 |
| 321 | 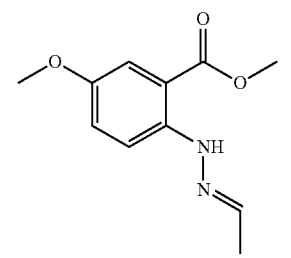 |
| 322 | 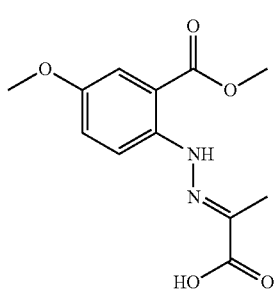 |
| 323 | 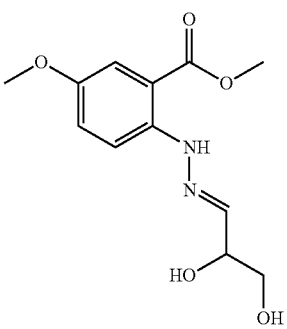 |
| 324 | 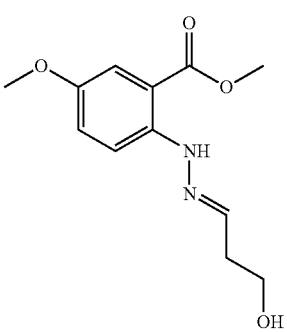 |
| 325 | 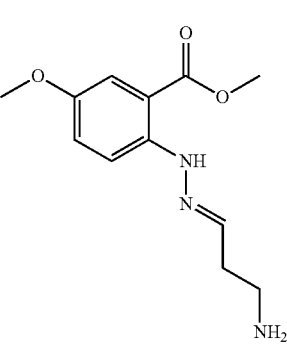 |
| 326 | 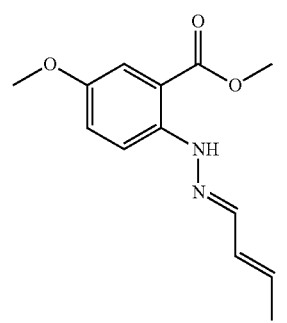 |

-continued

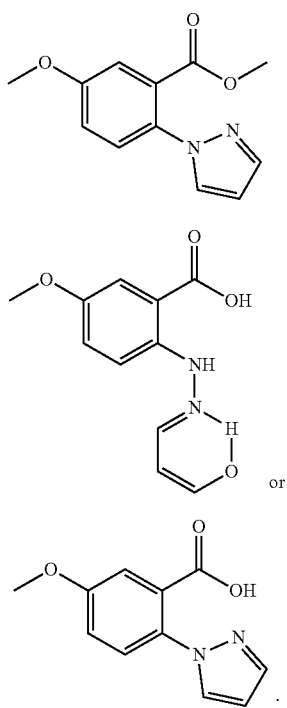

The compounds described herein can be used in vivo or in vitro. When used in vitro, tissues to be analysed may include blood (or serum or plasma), tears, urine, saliva, or the vapour/moisture present in breath. Saliva and/or breath vapour may be examined relative to a baseline sample to correct for aldehyde groups normally present on account of oral bacterial. Saliva diagnostics and other minimally invasive body fluid sampling may conveniently be used with regular sampling easily conducted to increase accuracy of sampling through a higher number of data points. Alternatively, biopsy or tissue sampling may be used for in vitro analysis.

For point of care diagnostic kits, a conveniently sized reader may be used to permit subjects to sample at home. Further, applications on smart phones may be incorporated to detect, compile, or report data so obtained.

A compound according to Formula I-A can bind with aldehydes represented as Formula II-A, wherein R is the remainder of the subject aldehyde molecule to be bound (non-H) to form a hydrazone of Formula III-A.

FIG. 1 shows a generalized reaction under which compounds such as Compounds 102-106 represented generally as Formula I-A. In Formula I-A, $Y_2$ may be H, or may be a substituent such as a halide (Br, Cl, I), nitro, sulfo, carboxy, hydroxy, alkoxy, cycloalkoxy, aryloxy, alkyl, aryl, cycloalkyl, alkyne, propargyl, or tetrazine. The rapid reaction kinetics of the probe (Compound 103) is shown in the graph.

A compound according to Formula I-A can bind with aldehydes represented as Formula II-A, wherein R is the remainder of the subject aldehyde molecule to be bound (non-H) to form a hydrazone of Formula III-A. The rapid reaction kinetics of the probe (Compound 103) shown in the graph of FIG. 1, with an aldehyde under physiological conditions is represented by the upper line. The lower line represents reaction kinetics of a comparative control (Compound 1030) in which the carboxylic acid group ortho to the hydrazine is absent. The absence of the carboxylic acid group of Compound 103 limits the completion of the reaction for Compound 1030.

Figure 2:
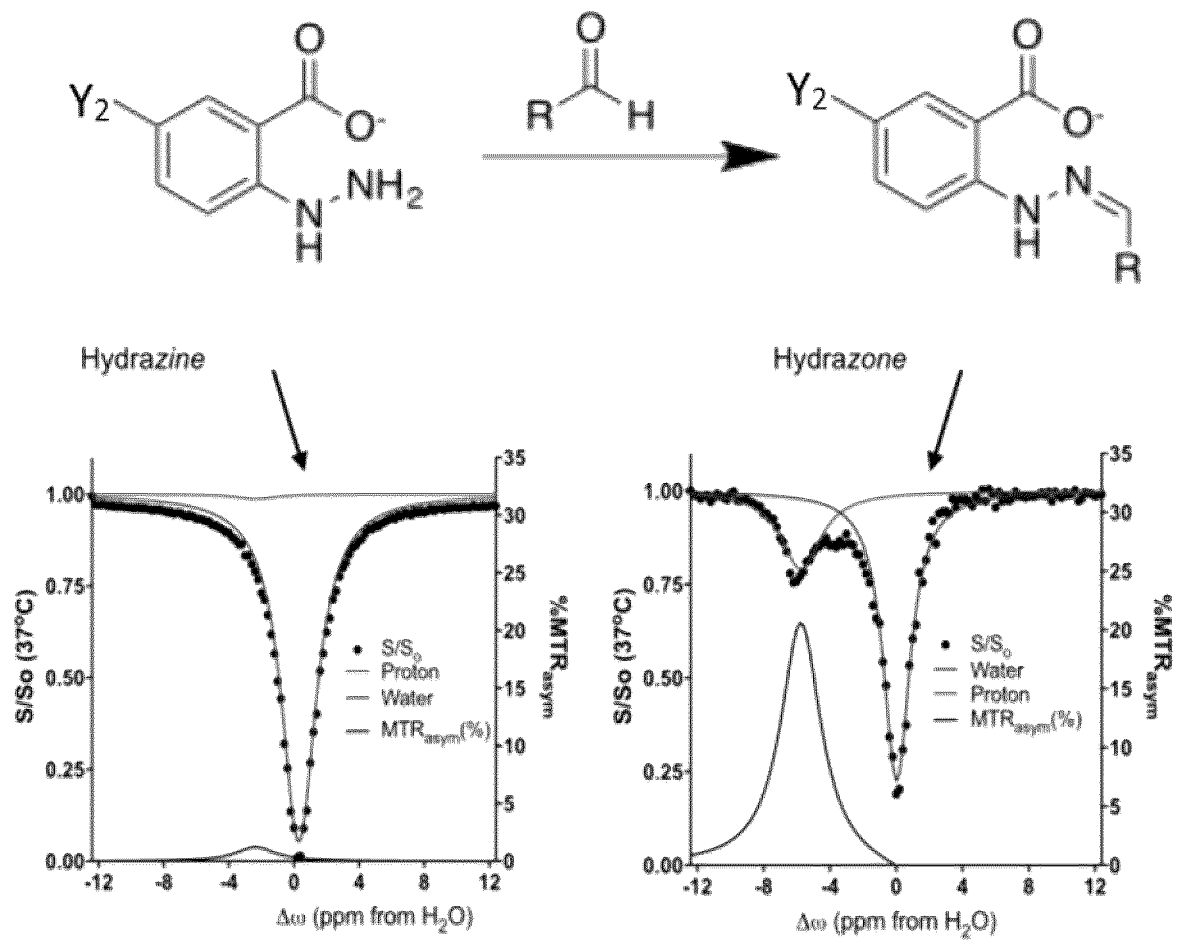
FIG. 2 shows that upon binding to an aldehyde, N-amino anthranilic acid and analogs thereof can generate CEST-MRI contrast.

FIG. 2 shows that upon binding to an aldehyde, N-amino anthranilic acid and analogs thereof can generate CEST-MRI contrast. Previously it was shown that the carboxyl group ortho to the hydrazine moiety is necessary for rapid reaction in PBS+10% v/v DMF (Kool et al., J. Am. Chem. Soc., 2013, 135 (47), pp 17663-17666), and here it is illustrated that this holds true for pure PBS. This illustrates that the ortho carboxylate is required for the generation of CEST-MRI signal. Further, FIG. 2 illustrates the selective production of the CEST-MRI signal (lowermost curve "$MTR_{asym}(\%)$") is minimal for the chart on the left, representing hydrazine, making the molecule effectively CEST-invisible. Upon reaction with an aldehyde (reaction at 37° C. in 1×PBS representing physiological conditions), the hydrazone formed is CEST-Active, as shown by the CEST-MRI signal peak (between −8 to −4 Δω (ppm from $H_2O$).

Figure 3:
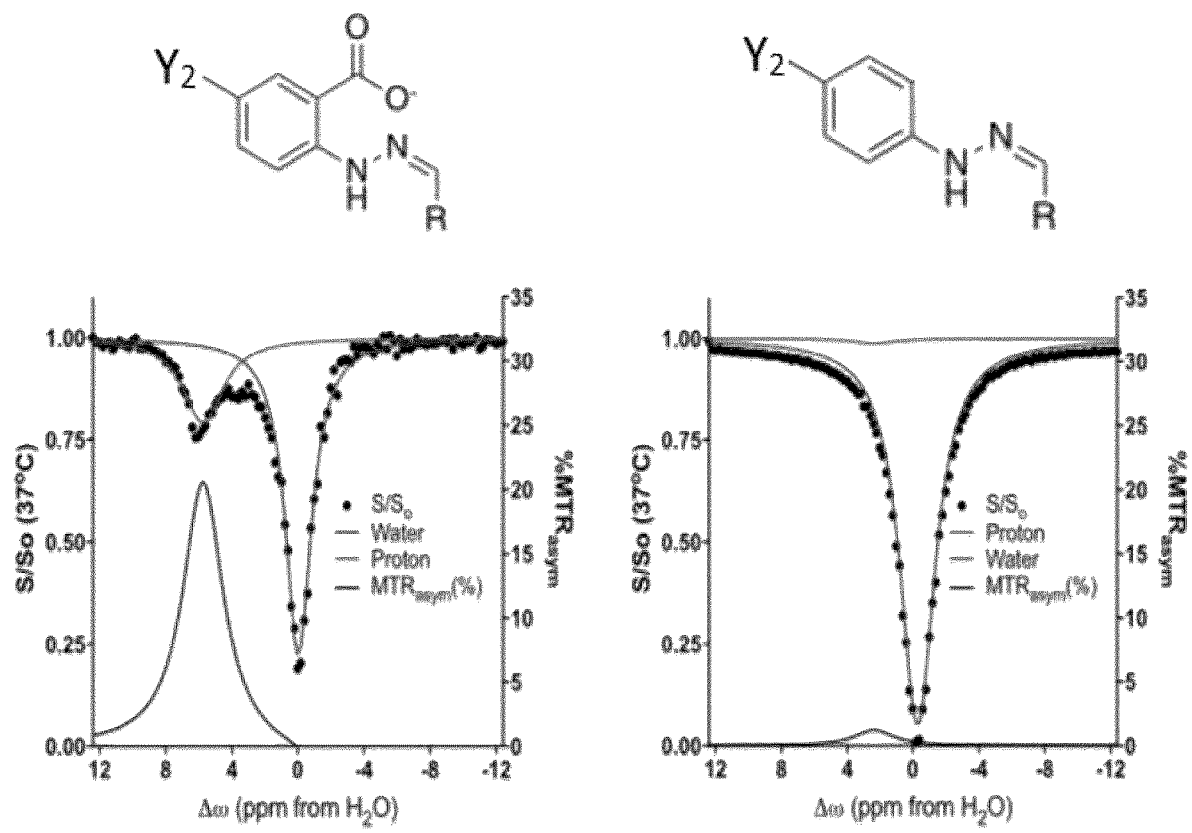
FIG. 3 illustrates the requirement for the ortho carboxylic acid (present on left, absent on right) in order to produce CEST-MRI contrast upon reaction of N-amino anthranilic acid, or analogs thereof, with aldehydes.

FIG. 3 illustrates the requirement for the ortho carboxylic acid to produce CEST-MRI contrast upon reaction of N-amino anthranilic acid, or analogs thereof, with aldehydes. The chart on the left shows CEST-active hydrazone according to Formula III-A, whereas the chart on the rights shows a CEST-invisible compound according to Formula IV, in which the ortho carboxylic acid is absent. This is evidenced by the CEST-MRI signal (lowermost curve "$MTR_{asym}(\%)$" being effectively absent for the chart on the right.

N-amino anthranilic acid and its analogs can thus be used to image a range of diseases and conditions associated with induced aldehyde formation in living subjects. Such diseases and conditions include atherosclerosis, cancers, brain injury, neurodegenerative diseases, and diabetes. These compounds provide an MRI diagnostic tool applicable to imaging of aldehydes as biochemical stress molecules.

The compounds of Formula I described herein serve as aldehyde derivatization agents amenable to reaction with aldehydes or imaging aldehydes in living subjects under physiological conditions. The compounds described herein may serve as molecular probes applicable to derivatization of aldehydes in vivo and provide a 'turn-on' CEST-MRI probe, permitting imaging of these molecules in living subjects.

Further, the compounds described herein can be used to derivatize aldehydes in vivo, isolate the aldehyde conjugates ex vivo and characterize the structure of the aldehydes present in tissues. By way of contrast, ex vivo derivatization can result in the generation of aldehydes during the derivatization process, yielding false-positive aldehyde identification. This detriment can be avoided if derivatization is permitted to occur in vivo.

Figure 4:
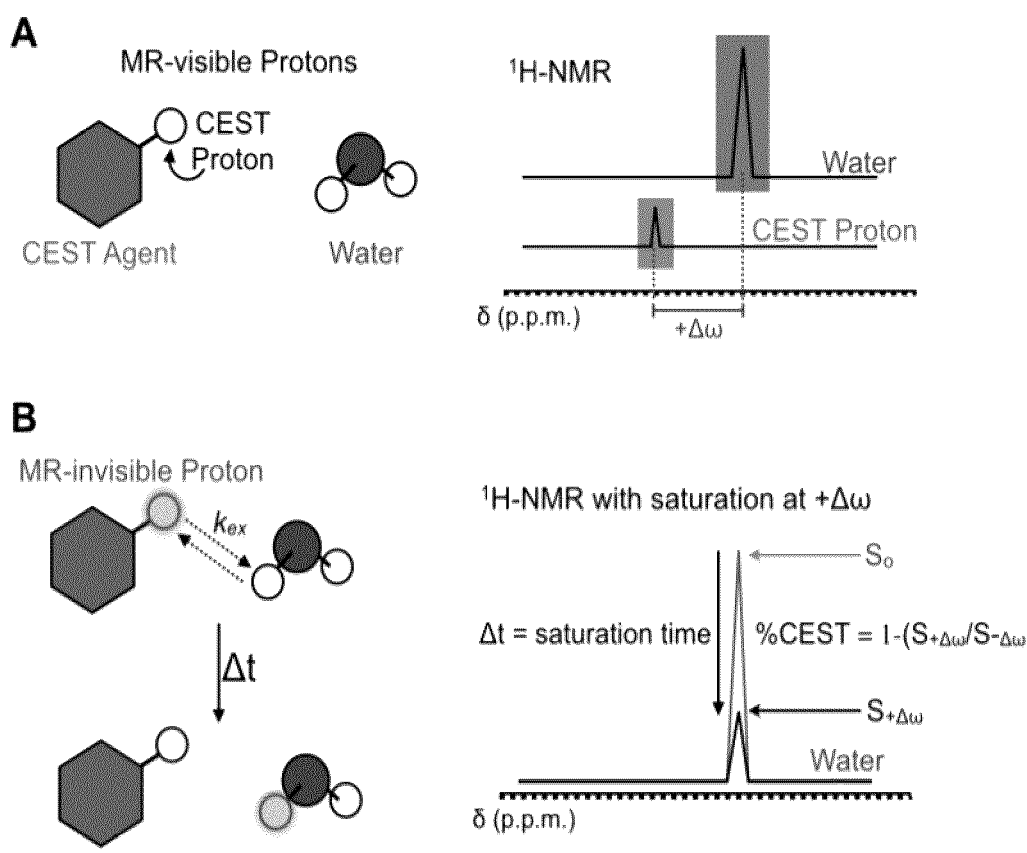
FIG. 4 is a schematic illustration of chemical exchange saturation transfer (CEST) imaging working through proton exchange between a contrast agent and water.

FIG. 4 shows chemical exchange saturation transfer (CEST) imaging working through proton exchange between contrast agent and water. In Panel A, an exchangeable proton (circle) on the CEST contrast agent (hexagon) has a chemical shift that is different from that of water by $^1$H-NMR. This chemical shift difference (+Δω) allows the exchangeable proton on the contrast agent to be spin saturated, effectively making it invisible to detection by magnetic resonance imaging (MRI). In Panel B, the exchangeable proton on the contrast agent is spin saturated and undergoes exchange with water protons, effectively making water invisible to the MRI (signal peak at $S_o$ versus that as $S_{+\Delta\omega}$). Since proton exchange occurs thousands of times per second, and since saturation is induced for approximately 3 seconds, thousands of water protons are "silenced" by a single contrast agent, allowing the depression of water to be mapped by the MRI. The signal intensity (% CEST) is calculated as the signal ratio with and without contrast agent proton spin saturation.

Figure 5:
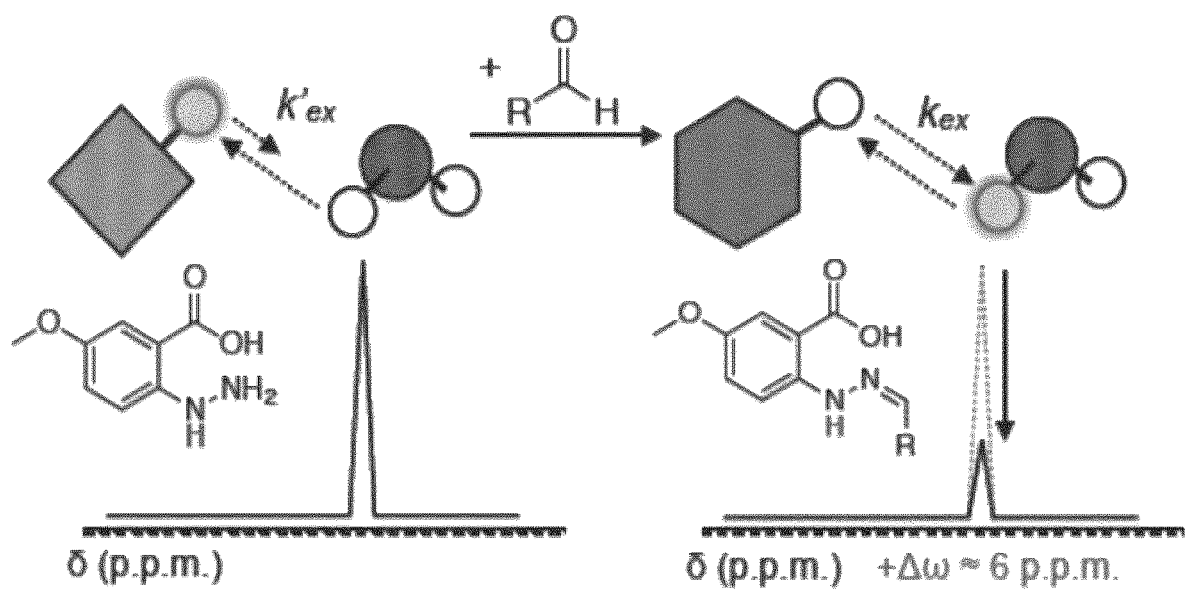
FIG. 5 provides a schematic representation of the mechanism of hydrazo-CEST imaging, as described herein, for MRI contrast enhancement. Compound 103 is shown reacting with an aldehyde.

FIG. 5 provides a schematic representation of the mechanism of "hydrazo-CEST", as described herein, for MRI contrast enhancement. Contrast enhancement is selectively turned on in the presence of aldehydes, such as biologically significant or bioactive aldehydes to be detected in vivo, or in patient samples in vitro (such as aldehydes and ketones). FIG. 5 illustrates the use of a compound according to Formula I (in this case, Compound 103) for reacting with an aldehyde RCHO. The exchangeable hydrazo proton (illustrated as a shaded light grey circle) does not result in the suppression of water signal when the contrast agent, based on substituted N-amino anthranilic acids, is in the hydrazine form (i.e. $k'_{ex}$ is not amenable to CEST-MRI). The covalent, bioorthogonal condensation of the hydrazine with the aldehyde or ketone to form a hydrazone results in an optimized exchange of the spin saturated proton with water, significantly reducing the water signal and producing CEST-MRI contrast enhancement (i.e. $k_{ex}$ is ideally suited to CEST-MRI).

Figure 6:
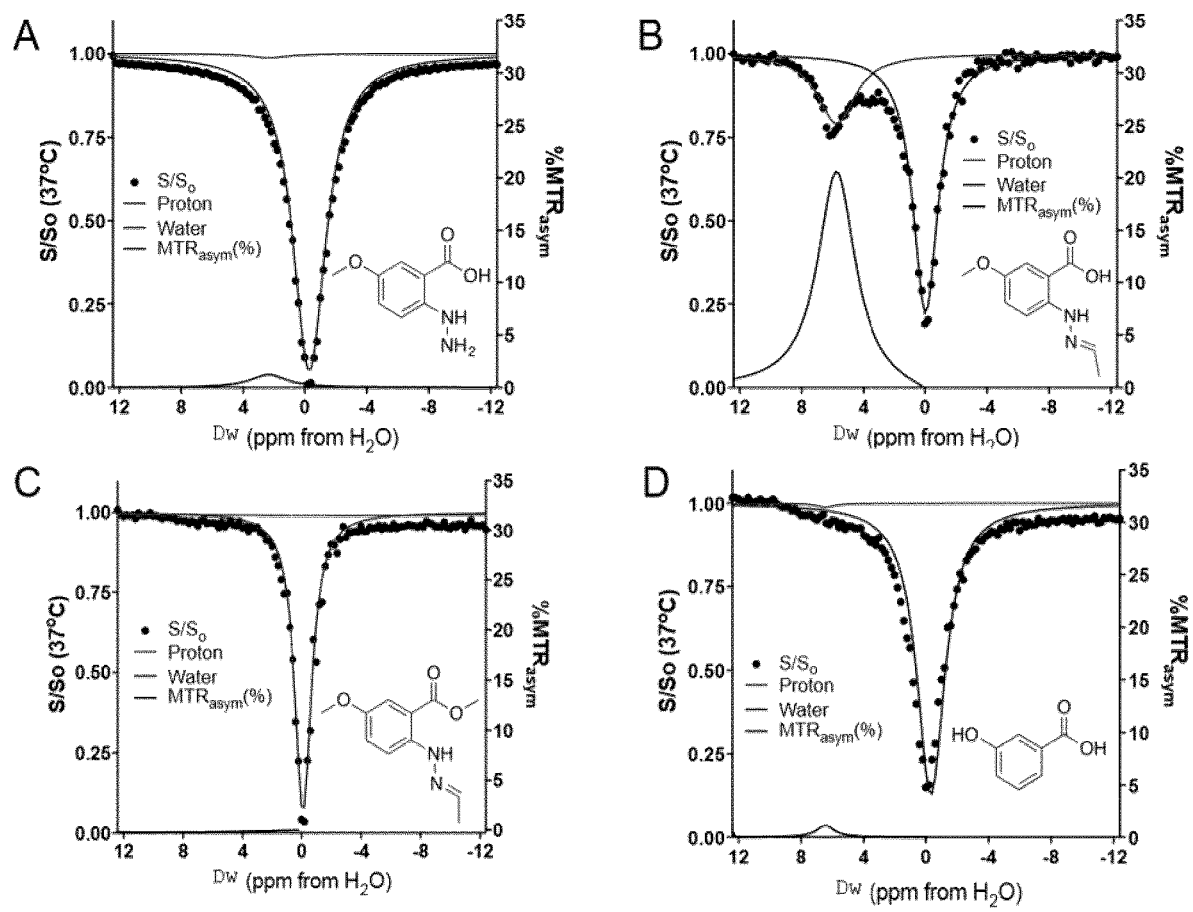
FIG. 6 illustrates Z-spectra, demonstrating the requirements of both the hydrazone and o-carboxylic acid for the production of contrast for CEST-MRI.

FIG. 6 illustrates Z-spectra, demonstrating the requirements of both the hydrazone and o-carboxylic acid for the production of contrast for CEST-MRI. In this figure, little CEST-MRI signal is produced in the hydrazine form (Panel A—Compound 103), but a substantial signal is produce following hydrazone formation from Compound 103 upon aldehyde binding, forming Compound 301 (Panel B). The absence of the o-carboxylic acid (e.g. methyl ester) prevents any CEST-MRI signal generation for compound 302 (Panel C), and the absence of the hydrazine moiety nearly completely abolishes signal production (Panel D, shown for comparison). Raw data points ($S/S_o$, black circles shown in the chart for each panel), exchangeable proton and water Lorentzian curves, and CEST-MRI signal production $MTR_{asym}$(%) are shown.

Figure 7:
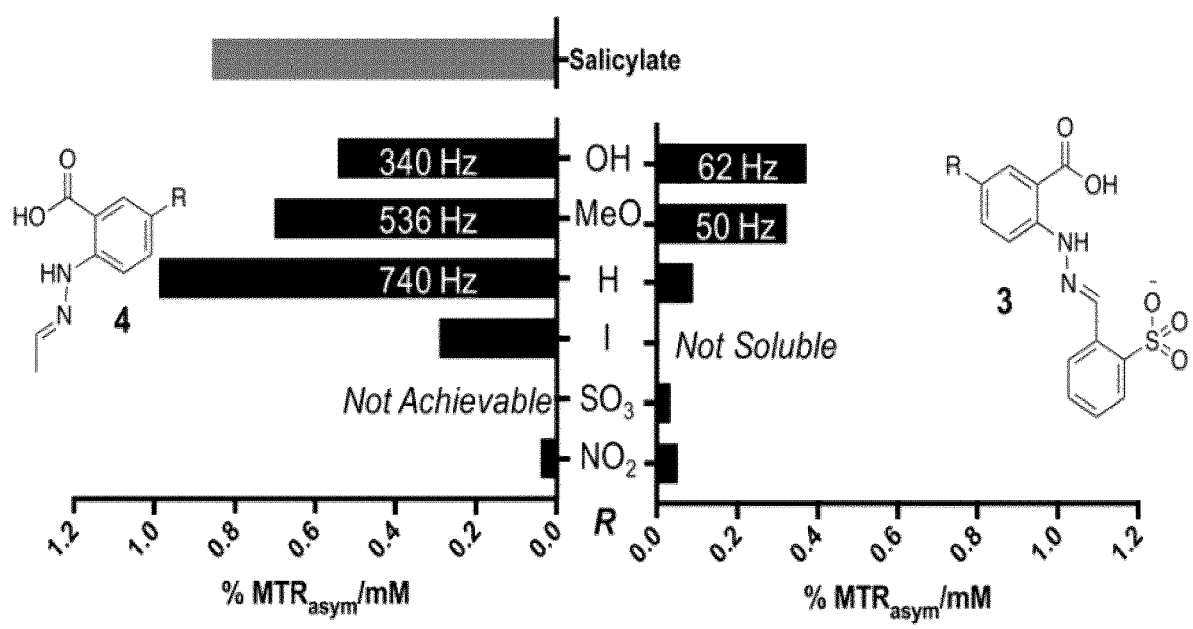
FIG. 7 shows the substitution of both the hydrazine and carbonyl substantially impact the CEST-MRI signal generation from hydrazo-CEST contrast agents.

FIG. 7 shows the substitution of both the hydrazine and carbonyl substantially impact the CEST-MRI signal generation from Hydrazo-CEST contrast agents. The more electron-donating the substituent on the hydrazine ring (i.e. OH, MeO), the stronger the signal across aldehydes tested. The more electron-withdrawing the aldehyde group (i.e. o-sulfobenzladehyde), the lower the CEST-MRI signal across all substituents, and the lower the tolerance for hydrazine substituents that are not electron-donating. Note that the sulfo-substituted hydrazine did not form a hydrazone with acetaldehyde.

Figure 8:
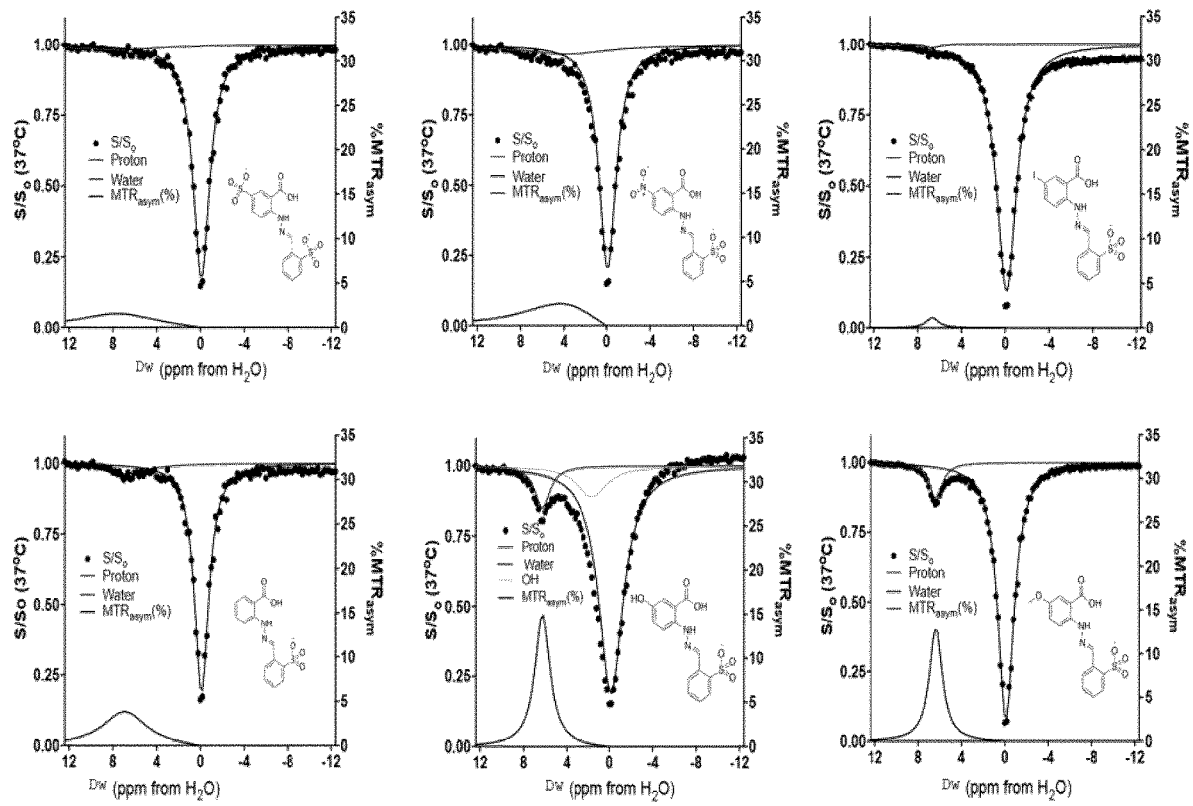
FIG. 8 shows the z-spectra of the o-sulfobenzaldehyde-substituted hydrazones with various hydrazine substituents.

FIG. 8 shows the z-spectra of the o-sulfobenzaldehyde-substituted hydrazones with various hydrazine substituents, showing not only the reduction of CEST-MRI signal production, but also the broadening of the signal peak with the electron-withdrawing substituents. Note that the hydroxy proton is exchangeable and was accounted for in a dedicated Lorentzian fit (curve shown). In the upper row, Compounds 303, 304 and 305 are shown. In the lower row, Compounds 306, 307 and 308 are shown.

Figure 9:
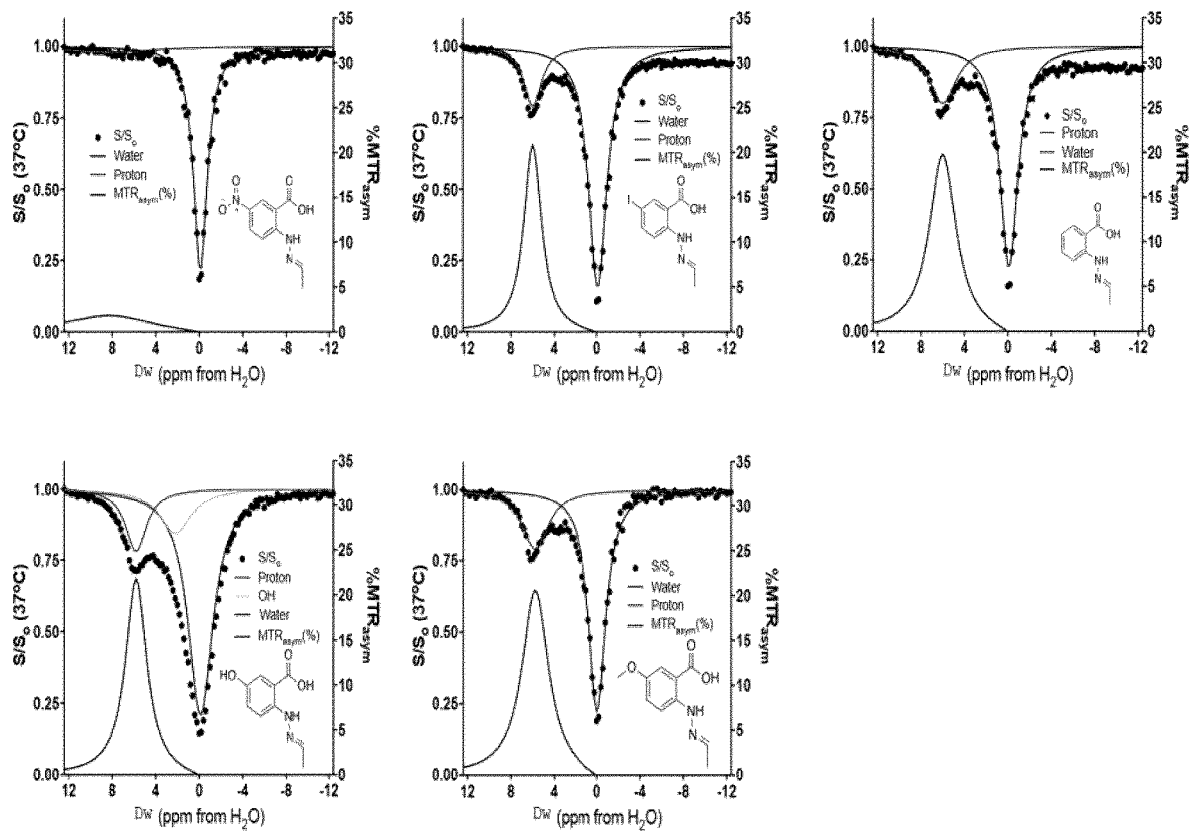
FIG. 9 shows the z-spectra of the acetaldehyde-substituted hydrazones with various hydrazine substituents.

FIG. 9 shows the z-spectra of the acetaldehyde-substituted hydrazones with various hydrazine substituents, showing not only the reduction of CEST-MRI signal production, but also the broadening of the signal peak with the electron-withdrawing substituents. Note that the hydroxy proton is exchangeable and was accounted for in a dedicated Lorentzian fit (curve shown). In the upper row, Compounds 309, 310 and 311 are shown. In the lower row, Compounds 312 and 313 are shown.

Figure 10:
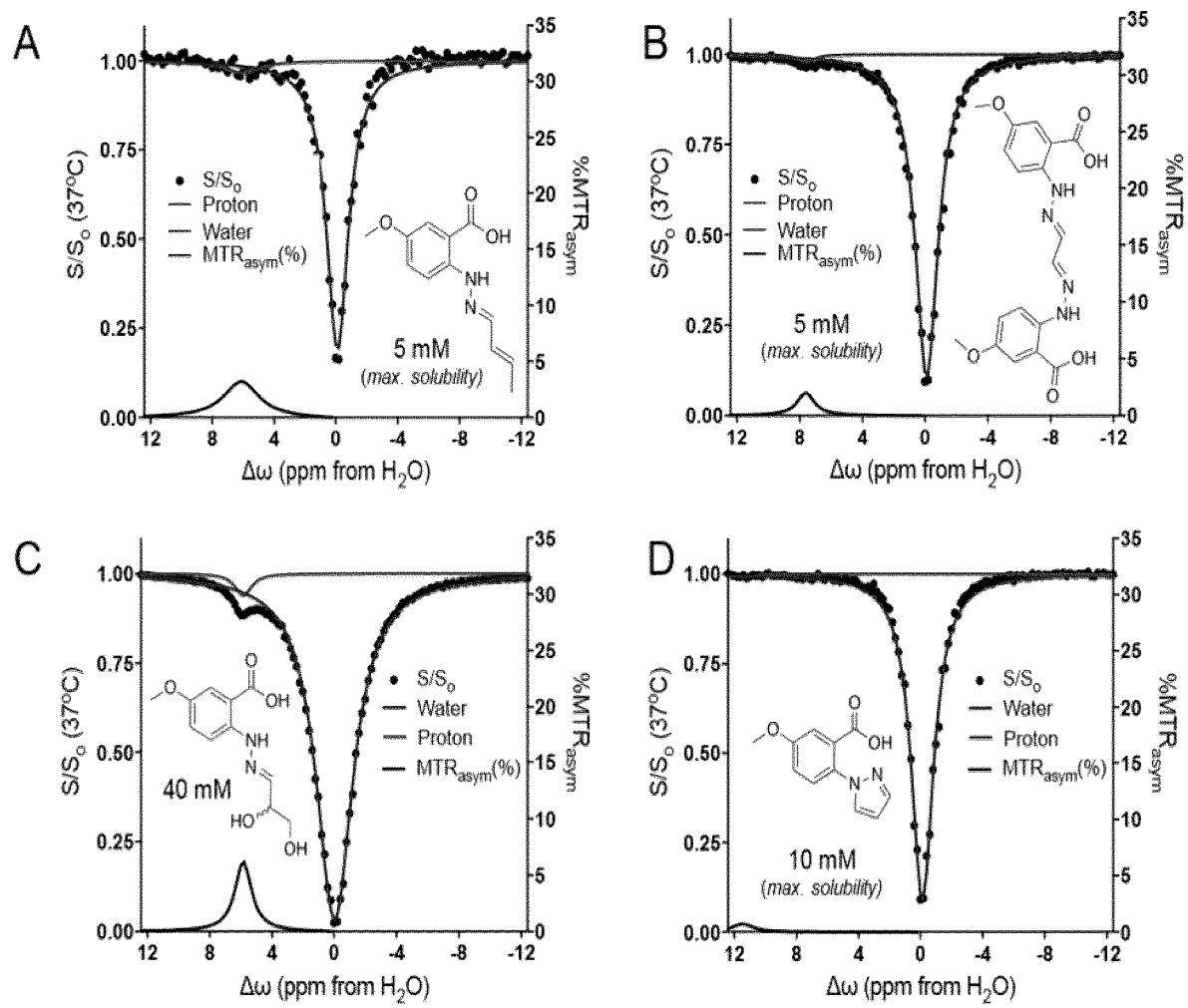
FIG. 10 shows the z-spectra of the best-performing Hydrazo-CEST agent (MeO-substituted) in complex with endogenous aldehydes.

FIG. 10 shows the z-spectra of the best-performing Hydrazo-CEST agent (MeO-substituted) in complex with endogenous aldehydes crotonaldehyde (Panel A), glyoxal (Panel B), glyceraldehyde (Panel C), and malondialdehyde, O=CH—CH2-CH=O (Panel D). The data show the limited solubility (Panels A, B, D) and CEST-MRI signal production (Panel C) with these hydrazone compounds. Malondialdehyde being an indicator of cell death. Panels A to D illustrate Compounds 314-317, respectively.

Figure 11:
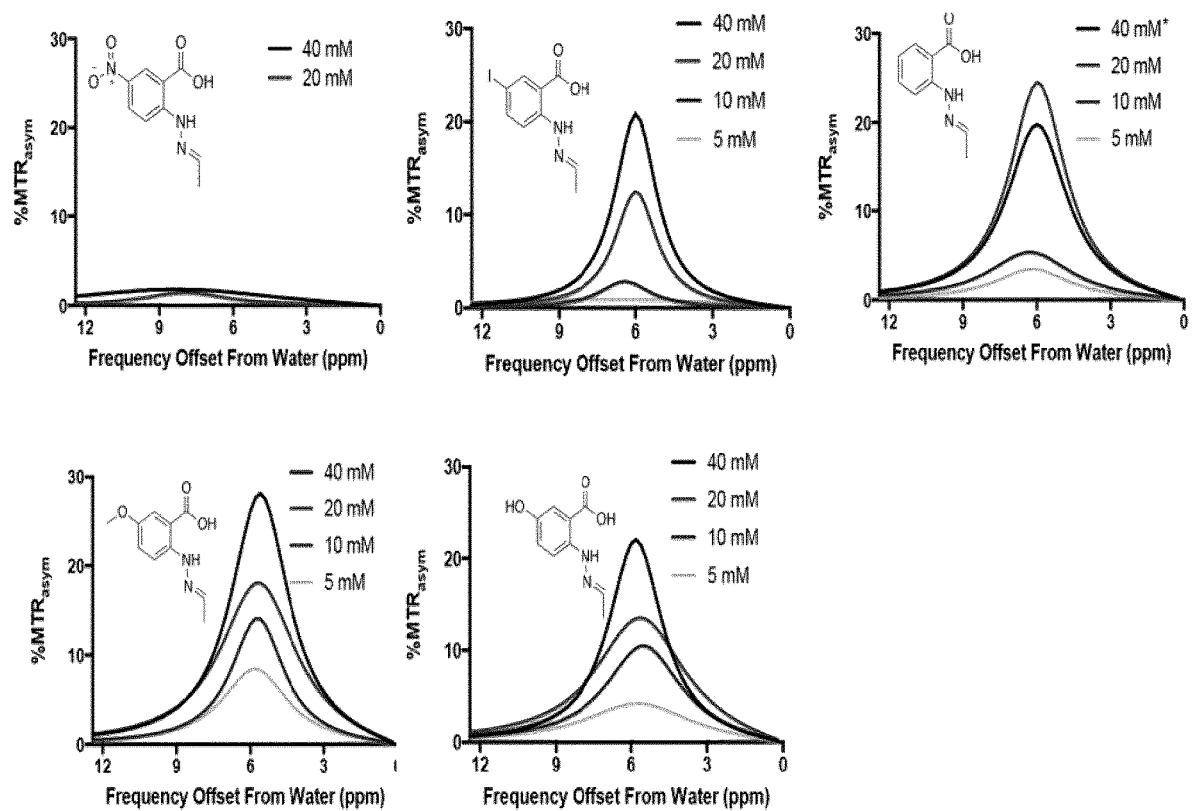
FIG. 11 illustrates the concentration dependence for acetaldehyde-derived hydrazones.

FIG. 11 illustrates the concentration dependence for acetaldehyde-derived hydrazones are shown for concentrations ranging from 5 to 40 mM. Note that the unsubstituted hydrazone was only slightly soluble at 40 mM. Compounds 309, 310, 311, 313, and 312 are represented, respectively.

Figure 12:
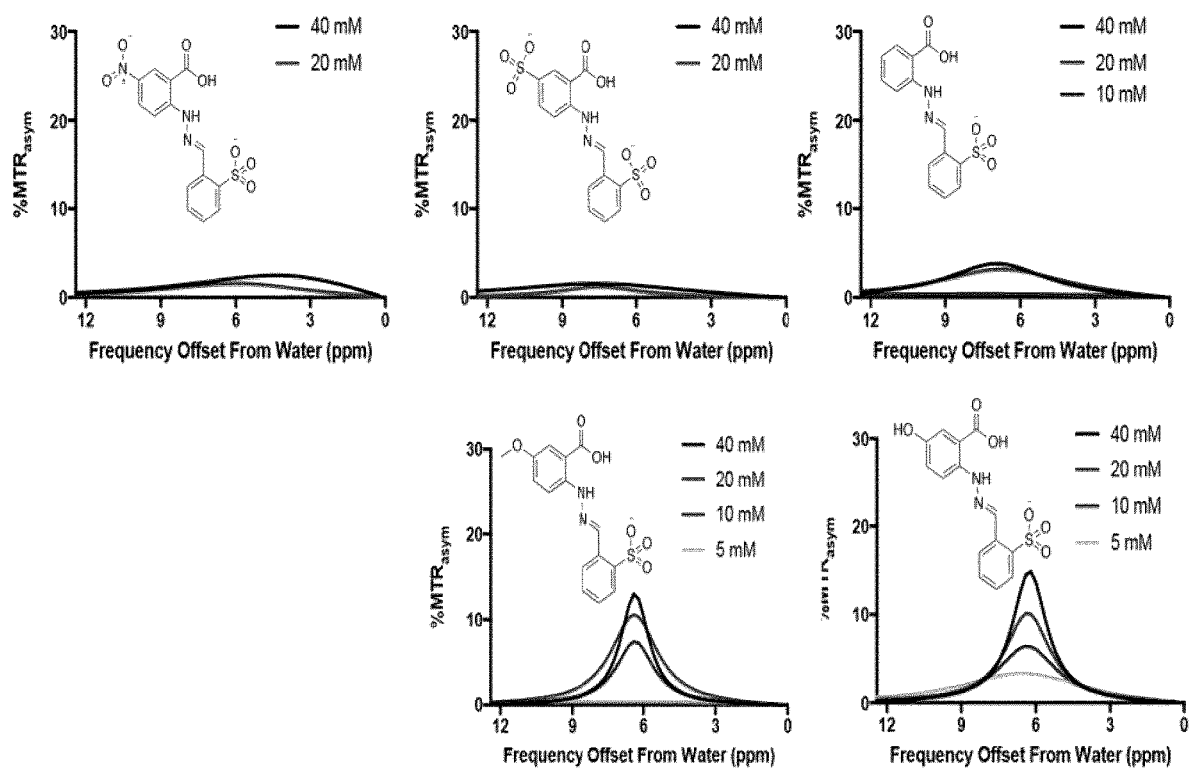
FIG. 12 shows the concentration dependence for o-sulfobenzaldehyde-derived hydrazones.

FIG. 12 shows the concentration dependence for o-sulfobenzaldehyde-derived hydrazones are shown for concentrations ranging from 5 to 40 mM. Compounds 304, 303, 306, 308, and 307 are represented, respectively.

Figure 13:
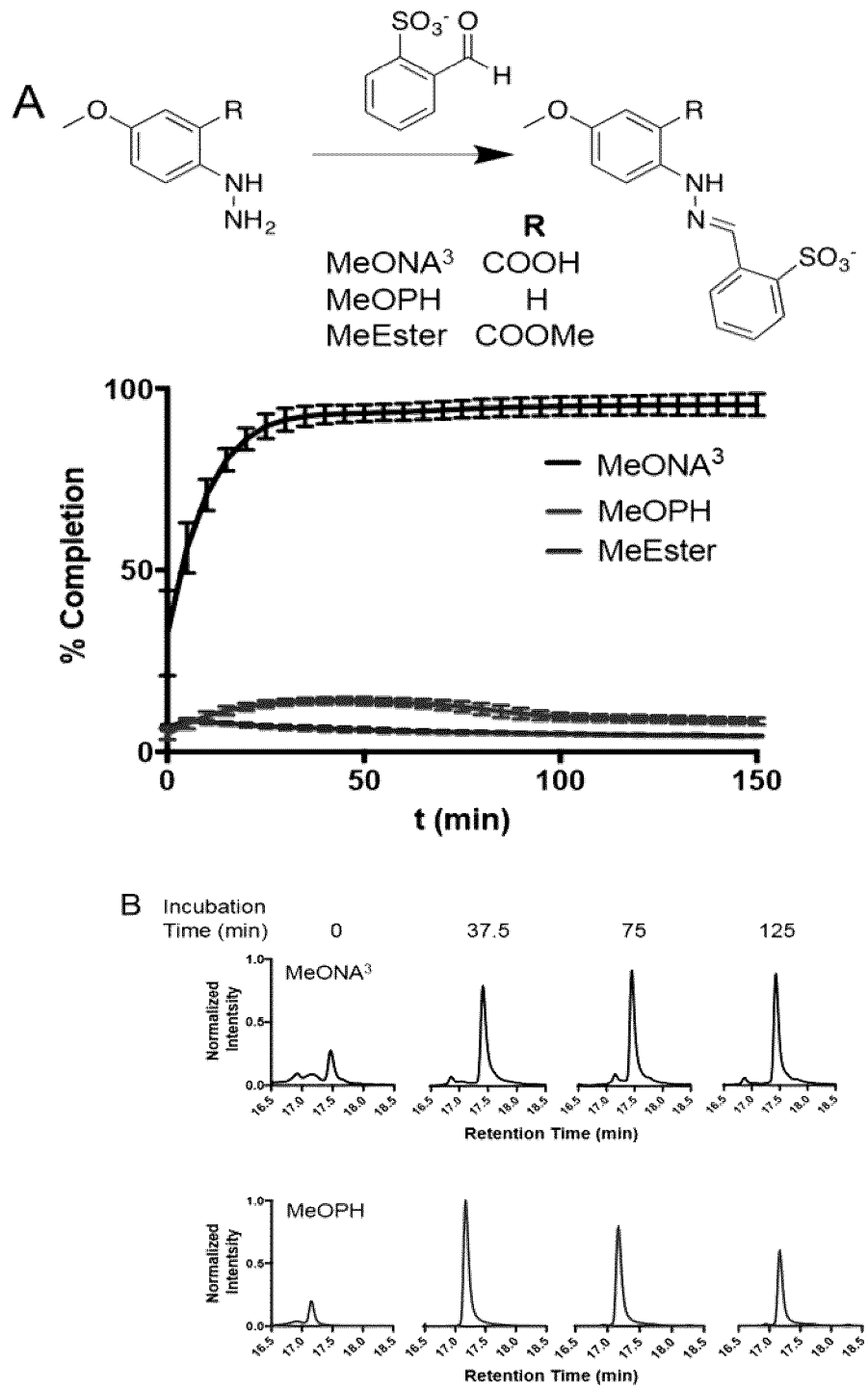
FIG. 13 illustrates the o-carboxylic acid contributes to substantial reaction completion as well as long-term stability of the product hydrazone under physiological conditions.
Figure 14:
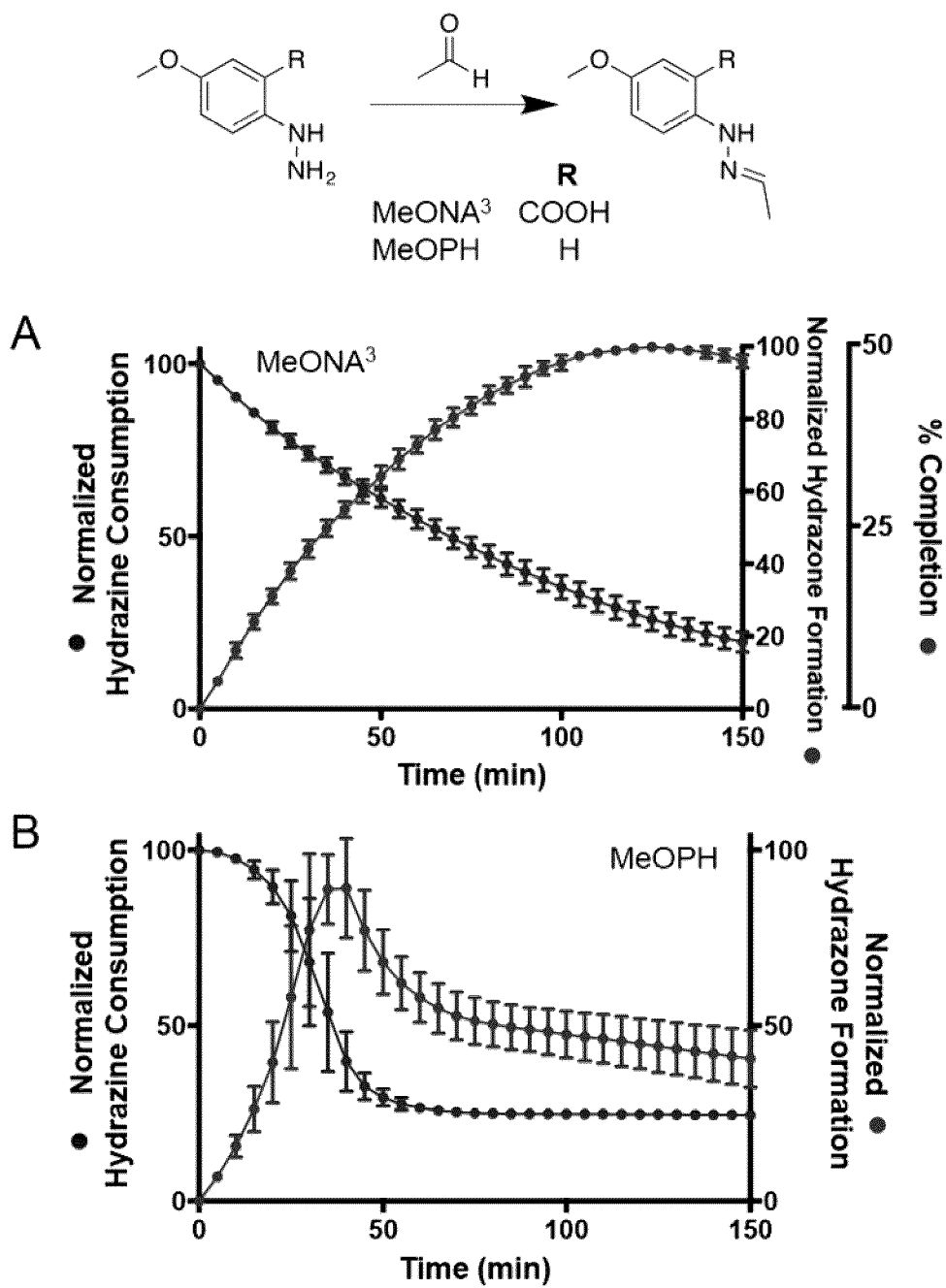
FIG. 14 shows the reaction progress and product stability for hydrazone formation between acetaldehyde and (Panel A) MeONA$^3$ or (Panel B) MeOPH.

FIG. 13 illustrates the o-carboxylic acid contributes to substantial reaction completion as well as long-term stability of the product hydrazone (Compound 308) under physiological conditions. Panel A shows kinetic plots for the reaction of the various hydrazines with o-sulfobenzaldehyde are shown, demonstrating that the carboxylic acid moiety is necessary for driving the reaction to completion, and to maintaining the stability of the hydrazone product. Panel B shows high-pressure liquid chromatography traces of the reaction of MeONA$^3$ (upper) and MeOPH (lower) with o-sulfobenzaldehyde. The hydrazone peak is shown (r.t.=17.5 min for MeONA$^3$ and 17.2 min for MeOPH) at the time points indicated, showing a loss of the MeOPH-derived hydrazone but stability of the MeONA$^3$-derived product over time. All reactions were performed in 1×PBS at 37° C., and points represent mean±s.d. for n=3 trials FIG. 14 shows the reaction progress and product stability for hydrazone formation between acetaldehyde and (Panel A) MeONA$^3$ or (Panel B) MeOPH. The MeOPH-acetaldehyde hydrazone was highly unstable, preventing accurate determination of molar extinction coefficient and subsequent calculation of hydrazone calculation. The carboxylic acid ortho to the hydrazine is critical to the stability of the formed hydrazone product. All reactions were performed in 1×PBS at 37° C., and points represent mean±s.d. for n=3 trials.

Figure 15:
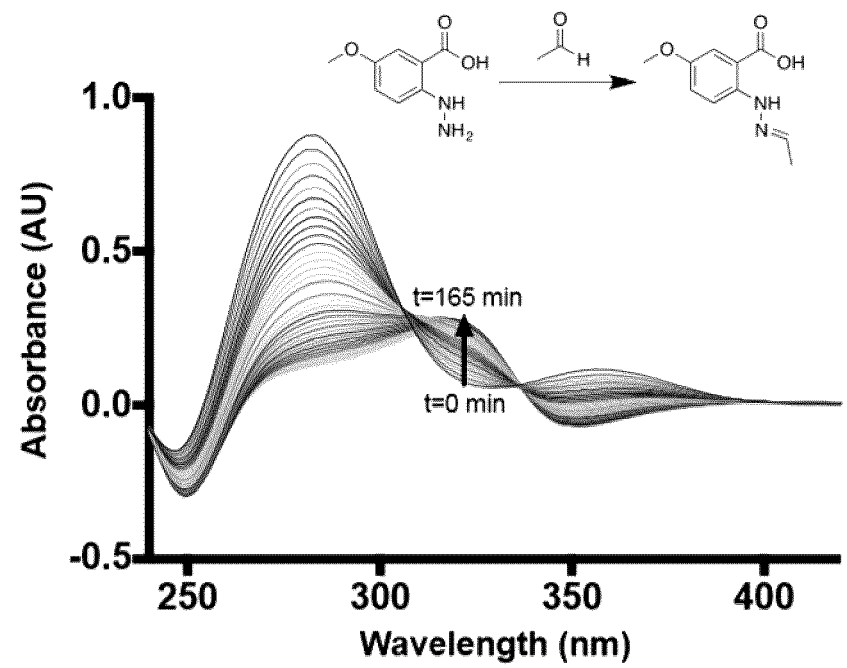
FIG. 15 shows representative UV-Vis spectral traces for hydrazone formation for Compound 313.
Figure 15:
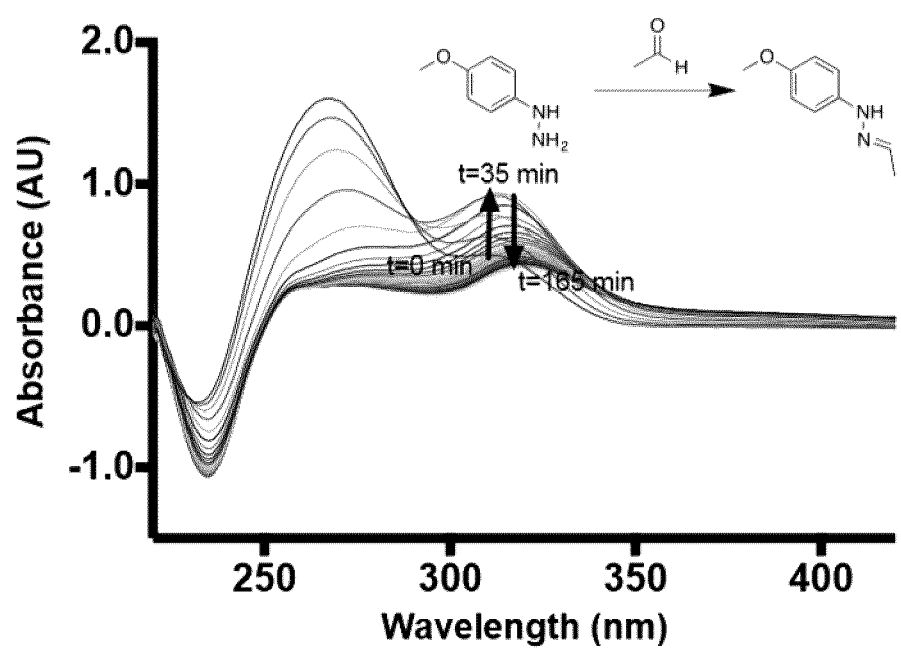

FIG. 15 shows representative UV-Vis spectral traces for hydrazone formation between acetaldehyde and (top, Compound 313) MeONA$^3$ or (bottom) MeOPH, demonstrating the instability of the MeOPH-derived hydrazone. All reactions were performed in 1×PBS at 37° C. These data illustrate the difference between the structure of Compound 313 having an acid group, versus the lower panel where the acid group is absent. The acid group contributes to the efficacy of the compounds of Formula I in the kinetics of product formation (Formula III, in this case compound 313), and in the stability of the product formed. Stability may be important for in vivo imagine, as a relatively stable product is needed to permit appropriate detection.

Figure 16:
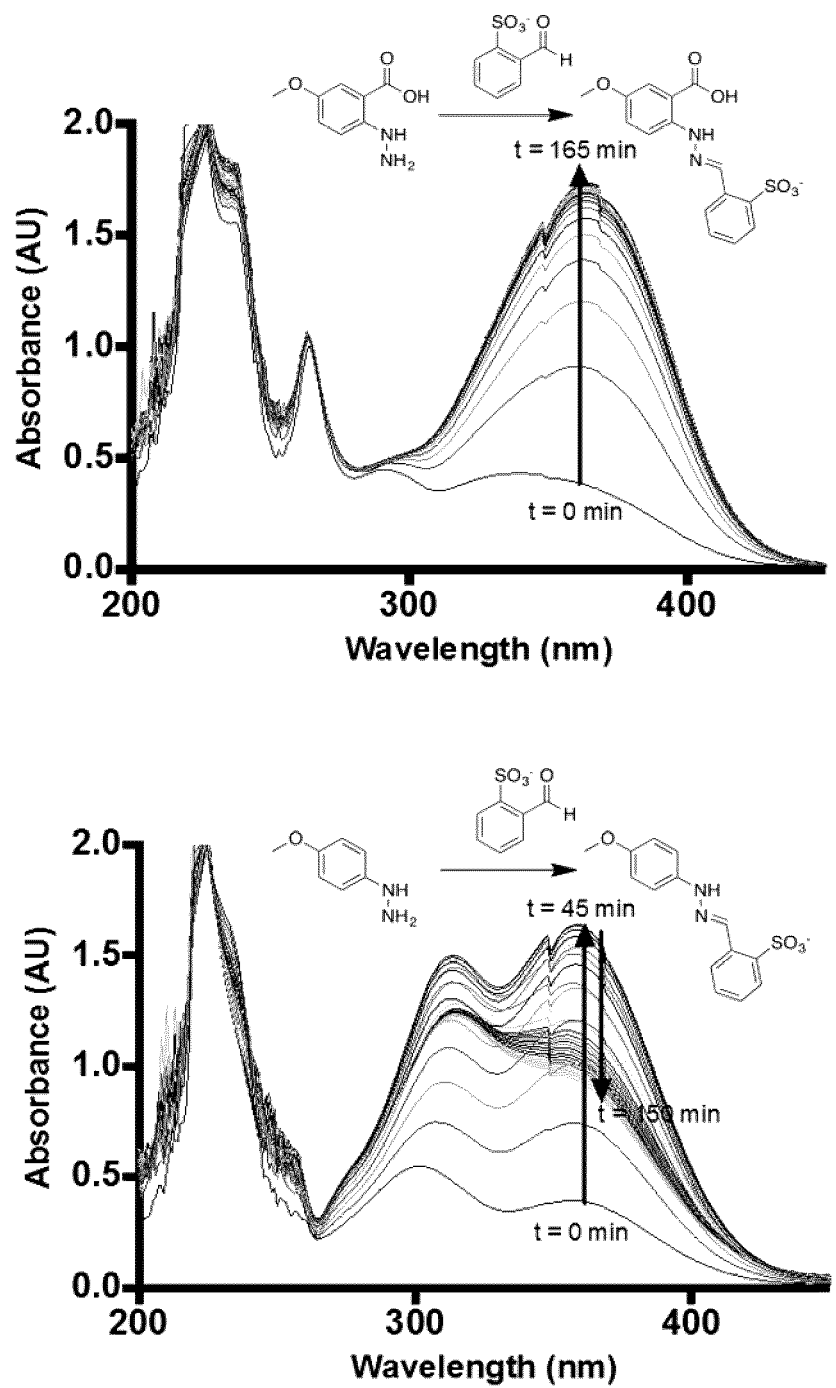
FIG. 16 shows representative UV-Vis spectral traces for hydrazone formation for Compound 308.

FIG. 16 shows representative UV-Vis spectral traces for hydrazone formation between o-sulfobenzaldehyde and (top—Compound 308) MeONA$^3$ or (bottom) MeOPH, demonstrating the instability of the MeOPH-derived hydrazone. All reactions were performed in 1×PBS at 37° C. These data affirm that the acid functional group feature of Compound 308 contributes to effective kinetics of the method in forming a detectable and stable product. In the lower panel where the acid group is absent in the product formed.

Figure 17:
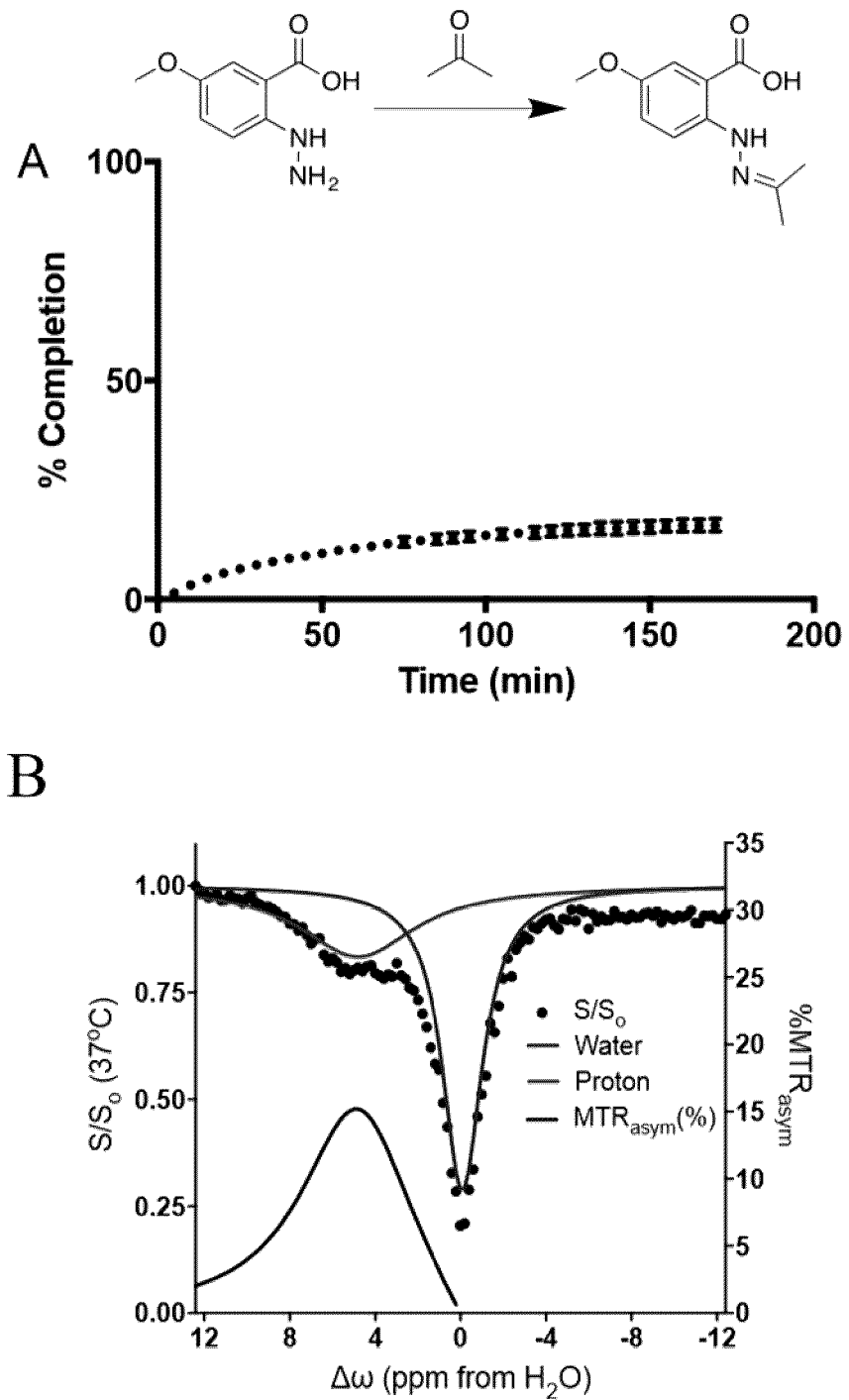
FIG. 17 shows hydrazone UV-Vis spectral traces (Panel A) and z-spectra (Panel B) for hydrazone formation for Compound 318.

FIG. 17 shows hydrazone UV-Vis spectral traces for hydrazone formation between o-sulfobenzaldehyde and (top—Compound 318) MeONA³ or (bottom) MeOPH, demonstrating the relative instability of the MeOPH-derived hydrazone. All reactions were performed in 1×PBS at 37° C.

Table 1 shows the calculated rates of reaction under pseudo-first order conditions in 1×PBS at 37° C. for hydrazine formation from hydrazine and different carbonyls, as indicated.

TABLE 1

Calculated Rates of Reaction

| Hydrazine | Carbonyl | $k_{obs}$ (min$^{-1}$) |
|---|---|---|
| MeONA³ | Acetaldehyde | 0.012 ± 0.001 |
| | o-sulfobenzaldehyde | 0.112 ± 0.03 |
| | Acetone | 0.017 ± 0.0004 |
| MeOPH | Acetaldehyde | n.d. |
| | o-sulfobenzaldehyde | 0.119 ± 0.02 |
| MeEster | o-sulfobenzaldehyde | $8.0 \times 10^{-4} \pm 5.5 \times 10^{-5}$ |

Figure 18:
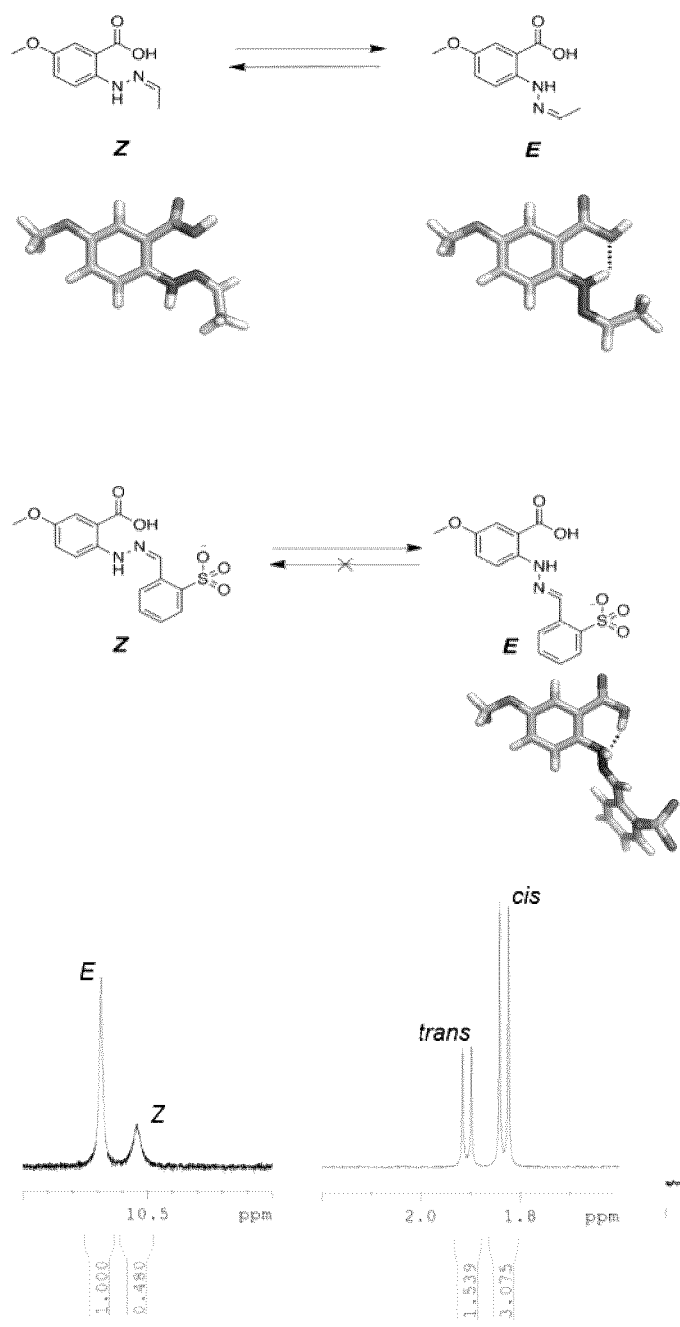
FIG. 18 shows that intramolecular hydrogen bonding favours the E-conformation (cis) of hydrazones formed from MeONA$^3$ hydrazines, versus Z-conformation (trans).

FIG. 18 shows that the intramolecular hydrogen bonding favours the E-conformation (cis) of hydrazones formed from MeONA³ hydrazines. Structural optimization was performed using an RB3LYP routine in water as implemented by WebMO, resulting in the conformations shown (upper Compounds 301-Z and 301-E). Putative hydrogen bond is shown by a dashed black line. The predicted preference for E-conformation (cis) was confirmed by ¹H-NMR (lower Compounds 308-Z and 301-E). The preference for the cis conformation of the acetaldehyde moiety was also confirmed by ¹H-NMR (values shown are E=1.000, Z=0.480; trans=1.539, cis=3.075; E=0.943, respectively). These data show that conformation may have an impact on imaging and binding, where in instances it may be that E (or cis) configuration of compounds of Formula A is preferred for binding or purification.

Figure 19:
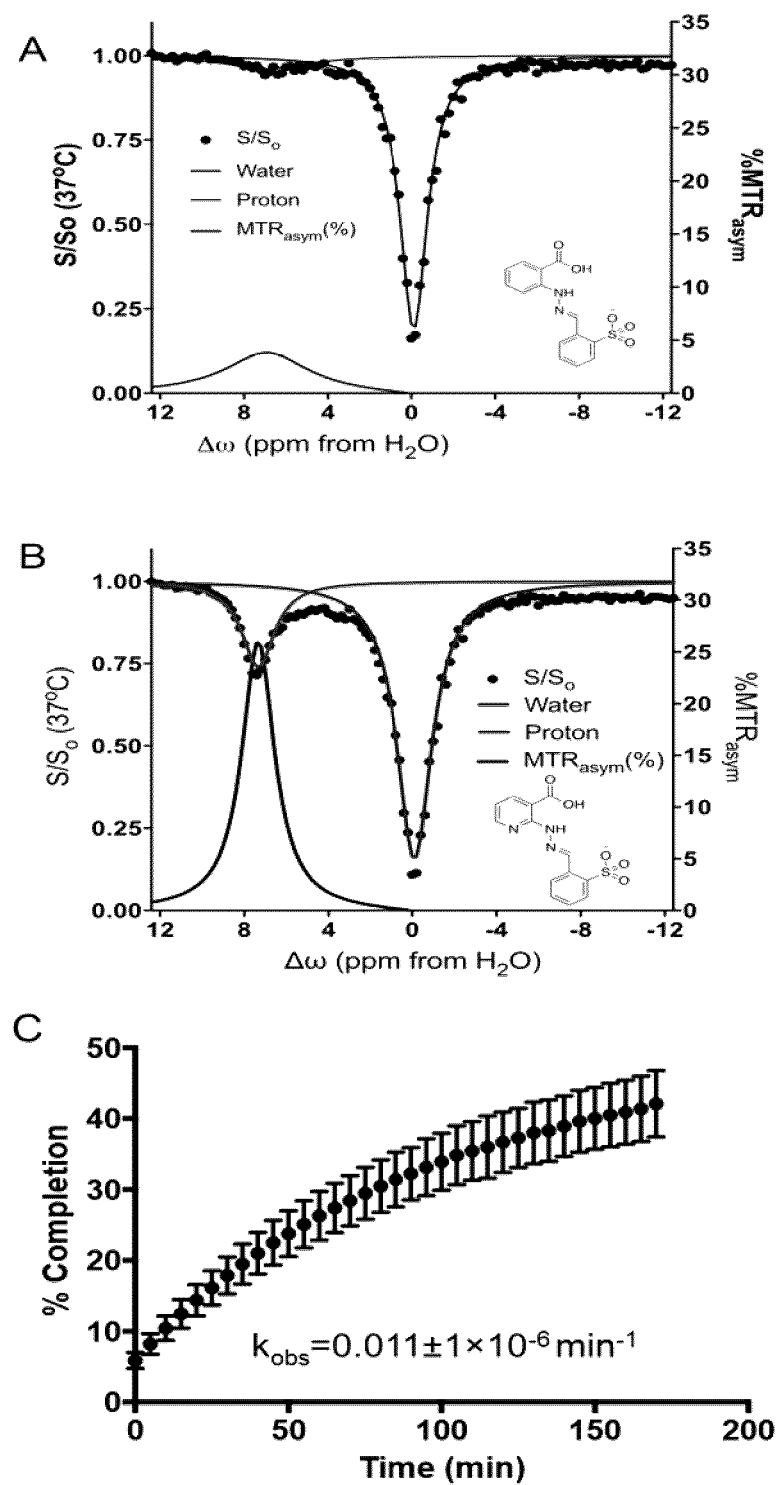
FIG. 19 illustrates that the CEST signal increases dramatically with substitution of the benzyl ring of N-amino anthranilic acid by a pyridine ring.

FIG. 19 illustrates that the CEST signal increases dramatically with substitution of the benzyl ring of N-amino anthranilic acid by a pyridine ring. Panel A shows the Z-spectrum of the hydrazone formed with N-amino anthranilic acid and o-sulfobenzaldehyde, showing ~5% CEST signal production (Compound 306). Panel B shows the substitution of the pyridine ring enhances CEST signal of the same hydrazone to ~25% (Compound 319). Panel C shows the rate of hydrazone formation with the pyridine-based o-acid hydrazine is significantly slower than the benzyl analog, but show good product stability.

Figure 20:
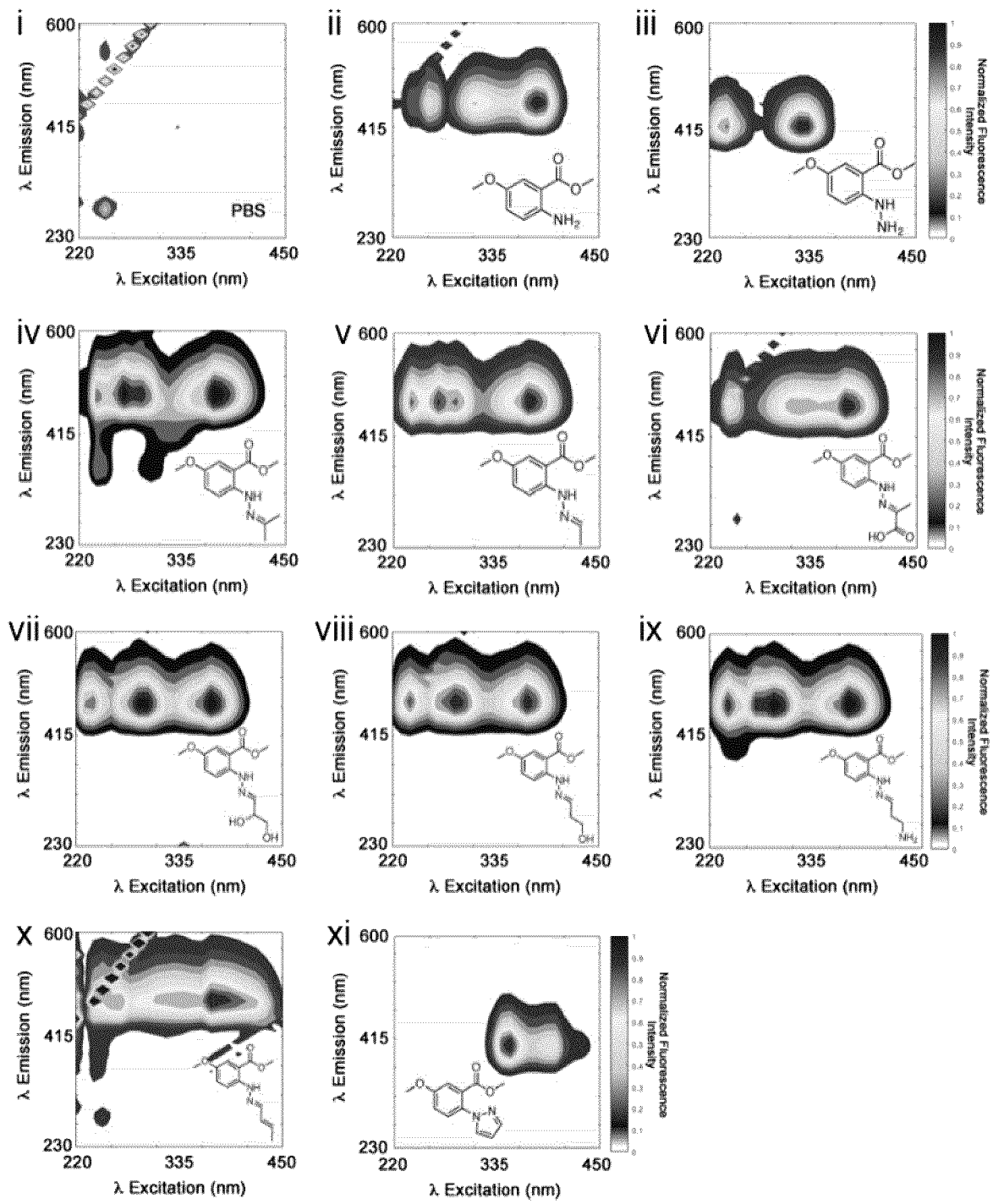
FIG. 20 shows fluorescent excitation-emission matrices for biologically relevant hydrazones, showing spectral fingerprints unique to the reacted carbonyl.

FIG. 20 shows fluorescent excitation-emission matrices for biologically relevant hydrazones, showing spectral fingerprints unique to the reacted carbonyl. Spectra are for (i) PBS, (ii) methoxy anthranilic acid ester, (iii) methoxy N-amino anthranilic acid ester, and hydrazones formed from methoxy N-anthranilic acid ester and (iv) acetone, forming Compound 320; (v) acetaldehyde, forming Compound 312; (vi) pyruvate, forming Compound 322; (vii) DL-glyceraldehyde, forming Compound 323; (viii) glycolaldehyde, forming Compound 324; (ix) 3-aminopropanal, forming Compound 325; (x) crotonaldehyde, forming Compound 326; (xi) malondialdehyde, an aldehyde indicative of cell death, forming Compound 327.

Figure 21:
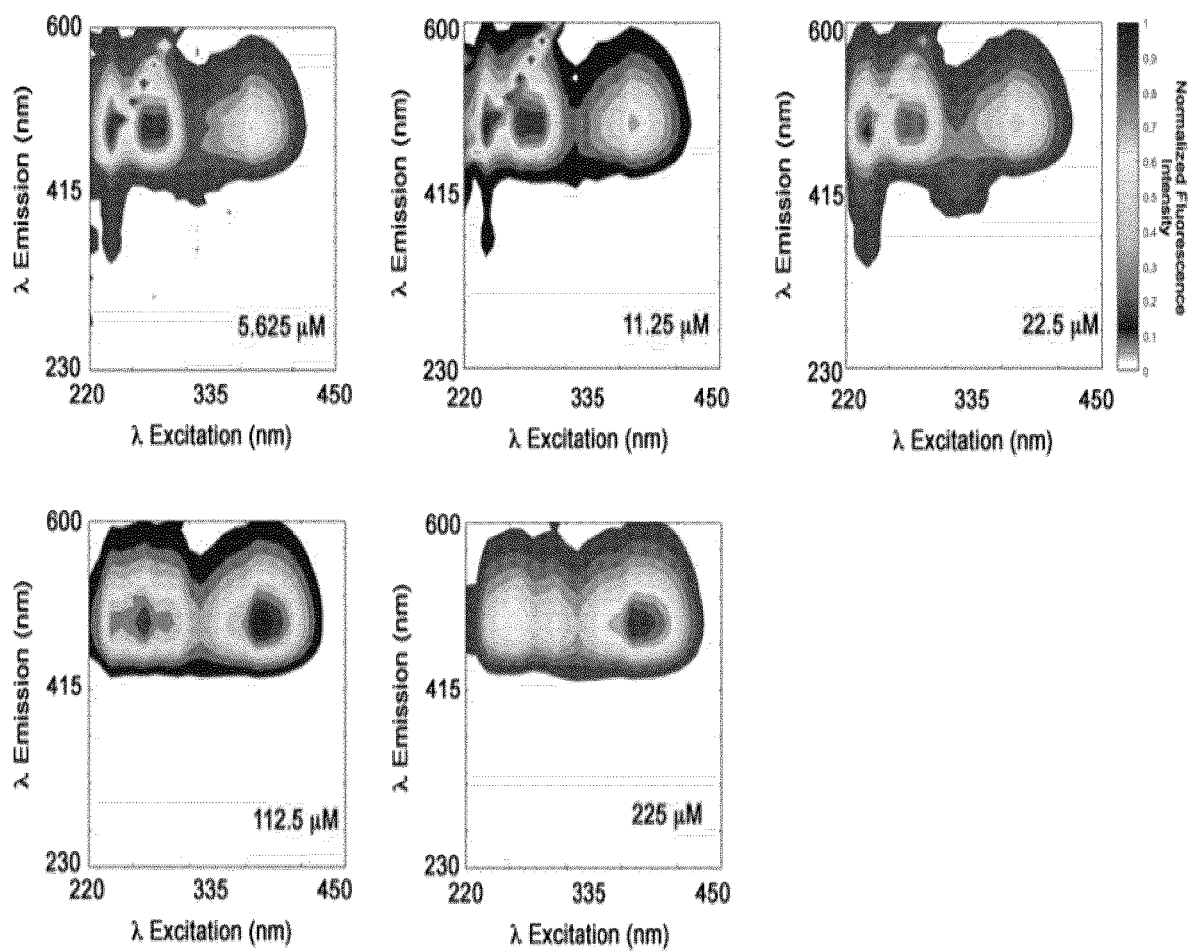
FIG. 21 shows the effect of hydrazine concentration on the excitation-emission matrix fluorescent fingerprint.

FIG. 21 shows the effect of hydrazine concentration on the excitation-emission matrix fluorescent fingerprint. The hydrazine of acetone and methoxy N-amino anthranilic acid ester was dissolved in PBS to the concentration indicated on the plots (5.625 to 225 µM), and excitation-emission matrix was acquired. At pathologically relevant concentrations (up to 22.5 µM) there is little change to the fluorescent fingerprint.

Figure 22:
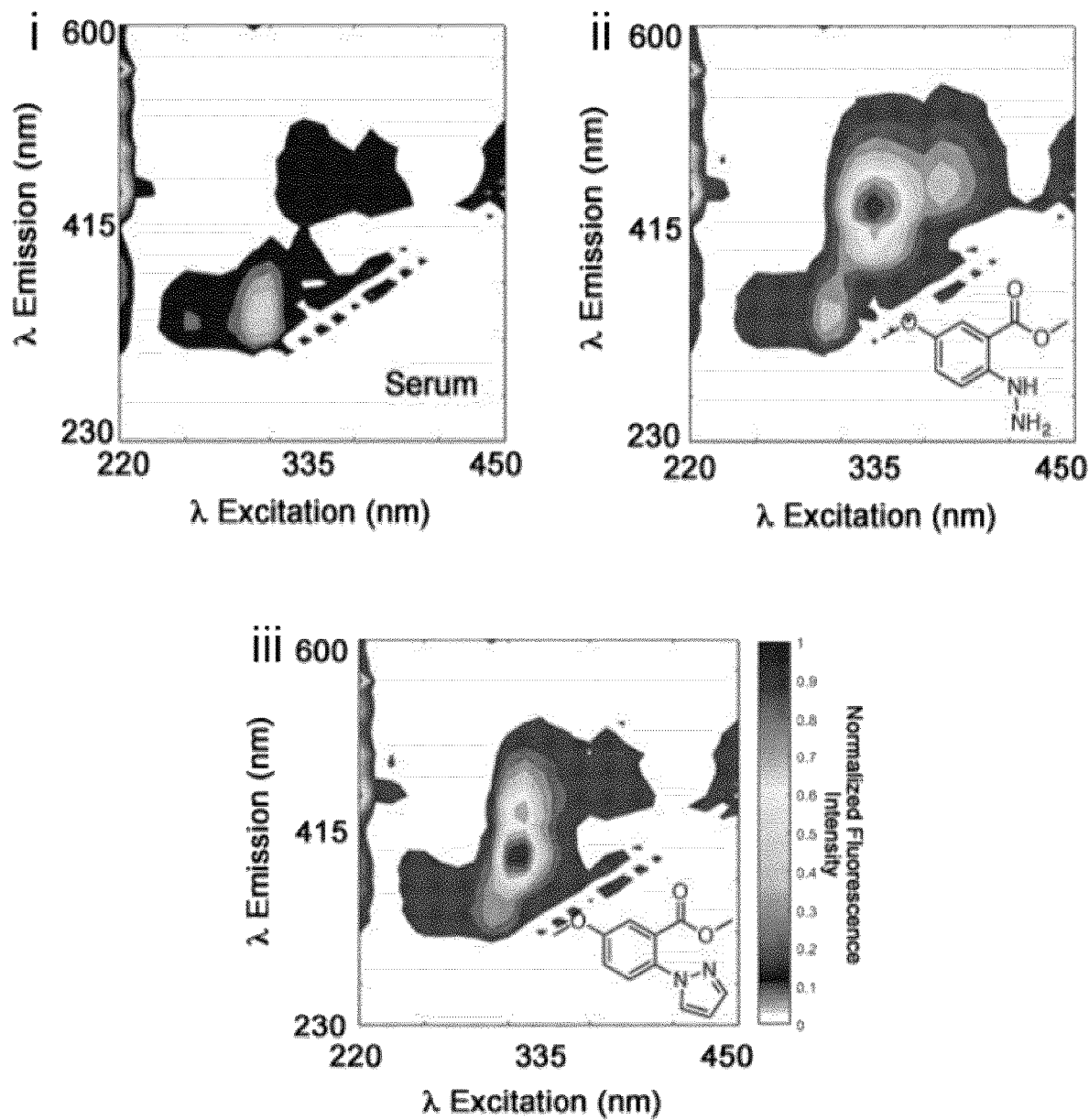
FIG. 22 shows fluorescent excitation-emission matrices for probe species in whole mouse serum.

FIG. 22 shows fluorescent excitation-emission matrices for probe species in whole mouse serum. Spectra are for (i) mouse serum, (ii) methoxy N-amino anthranilic acid ester, and (iii) hydrazone formed from malondialdehyde (Compound 327).

EXAMPLES

Example 1

Preparation of Compounds of Formula I and Use of CEST-MRI Probes for Detection of Biologically Relevant Aldehydes.

Aldehydes such as acetaldehyde, malondialdehyde, and 2-aminopropanal, are toxic stress molecules that can be elevated in disease. Elevated concentrations of endogenous aldehydes have been shown during tumour progression, and following a spectrum of brain injuries. Due to their limited existence, it remains a challenge to find a method capable of mapping aldehydes in vivo, despite great potential to be important diagnostic and prognostic biomarkers of a range of diseases. A small library of molecular probes according to Formula I, for non-invasive in vivo imaging of aldehydes has been developed. The rapid reaction between various 2-hydrazinobenzoic acids and aldehydes (both aliphatic and aromatic) results in corresponding hydrazones which possess exchangeable protons with rates well suited for Chemical Exchange Saturation Transfer Magnetic Resonance Imaging (CEST-MRI).

While 2-hydrazinobenzoic acids were found to be CEST silent (no signal), some of the hydrazones possessed strong CEST signal. Chemical synthesis of CEST molecular probes and in vitro characterization of their CEST MRI properties is described. See FIG. 6, Panel B.

A general description of one possible synthetic procedure for preparation of compounds of Formula I, with 5-methoxyhydrazine is as follows.

A solution of sodium nitrite ($NaNO_2$, 152 mg, 2.2 mmol) in water (0.8 mL) was cooled to about 3° C. and was added (dropwise over a 1 min period) to a vigorously stirred suspension of 5-methoxyanthranilic acid (334 mg, 2 mmol) in 6 M hydrochloric acid (HCl, 4.8 mL) cooled to 3° C. (ice bath). The mixture was stirred for 1 h at 3° C., followed by the addition of a solution of tin(II)chloride dihydrate ($SnCl_2.2H_2O$, 908 mg, 4 mmol) in 6 M hydrochloric acid (HCl, 1.2 mL). The mixture was stirred for additional 20 min at 3° C. The formed precipitate was filtered off with suction, was washed with ice-cold water and was dried to afford 5-methoxy-2-hydrazinobenzoic acid dihydrochloride (526 mg) contaminated with tin salts. To remove the tin salts, the solid was resuspended in 1 M hydrochloric acid (HCl, 25 mL), followed by stirring for 48 hours at room temperature. The solid was filtered off with suction, was washed with ice-cold water and was dried to produce tin-free 5-methoxy-2-hydrazinobenzoic acid dihydrochloride (237 mg, 46% yield).

Example 2

Compounds of Formula I for Detecting Aldehydes Indicative of Brain Injury Due to Concussion and/or for Neutralizing Reactive Aldehydes Resulting from Concussion It is important to identifying and treat concussions, for example for concussions resulting from contact sport. A protocol to positively identify a concussion is prerequisite to seeking treatment. Compounds of Formula I may be used for detecting carbonyls such as aldehydes that are indicative of a concussion. Further, compounds of Formula I may be used for neutralizing reactive aldehydes that increase in concussion. Aldehydes formed as a result of oxidative stress due to concussion may be referred to herein as "aldehyde load". Neutralization of aldehydes formed as a result of brain injuries such as concussion, could also reduce downstream damage attributable to an increase in aldehyde load for a concussed subject.

Reactive aldehydes may covalently modify proteins, nucleic acids, lipids, and carbohydrates and activate apoptotic pathways. Detection of such aldehydes may serve as an important step not only in identifying concussion, but also in treating concussion due to a possible neuroprotective effect of neutralization.

Compounds of Formula I, may be used to detect aldehydes formed from brain injury due to concussion. Further, compounds of Formula I may be used to neutralize the reactive aldehydes so formed, thereby treating or limiting damage that can occur due to the presence of the reactive aldehydes in vitro.

Example 3

Compounds of Formula I for Detecting Aldehydes Indicative of Neurodegeneration or for Neutralizing Reactive Aldehydes in Neurodegenerative Diseases Such as Alzheimer's Disease.

Compounds of Formula I may be used for detecting carbonyls present on aldehydes that are indicative of neurodegeneration. Further, compounds of Formula I may be used for neutralizing reactive aldehydes that increase in certain physiological conditions such as neurodegenerative diseases like Alzheimer's disease. Neutralization of aldehydes formed as a result of neurodegeneration, could also reduce damage occurring as a result of the neurodegenerative condition.

Oxidative stress occurs in neurodegenerative processes. Aldehydes formed as a result of oxidative stress, or "aldehyde load" may react in vitro to covalently modify proteins, nucleic acids, lipids, and carbohydrates and/or activate apoptotic pathways. Detection of such aldehydes may serve as an important step in diagnosing neurodegeneration or neurological damage. Neutralization of reactive aldehydes may be neuroprotective. Hydroxylamines, such as N-benzylhydroxylamine, were assessed for a protective effect against aldehyde neurotoxicity by Wood et al., (2006). N-benzylhydroxylamine was assessed in a trimethyltin (TMT) rat model of hippocampal CA3 neurodegeneration, and found that reactive aldehydes compromised mitochondrial integrity but that N-benzylhydroxylamine provided protection against neurodegeneration.

Compounds of Formula I, described herein, may be used to detect aldehydes formed from neurodegeneration or neurological damage. Further, compounds of Formula I may be used to neutralize reactive aldehydes formed as a result of the neurodegenerative process, in the interests of treating the condition and limiting damage that can occur due to the presence of the reactive aldehydes in vitro.

Example 4

Compounds of Formula I for Imaging Transient Effectors Containing Aldehyde Groups, and for Detecting Aldehydes Indicative of Effective Chemotherapy Life at the molecular level is not static, but involves coordinated, and continuously adaptive, sub-cellular events driven by biomolecules. These biomolecules range from large enzymes to reactive small molecules, all of which exert an effect on the cell to alter its function. Indeed, the over- or under-activity of biomolecules can result in disease or injury, or in an intended response to applied therapy (e.g. DNA damage or tumor cell death). A biomolecule may be a part of a network within which any single sub-cellular target is only transiently active or transiently present, often rapidly giving way to its successor in a signaling chain. This transiency often makes these biomolecules elusive to analysis by traditional methods in the context of the living organism. However, measuring the activity of these molecules while overcoming the difficulty of target transiency can enable personalized medicine, including the detection of disease prior to outward signs and symptoms, and the assessment of therapy prior to disease progression. Molecular imaging of a target biomolecule using non-invasive methods in living subjects is desirable, and would allow interrogation of transient sub-cellular functions of fundamental importance. Probes used to measure endogenous aldehydes for cancer imaging or staging utilizing a metal-free MRI technique called Chemical Exchange Saturation Transfer imaging. One goal of the use of these probes is to provide access to information about the dysregulation of molecular activity that underlies disease through non-invasive, quantitative, and clinically accessible imaging techniques.

Probes which are compounds according to Formula I, described above, can be used to evaluate efficacy of chemotherapy.

Serum oxidative stress markers were found in patients undergoing chemotherapy as a breast cancer treatment, resulting in an increase in genotoxic damage. Gomez Junior et al. (2015) evaluated oxidative parameters of erythrocytes and genotoxicity in leukocytes of patients with breast cancer undergoing chemotherapy. In that study, oxidative parameters were detected by spectrophotometry and genotoxic damage by single cell gel electrophoresis in women with breast cancer, before chemotherapy and after the second and fourth cycles of therapy with cyclophosphamide and doxorubicin. After the fourth cycle of chemotherapy an increase in reactive aldehyde-containing substances was observed, compared with healthy women group and baseline levels. Patients with breast cancer presented an indication of oxidative stress before, during, and after chemotherapy, demonstrating that aldehyde detection may be used as a marker of efficacy of chemotherapy in killing tumour cells. However, previous methods for evaluating carbonyl groups such as aldehydes had limitations.

Compounds of Formula I, described herein, may thus be used to detect aldehydes formed as a result of cancer chemotherapy, as tumour cells die. This may be used as a clinical indicator of treatment efficacy. Further, compounds of Formula I may be used not only to detect, but also to neutralize reactive aldehydes formed as a result of cancer chemotherapy, thus curtailing some of the downstream damage that may be attributable to these reactive species in an already immunocompromised cancer chemotherapy patient. The use of these probes permits evaluation of activity of biomolecular pathways, rather than primarily the expression of the biomolecules involved in the activity.

Example 5

Use of Hydrazines, Such as Methyl-5-Methoxyanthranilate-Based Fluorophores, for Identification of Biologically Relevant Aldehyde Compounds in Body Fluids Through Fluorescence The use of hydrazine containing compounds, such as methyl-5-methoxyanthranilate-based fluorophores, for the identification of aldehyde carbonyl groups present on biologically relevant compounds in body fluids is described herein. Although the presence of small carbonyl compounds (e. g. acetaldehyde, 2-aminopropanal, malondialdehyde, acetone) in blood and urine is a valuable predictor of diseases such as cancer, atherosclerosis, diabetes, or concussion, the detection and identification of such molecules remains challenging. Towards this end the fluorescence associated with methyl 5-methoxyanthranilate, a hydrazine, was exploited. Spectral features of the compound are exquisitely sensitive to the hydrazine product of their condensation with endogenous aldehydes and ketones.

Figure 23:
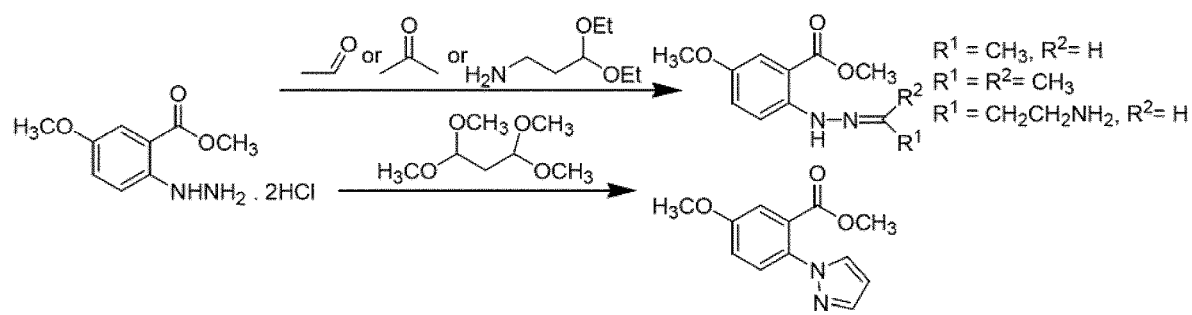
FIG. 23 shows a scheme for formation of fluorescently detectable hydrazones/heterocycles derived from related fluorescently silent hydrazine.

FIG. 23 shows a scheme for formation of fluorescently detectable hydrazones/heterocycles derived from related fluorescently silent hydrazine, as prepared by reaction with various endogenous carbonyl compounds or their synthetic equivalents. The lower reaction proceeds to Compound 327. Detailed evaluation of the fluorescence properties associated with these hydrazones/heterocycles has been carried out, implying the suitability of the methyl 5-methoxyanthranilate-derived hydrazine for the detection of small aldehyde compounds in blood and urine. Excitation-emission matrix (EEM) spectroscopy resulted in unique pattern associated with each of the carbonyl-containing compounds in the library. Detection of carbonyl-containing compounds in the blood, such as aldehydes, and/or other body fluids is made possible using these compounds, N-amino anthranilate (a hydrazine), in reactions and detecting the resulting fluorescence upon hydrazine formation.

Example 6

Fluorescence Fingerprinting of Aldehydes for Blood-based Detection of Disease & Injury.

The production of aldehydes occurs in disease and injury. Lipid peroxidation, the autocatalytic breakdown of biomembranes during disease, produced a variety of endogenous aldehydes, such as:

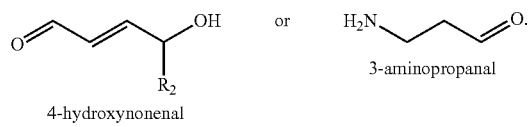

Additionally, tissue injury such as brain injury, can result in polyamine catabolism to aldehyde products. Aldehyde levels can be elevated in cancer, atherosclerosis, and concussion, among other inflammatory diseases, and may be early biomarkers predictive of disease outcome.

N-Amino anthranilic esters can be fast-reacting aldehyde sensors. N-amino anthranilate methyl ester reacts rapidly with endogenous reactive aldehydes. The reaction of 5-methoxy-N-amino anthranilate methyl ester (1) with a reactive aldehyde results in the formation of hydrazine (2) in PBS at room temperature is shown:

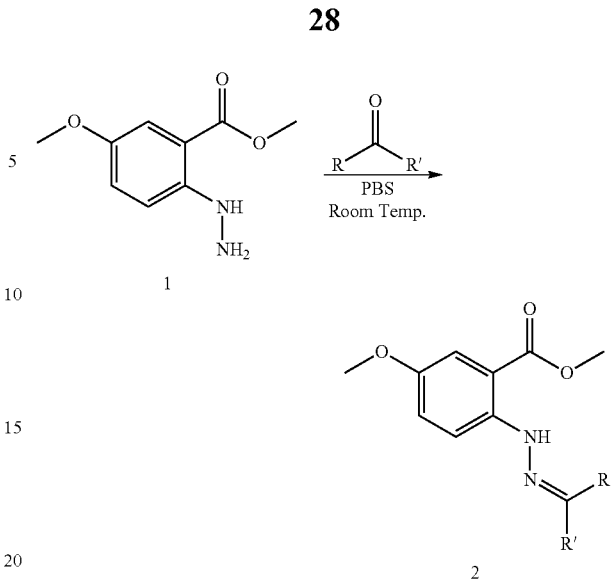

The formation of the acetaldehyde-derived hydrazone is demonstrated through time-lapse imaging, with hydrazone formation within 1 second of aldehyde addition to a PBS solution of 1.

N-amino anthranilic acids can act as specific sensors for malondialdehyde. N-amino anthranilic acid reacts rapidly with MDA to form a fluorescent pyrazole. A proposed 2-step reaction scheme for the formation of the MDA-derived pyrazole (5) from 5-methoxy-N-amino anthranilic acid (3) is shown:

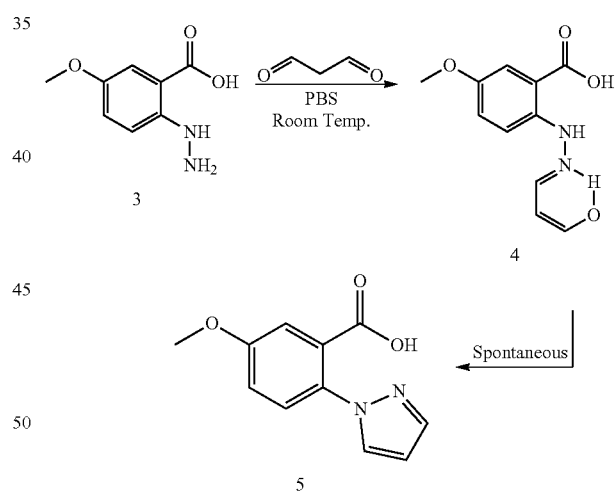

Emission spectra of the probe (3), shows the short-lived hydrazone (4), and the pyrazole product (5). Fluorimetric monitoring of the trapping of MDA by the N-amino anthranilic acid probe shows that a rapid conversion to form fluorescent pyrazole is observed over 10 min at room temperature.

Figure 24:
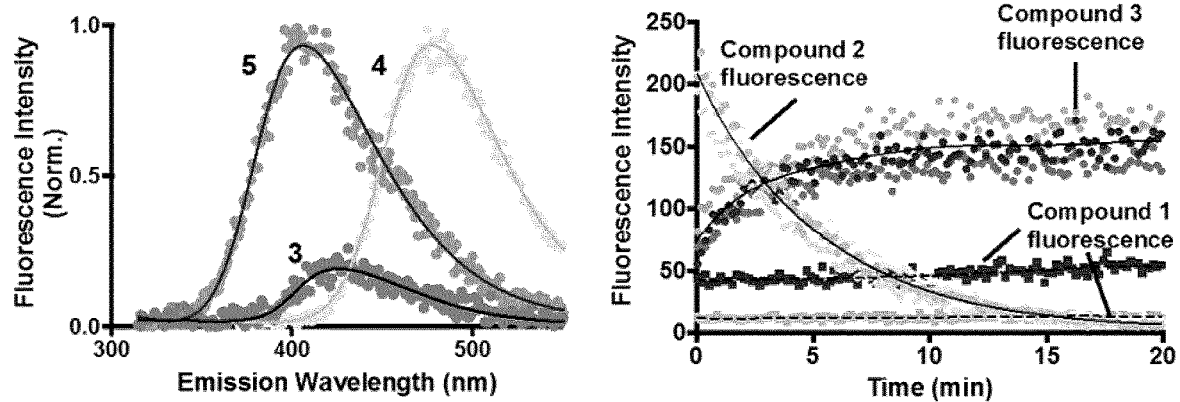
FIG. 24 shows N-amino anthranilic acids can serve as sensors for malondialdehyde (MDA) based on fluorescent intensity (Panel A), and demonstrating rapid reaction over 10 minutes (Panel B).
Figure 24:
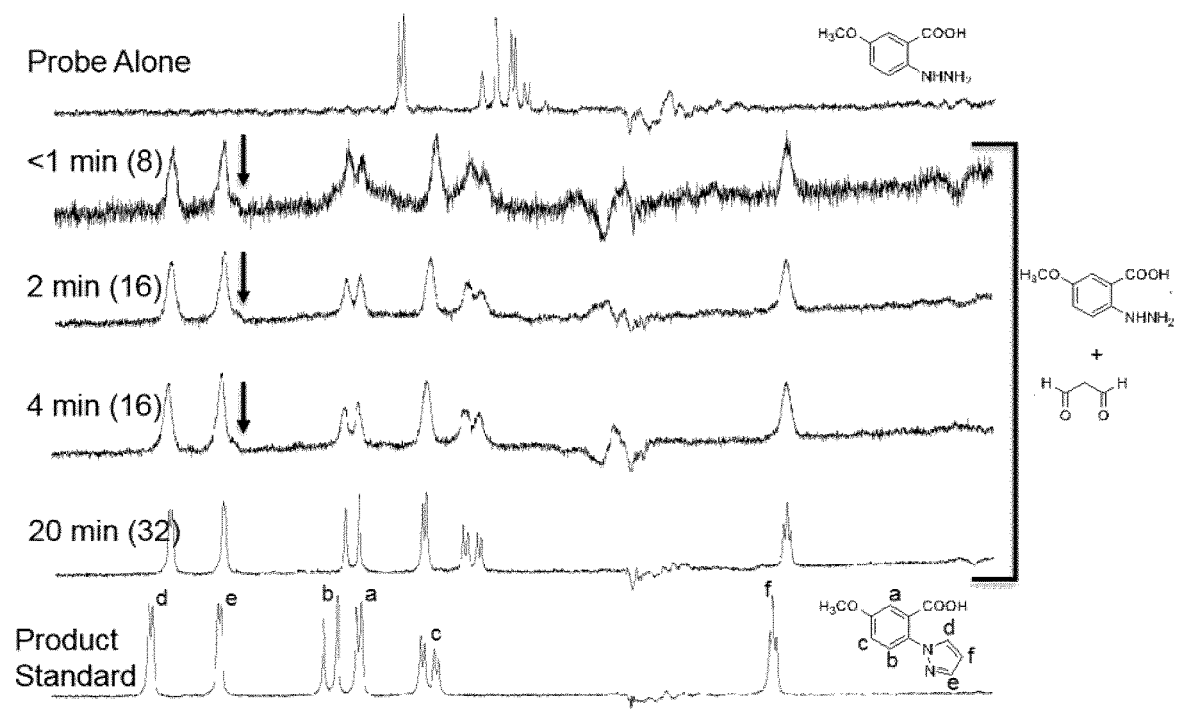

FIG. 24 illustrates that N-amino anthranilic acids can serve as sensors for malondialdehyde (MDA) based on fluorescent intensity (Panel A), and demonstrating rapid reaction over 10 minutes (Panel B). The formation of the MDA-derived pyrazole ring was monitored by $^1$H-NMR. Hydrazone (4) formation happens within less than 1 min of incubation of the NA$^3$ acid probe and MDA. The pyrazole product (5) forms rapidly as well, and reaches completion within 20 min. The fluorescence 'turn-on' of the N-amino anthranilic acid probe is specific for MDA. Fluorescence emission spectra shows the N-amino anthranilic acid probe alone, or for the hydrazone products formed from incubation with ubiquitous carbonyl metabolites glyceraldehyde, pyruvate, or reactive aldehydes derived from cell stress: MDA (greatest fluorescence intensity), crotonaldehyde, or glyoxal.

Excitation-Emission Matrices (EEM) for spectral fingerprinting of hydrazones were evaluated as in previous Examples, by acquiring an emission spectrum at every 10 nm of excitation wavelength. The UV (360 nm) excitation images and EEM excitation images were evaluated for endogenous reactive aldehydes, similar to those described above in regard to FIG. 20. Fluorescent fingerprinting of MDA was conducted in serum, and EEM images were plotted for whole mouse serum, probe alone in whole serum, and the MDA-derived hydrazone in whole serum, similar to results shown above in regard to FIG. 22. There were significant spectral differences seen upon hydrazone formation, supporting the utility of fluorescent fingerprinting of endogenous reactive aldehydes as blood-based biomarkers of disease and injury.

Figure 25:
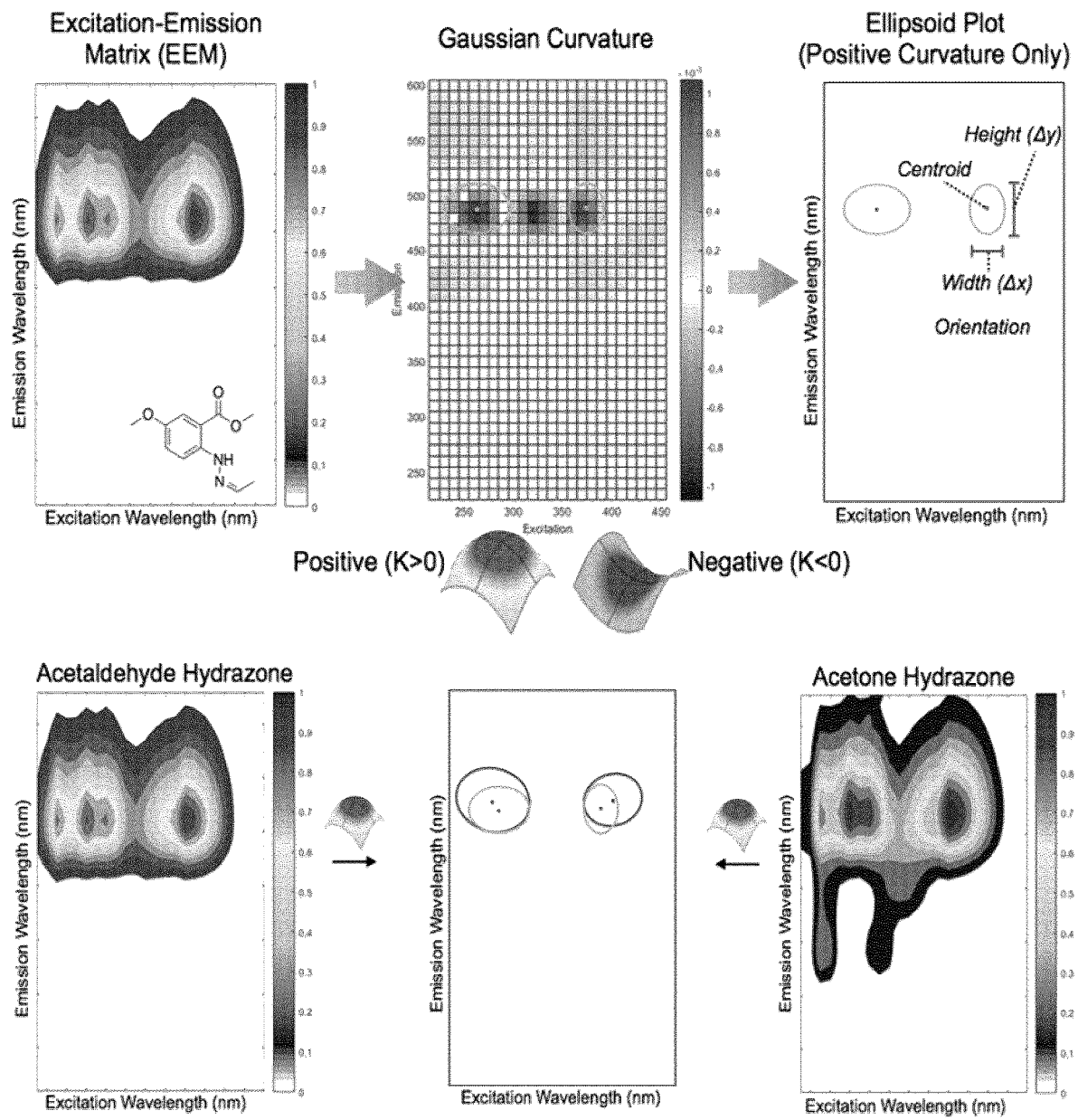
FIG. 25 shows an example of how excitation-emission matrices may be re-defined using maps of Gaussian curvature for aldehyde identification by EEM fingerprint recognition.

FIG. 25 illustrates how aldehyde identification may be conducted by EEM Fingerprint Recognition. As shown, the EEM can be redefined through differential geometry into maps of Gaussian curvature, converting spectral information to positive, neutral, or negative curvature values. Ellipsoids can then be extracted from the Gaussian surfaces, objectively quantifying the position, magnitude, and character of spectroscopic features from the EEM. Ellipsoids can be precisely defined geometrically, simplifying pattern recognition. Utilizing a simple anthranilic acid-based scaffold, a rapid and simple method can be employed for reactive aldehyde derivatization and identification. The methodology described does not require the use of complex analytical instrumentation (e. g. mass spectrometer) and is amenable to point-of-care implementation even in a modest clinical setting.

Example 7

Electrochemical Detection Method.

The following example describes a method for detection of aldehydes using a compound of Formula 1, employing an electrochemical detection method. Starting with pre-fabricated Si/SiO$_2$ chips (either with gold contacts or with no contacts), each chip is washed with water, acetone, methanol. The chip is plasma treated for about 15 mins to remove any solvent left over from the washing step. Chips are treated in a solution of 1% OTS (octadecyltrichlorosilane) with toluene solution (about 1 h at 70° C.) which forms a mono-layer which lets the next coat adhere uniformly.

The chip is baked for about 1 h at 70° C. to finish assembling the OTS mono-layer. The chip is washed with toluene, water (which activates the OTS layer). Silver contacts may be stamped onto the chip if there are no contacts. Subsequently, the chip is coated with the organic semi conducting layer, for example, CuPc (copper phthalocyanine) and/or fluorinated CuPc may be used. This may be done either by surface treatment (pipetting a volume on the top of the chip) or by deposition in the Angstrom machine. When doing the latter a micron thick layer (for example 150 micron) can be uniformly deposited, which may take a few hours. The chip can then be tested.

To test, a probe is connected to each contact (for example, 16/chip may be used in which 4 of each length is employed, as described below). Current is applied through the chip as well as across the gate. The chips may be kept at 25° C. throughout testing. The current is then swept through different voltages and mobility, voltage threshold, and on/off ratios are calculated. This may be repeated as desired, for example 5× per contact, to establish a baseline. After baselining a chip, an analyte is then deposited in solution on top, subsequently allowing the solvent to dry. Testing is then repeated, but now with analyte on top of the semiconducting layer.

On the chip, a number of small gold squares represent the contacts. The area where current flows through the semiconductor is between the lines present between the contacts. The distances used may be, for example, 5 µm, 10 µm, and 20 µm. On some prefab chips, there is the option to use smaller distances, such as for example a 2.5 µm distance. The chip so formed may be exposed to samples suspected of containing the subject aldehyde and electrochemical detection can be determined.

Example 8

Click Chemistry Reactions

The compounds described herein or the products formed upon reaction with aldehydes may be modified for detection by the addition of a click chemistry group, such as a BF3 azide. There are different types of click reactions, including 1) copper-catalyzed azide-alkyne cycloaddition; 2) strain-promoted azide-alkyne cycloaddition; 3) strain-promoted alkyne-nitrone cycloaddition; and 4) strained alkene additions, including azide [3+2]cycloadditions, tetrazine inverse-demand Diels-Alder, and tetrazole photoclick reactions.

The following compound is a BF3 azide click chemistry product which may be used in functionalizing the compounds or products described in the methods for detection of aldehydes described herein.

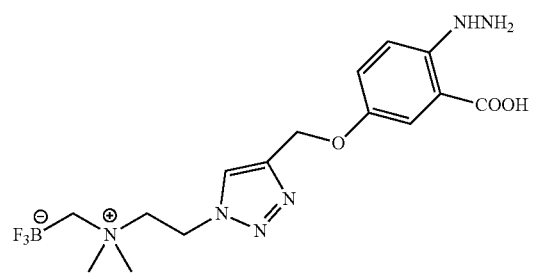

Example 9

Hydrazo-CEST: Hydrazone-Dependent Chemical Exchange Saturation Transfer Magnetic Resonance Imaging of Aldehydes In this example, the rapid formation of hydrazones under physiological conditions was exploited for the detection of aldehydes through chemical exchange saturation transfer magnetic resonance imaging (CEST-MRI). A metal-free, diamagnetic contrast agent derived from N-amino anthranilic acid was introduced, which selectively 'turned-on' to produce substantial contrast enhancement upon hydrazone formation through an effect termed Hydrazo-CEST. While the hydrazine form of the probe produced no CEST-MRI signal enhancement, the formation of the aryl hydrazone resulted in >20% intensity decrease in the bulk water signal through the CEST effect, as measured by 300 MHz $^1$HN MR, 3 T and 7 T MRI. Both the electronic contributions of the N-amino anthranilate and the aldehyde binding partner were shown to directly impact the exchange rate of the proton on the ring-proximal nitrogen, and thus the imaging signal. Additionally, the presence of the carboxylic acid moiety ortho to the hydrazine was necessary not only for contrast production, but also for rapid hydrazone formation and prolonged hydrazone product stability under physiological conditions. This work provided the first example of an MRI-based contrast agent capable of a 'turn on' response upon reaction with bioactive aldehydes, and outlined both the structural and electronic requirements to expand on Hydrazo-CEST, a hydrazone-dependent subtype of diamagnetic CEST-MRI.

Introduction

Magnetic resonance imaging (MRI) is a clinical diagnostic technique reliant upon the mapping of differential water proton relaxation following radiofrequency excitation in a magnetic field. MRI has traditionally been applied to anatomical and functional imaging in the clinical setting, and has been moving toward molecular-level diagnosis in part through the use of biochemical-targeted contrast agents. Gadolinium-based chelates that reduce the relaxation time of neighboring water protons have previously been the focus of contrast agent development, however concerns about chelate stability in vivo has motivated a search for metal-free alternatives. Chemical Exchange Saturation Transfer (CEST) using organic (i.e. diamagnetic) probes is a metal-free MRI technique offering a promising alternative mode of molecular-level contrast that can overcome the toxicity concerns associated with paramagnetic agents.

FIG. 4, as described above, shows a mechanism of Chemical Exchange Saturation Transfer (CEST) MRI. (a) An exchangeable proton (white circle) on the CEST contrast agent (hexagon) has a chemical shift that is different from that of water. This chemical shift difference ($\Delta\omega$) allows the exchangeable proton on the contrast agent to be selectively spin saturated, effectively making it invisible to detection by MRI. (b) Once spin saturated, the contrast agent proton (circles) undergoes exchange with water protons, making water invisible to the MRI (signal peak at $S_o$ versus that as $S+\Delta\omega$). The signal intensity (% CEST) is calculated as the signal ratio with and without contrast agent proton spin saturation.

The CEST imaging mechanism depends on a contrast agent proton that readily exchanges with water, and that possesses a sufficiently large resonance frequency offset from water (>2 ppm) to allow its specific spin saturation by radiofrequency irradiation (see FIG. 4, Panel A). A spin saturation effectively masks the exchangeable proton from detection, reducing the post-saturation intensity of the water peak (S) relative to its pre-saturation magnitude ($S_o$) (see FIG. 4, Panel B). Ultimately, the suppression of water signal results in a loss of image contrast (i.e. a darkening) in the immediate vicinity of the contrast agent. Since solute-water proton exchange rates ($k_{sw}$) for the CEST effect are typically 102-103 Hz, a few seconds of irradiation can significantly amplify the signal produced from a single contrast agent molecule.

Humans are exposed to toxic aldehydes on a daily basis, both externally through the environment (e. g. acrolein, formaldehyde) and internally through highly regulated metabolic processes (e. g. acetaldehyde, 3-aminopropanal). Dysregulation of these metabolic processes, including lipid peroxidation, carbohydrate autoxidation, polyamine oxidation, and myeloperoxidase activity, leads to an increased production of aldehydes during chemical or mechanical stress, and throughout the course of a range of diseases. Aldehydes have been suggested to be valuable biomarkers of brain damage, ischemia-reperfusion injury, and neurodegenerative disorders, but their detection in vivo is challenging. Endogenous aldehydes are not usually protein-bound, but rather are small (MW<100), mobile and reactive molecules; consequently, in vivo detection of endogenous aldehydes is not amenable to a 'probe retention'-based imaging mechanism. Within the context of development of advanced probes for molecular imaging, this Example builds on the value of aldehydes as diagnostic biomarkers and as molecular probes designed for and capable of the in vivo imaging of these small, unbound aldehydes. Two key design criteria were established: (1) the probe must react rapidly with endogenous aldehydes to form stable products; (2) a significant signal enhancement should be observed upon reaction of the molecular imaging probe with the aldehydes. To comply with both requirements, molecular probes were investigated based on the N-amino anthranilic acid (2-hydrazinobenzoic acid) scaffold. Structurally similar hydrazines have been recently shown to react with aldehydes in "click-like" fashion, with a reaction rate>2 $M^{-1}s^{-1}$ that is comparable to that associated with strain-promoted alkyne-azide cycloaddition (Kool et al., 2013).

Moreover somewhat structurally related N-substituted (N-phenyl, N-mesyl, N-trifluoroacetyl) anthranilic acids are known to act as diamagnetic CEST MRI contrast agents. By detailed investigation of a small library of N-amino anthranilic acids and corresponding hydrazones, the functionalities available for metal-free contrast agent design have been expanded. It is herein demonstrated that the proton on the ring-proximal nitrogen of an aryl hydrazone is amenable to detection by CEST-MRI.

FIG. 5, discussed above, schematically illustrates Hydrazo-CEST as a mechanism of MRI contrast enhancement, with signal production selectively turned on in the presence of bioactive carbonyls (e.g. aldehydes and ketones). The exchangeable hydrazo proton does not result in the suppression of water signal when the contrast agent, based on substituted N-amino anthranilic acids, is in the hydrazine form (i.e. k's, is not amenable to CEST-MRI). The rapid condensation of the hydrazine with the aldehyde or ketone to form a hydrazone results in an optimized exchange of the spin saturated proton with water, significantly reducing the water signal and producing CEST-MRI contrast enhancement (i.e. $k_{sw}$ is ideally suited to CEST-MRI).

FIG. 6 (Panel A and B), as discussed above, show Z-spectra acquired at 37° C., pH 7.4, and 40 mM concentrations, for an molecules 2f and 4f, respectively, corresponding to a reaction according to FIG. 5 in which $R=CH_3$.

The first CEST agent that conditionally produces signal only after binding rapidly to aldehydes under physiological conditions is described herein (see for example FIG. 5 and FIG. 6, Panels A and B).

Methods & Results

Synthetic Procedures

Intermediates and final products described in this study have been prepared in moderate to good yields, often times using modified literature protocols. Brief descriptions of synthetic schemes and experimental details associated with the compounds discussed within this Example are provided herein.

Figure 26:
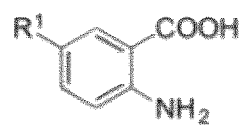
FIG. 26 illustrates the chemical structure of compounds discussed in Example 9.
Figure 26:
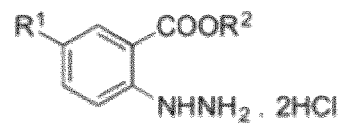
Figure 26:
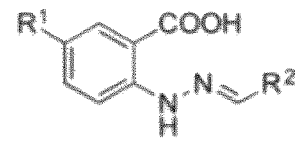
Figure 26:
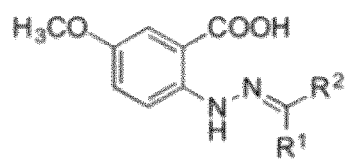
Figure 26:
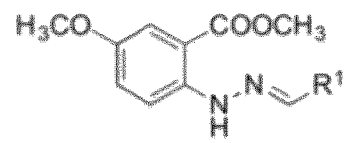
Figure 26:
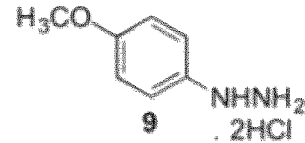
Figure 26:
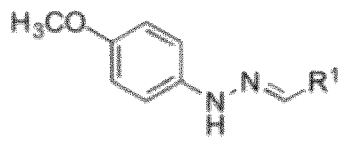
Figure 26:
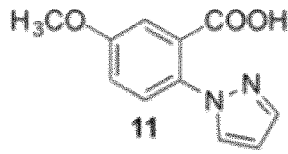
Figure 26:
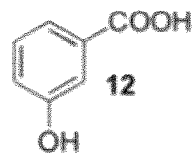

FIG. 26 illustrates the chemical structure of molecules discussed in this Example. Compounds marked with an asterisk (*) were not isolatable in this Example.

Anthranilic acids 1a-1f were diazotized (NaNO$_2$, HCl), followed by SnCl$_2$.2H$_2$O-mediated reduction. Corresponding hydrazines 2a-2f were obtained as dihydrochlorides. Treatment of 2a-2f with 2-formylbenzenesulfonic acid afforded hydrazones 3a-3f; when 2a-2f were treated with acetaldehyde, hydrazones 4a-4f were obtained. One notable exception is hydrazone 4d, which was not able to be isolated. To expand the library of compounds, hydrazone 2f was treated with aldehydes or corresponding synthetic equivalents (3-aminopropanal diethyl acetal, crotonaldehyde, racemic glyceraldehyde 18 and glycolaldehyde dimer) to furnish hydrazones 5a-5d. Reaction of 2f with acetone or pyruvic acid afforded hydrazones 6a and 6b.

To prepare the control compounds used in this study, 5-methoxyanthranilic acid (1f) was esterified (Fischer esterification), followed by a one pot diazotization-reduction cascade. Ester hydrazone 7 was obtained as a dihydrochloride salt. Treatment of 7 with 2-formylbenzenesulfonic acid furnished hydrazone 8a, while 8b was prepared by reaction of 7 with acetaldehyde. Reaction of commercially available 4-methoxyphenyl hydrazine dihydrochloride (MeOPH, 9) with 2-formylbenzenesulfonic acid led to the formation of hydrazone 10a; despite many attempts we were unable to isolate hydrazone 10b derived from 9 and acetaldehyde. Finally, when hydrazine 2f was treated with malondialdehyde tetramethyl acetal, pyrazole 11 was obtained. 3-Hydroxybenzoic acid 12 was commercially available.

Structural Requirements for CEST Signal

One limitation of diamagnetic CEST contrast agents is their often-small frequency offsets (~1-3 ppm) from water, making their signal deconvolution from the highly abundant water peak difficult. Anthranilic acids have previously been identified as CEST agents with a significant 4.8-9.3 ppm CEST signal frequency offset, a result of intramolecular hydrogen bonding between the benzylic amine and a hydrogen bonding partner in the ortho-position. The effect of converting weakly nucleophilic aromatic amine of anthranilic acid into an α-nucleophilic hydrazine was explored, with the intention of producing an aldehyde-specific imaging agent. Interestingly, the formation of the hydrazine nucleophile completely abolished proton exchange detectable by CEST methods (e.g. 2f), but this signal was recovered upon conversion of the probe to a hydrazone (e.g. 4f); only the hydrazone, but not the hydrazine, provided CEST contrast (FIG. 5, and FIG. 6, Panels A and B).

To denote the set of probes behaving in a similar manner, the term Hydrazo-CEST is utilized herein. Probe chemistries that produce imaging signal only once bound to their intended molecular target of interest (i.e. activatable) benefit from an inherent decrease of background signal, maximizing the achievable signal-to-noise ratio and signal specificity. In addition, the 'turn-on' mechanism of aldehyde reporting utilized by Hydrazo-CEST is independent of the anchorage of target aldehydes, and would be capable of mapping freely diffusing small molecule aldehydes as well as those derived from oxidized residues of biomacromolecules. The Hydrazo-CEST probes presented here thus take advantage of activation by specific targets of interest, and are an initiating class of non-optical, activatable imaging agents capable of selectively sensing endogenous reactive aldehydes.

Figure 27:
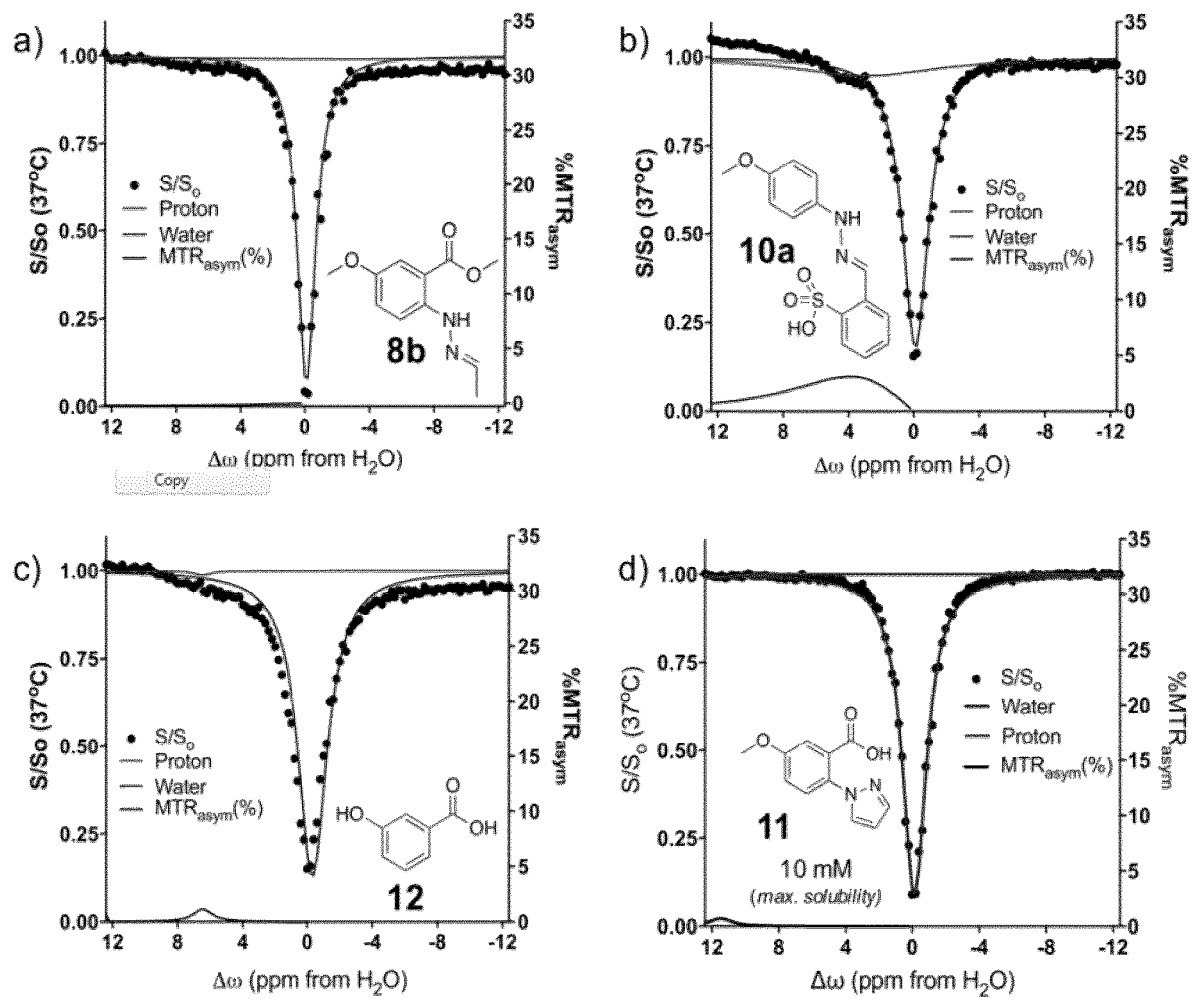
FIG. 27 provides Z-spectra of compounds 8b, 10a, 12, and 11 for Panels A to D, respectively, demonstrating the requirements of both the hydrazone and o-carboxylic acid for production of contrast for CEST-MRI.

FIG. 27 provides Z-spectra of compounds 8b, 10a, 12, and 11 for Panels A to D, respectively. These spectra demonstrating the requirements of both the hydrazone and o-carboxylic acid for the production of contrast for CEST-MRI. The masking of the o-carboxylic acid as the methyl ester (Panel A) or its complete absence (Panel B) significantly impairs CEST-MRI signal generation. Likewise the absence of the hydrazine moiety nearly completely abolishes signal production (Panel C). The absence of the hydrazone proton through the formation of a pyrazole also completely abolishes CEST-MRI signal (Panel D). Raw data points (S/S$_o$ are shown as black circles), exchangeable proton and water Lorentzian curves, and CEST-MRI signal production MTR$_{asym}$ (%), are also shown. All Z-spectra are obtained at 37° C. and pH 7.4 with 40 mM compound solutions in 10:1 PBS:D$_2$O unless otherwise indicated. These data are similar to data shown in FIG. 6, discussed above.

Hydrazo-CEST probes maintain a large 6.4 ppm frequency offset, and exhibit the same requirements for a hydrogen bonding partner in the ortho-position as demonstrated for anthranilic acids. The loss of the carboxylic acid proton through esterification results in a complete loss of the CEST effect (8b, see FIG. 27, Panel A), and the complete removal of the carboxylic acid to form a substituted phenyl hydrazine (10a, see FIG. 27, Panel B) results in significant broadening and weakening of the CEST signal, and an approximate 2 ppm upfield shift.

The importance of this intramolecular hydrogen bond is supported through molecular modelling of aliphatic and aryl aldehyde-derived hydrazones. E/Z isomerization around the hydrazone bond is known, which alters the relative position of the proton on the ring-proximal nitrogen, the putative exchangeable proton producing the Hydrazo-CEST signal. Density functional theory calculations using a B3LYP force field in water as solvent revealed that the E-isomers of both the aliphatic acetaldehyde- and aryl 2-formylbenzenesulfonic acid-derived hydrazones adopted conformations optimally positioning the ring-proximal nitrogen for intramolecular hydrogen bonding with the neighboring carboxylic acid group. The calculated geometry of the aliphatic aldehyde-derived hydrazone is that of a planar pseudo-six membered ring, with the putative exchangeable proton bonding directly with the carboxyl oxygen. The aryl aldehyde-derived hydrazone formed a more strained pseudo-six membered ring, with the ring-proximal nitrogen hydrogen bonding to the carboxyl proton.

$^1$H-NMR spectra of the acetaldehyde-derived hydrazone (4f) show both E- and Z-isomers, with E predominating 2:1 over the Z-isomer, and the cis on formation of the hydrazone bond predominating 2:1 over the trans conformation. Only the E-isomer is observed in the $^1$H-NMR of the 2-formylbenzenesulfonic acid-derived hydrazone (3f), which is in agreement with the molecular modelling, utilized herein, that was unable to minimize the energy associated with the Z-isomer for this structure.

The characterization of the structural requirements for Hydrazo-CEST continued by the removal of the α-nucleophile but retention of the carboxylic acid, which nearly completely abolished Hydrazo-CEST signal production (see FIG. 27, Panel C). It was sought, herein, to confirm that the proton on the ring-proximal nitrogen was actually the proton exchanging with water to induce the Hydrazo-CEST effect. Complete abolishment of signal production was observed with pyrazole 11 possessing no exchangeable proton on the ring proximal nitrogen (see FIG. 27, Panel D), supporting the hypothesis that indeed the proton on the ring-proximal nitrogen is the exchangeable proton giving rise to Hydrazo-CEST. Therefore, both computational and experimental data highlight the importance of the conformation of the hydrazone bond to position the exchangeable hydrogen, which is indeed that on the ring-proximal nitrogen, for hydrogen bonding with the necessary carboxylic acid group in the ortho position.

Kinetics of Hydrazone Formation and Stability Studies

In order to take advantage of the enhanced signal-to-noise ratio provided by the aldehyde-dependent activation of Hydrazo-CEST, the formation of the hydrazone from N-amino anthranilic acid must occur in situ under physiological conditions. The rates of reaction of carbonyls with hydrazine-derived nucleophiles have previously been characterized. It was found that intramolecular acid/base catalysis significantly enhanced the rate of hydrazone formation, with the reaction of butanal and 2-hydrazinobenzoic acid (2a) having a pseudo-first-order rate constant ($k_{obs}$) of 1.5±0.2 $min^{-1}$ in a 1:10 DMF:PBS solution.

FIG. 13, discussed above, illustrates that the o-carboxylic acid contributes to substantial reaction completion as well as extended stability of the product hydrazone under physiological conditions. Pane A shows kinetic plots for the reaction of N-amino anthranilic acid (2f), MeOPH or the methyl ester of 2f (compound 7) with 2-formylbenzenesulfonic acid, demonstrating that the carboxylic acid moiety is necessary for driving the reaction to completion, and to maintain the stability of the hydrazone product. Panel B shows high-pressure liquid chromatography traces of the reaction of 2f and MeOPH with 2-formylbenzenesulfonic acid. The hydrazone peak is shown (r.t.=17.5 min for 2f and 17.2 min for MeOPH) at the time points indicated. All reactions were performed in 1×PBS at 37° C., and points represent mean±s.d. for n=3 trials.

Repeating the methodology, however at 37° C. in 100% 1×PBS, determined the $k_{obs}$ for the reaction of 5-methoxy N-amino anthranilic acid (2f) and related analogs with 2-formylbenzenesulfonic acid (FIG. 13) and acetone.

Under the conditions employed, the $k_{obs}$ for hydrazone formation from 2f with 2-formylbenzenesulfonic acid was an order of magnitude greater than with acetone. This difference in reaction rate was previously observed among carbonyl compounds, with hydrazone formation from aldehydes proceeding faster than from ketones. Likewise, the $k_{obs}$ for hydrazone formation from 2-formylbenzenesulfonic acid and 7, a methyl ester analog of 2f, was reduced by three orders of magnitude, which was previously observed and attributed to the increased bulk of the methyl ester relative to the carboxylic acid. Importantly, substantial differences were observed in the extent of reaction completion and product stability, in addition to rate of reaction, between hydrazine structures for a given aldehyde, as well as between carbonyl types for a given hydrazine.

Hydrazone stability was assayed both spectrophotometrically (FIG. 13, Panel A), as well as by HPLC (FIG. 13, Panel B). While the formation of hydrazone from 2f and 2-formylbenzenesulfonic acid reached ~90% completion within 30 min of initiation, the absence of the intramolecular acid/base catalyst, as in the reaction of 4-methoxyphenyl hydrazine (9) or 7 with the same aryl aldehyde, substantially reduced reaction completion (<25% maximum), and reduced stability of the hydrazone product (FIG. 13, Panel B). These data illustrate a role for the ortho-carboxylic acid in product stabilization, in addition to the catalytic effect previously observed. A similar difference in reaction completion was observed for the reaction of 2f with acetone, resulting in <25% product formation (data not shown). Under the buffer and temperature conditions studied (i.e. 37° C. and 1×PBS), the rate of the reaction, the extent of reaction completion, and the stability of the hydrazone product were all substantially improved in the presence of the ortho-carboxylic acid.

Since the signal produced by Hydrazo-CEST depends on the hydrazone form of the probe, the faster-forming and longer-lived the hydrazone product under physiological conditions, the better the imaging signal evolved and the more potentially sensitive the imaging technique.

Electronic Requirements for CEST Signal

After demonstrating the structural requirement of the ortho-carboxylic acid moiety for Hydrazo-CEST signal production and the rapid, stable, and aldehyde-preferential formation of hydrazone under physiological conditions, the electronic contributions to Hydrazo-CEST were evaluated. Electron donating (OH, $OCH_3$) and electron-withdrawing (I, $SO_3$, $NO_2$) substituents were appended at the 5-position of N-amino anthranilic acid (compounds 2b-2f), both acetaldehyde (4b-4f) or 2-formylbenzenesulfonic acid-derived hydrazones (3b-3f) were prepared, and Z-spectra were acquired in 1:10 $D_2O$:PBS at pH 7.4 on a 300 MHz NMR.

Hydrazo-CEST signal production (% $MTR_{asym}$) was normalized to hydrazone concentration, as different hydrazone species showed different maximum solubility in neutral buffer. In this way, per molar signal output could be compared across hydrazone series to examine electronic contributions to Hydrazo-CEST.

FIG. 7, as described above, shows that the substitution of both the hydrazine and carbonyl substantially impact the CEST-MRI signal generation from Hydrazo-CEST contrast agents. The concentration-normalized Hydrazo-CEST signal (% $MTR_{asym}$/mM) is plotted for hydrazones formed by different substituents at the 5-position of the aryl hydrazine moiety, and with aliphatic (4) or aromatic (3) aldehydes. Signal production can be directly compared to salicylate, a known diamagnetic CEST agent. Sulfo-substituted hydrazine did not form a hydrazone with acetaldehyde. Values shown on the plot are $k_{sw}$ in Hz.

Importantly, Hydrazo-CEST as a contrast mechanism produced as much signal as the aspirin metabolite salicylate (FIG. 7), a diamagnetic CEST agent recently shown to have very high signal production. Ring deactivating substituents at the 5-position on the N-amino anthranilic acid substantially reduced Hydrazo-CEST signal relative to the unsubstituted parent compound regardless of the aldehyde derivative. For the acetaldehyde-derived hydrazones 4a-4f, a decrease in Hydrazo-CEST signal relative to the unsubstituted parent hydrazone was observed with an increasing strength of ring activation. However, the 2-formylbenzenesulfonic acid-derived hydrazones 3a-3f showed the opposite effect: an increase in Hydrazo-CEST signal production with an increase in ring activation potential. In efforts to explain these trends in signal production, the rate of exchange between bulk water and the proton on the ring-proximal nitrogen, $k_{sw}$, was measured by varying the saturation pulse power, and the values are shown in FIG. 7.

Indeed, the change in % $MTR_{asym}$ induced by altering the electronics through the 5-position of the hydrazine ring paralleled the change in $k_{sw}$. The importance of the contribution of the aryl hydrazine electronics to signal generation is supported by the linear free energy relationship between the chemical shift of the exchangeable hydrazone proton and the normalized proton exchange rates ($R^2$=0.990). Additionally, the aldehyde binding partner contributes to $k_{sw}$ of the proton on the ring-proximal nitrogen, likely via the π-conjugation maintained through the hydrazone bond. The o-sulfo substituent of the aryl aldehyde is more electron-withdrawing than the aliphatic carbon of the acetaldehyde, reducing electron density around the hydrazone bond, which could theoretically support a reduction in $k_{sw}$ and Hydrazo-CEST signal (e.g. 3f versus 4f). Therefore, the electronic contributions of both the aldehyde and hydrazine binding partners affect per molar normalized imaging signal by modulating the exchange rate of the proton on the ring-proximal nitrogen with water.

Concentration- and pH-Dependence of Hydrazo-CEST Signal

The MRI contrast produced by CEST probes is dependent upon voxel-wise concentration, however previous investigations have reported non-linear concentration relationships for CEST contrast agents. In order to evaluate this dependence for Hydrazo-CEST compounds, Z-spectra were acquired for acetaldehyde (4b-4f) and 2-formylbenzenesulfonic acid-derived hydrazones (3b-3f) on a 300 MHz NMR from 5 mM to 40 mM, or the maximum solubility of the compound in neutral buffer. The dynamic range for Hydrazo-CEST signal production from each compound was then plotted using the maximum signal for each compound (6.4±0.4 ppm). Within the series of acetaldehyde-derived hydrazones, the 5-methoxy- (4f) and 5-hydroxy-substituted (4e) analogs had the broadest dynamic range for imaging signal, with the 5-methoxy-derivative showing the higher absolute % $MTR_{asym}$ and the most linear concentration-dependent signal production ($R^2$=0.98). While the signal production at 20 mM was highest for the unsubstituted hydrazone (4a) relative to 4e and 4f, its low sensitivity to changes in concentration below 10 mM and limited solubility beyond 20 mM substantially narrowed its dynamic range. For the series of 2-formylbenzenesulfonicacid-derived hydrazones, the 5-hydroxy-substituted (3e) analog displayed the best dynamic range with the most linear concentration-dependent signal production ($R^2$=0.98) of all of the analogs examined.

In fact, both the unsubstituted (3a) and 5-methoxy-substituted (3f) analogs displayed non-linear concentration dependence over the range of concentrations examined. Importantly, the signal production from 4f at 5 mM ($MTR_{asym}$=9%) has been shown to be suitable for detection in vivo by CEST-MRI, and is on par on a per molar basis with salicylate, a diamagnetic CEST-MRI contrast agent readily detectable in vivo.

In addition to local probe concentrations, micro-environmental pH can modify CEST signal production, as pH directly impacts $k_{sw}$. The effect of pH on % $MTR_{asym}$ was evaluated for the unsubstituted, 5-hydroxy-, and 5-methoxy-substituted hydrazones derived from acetaldehyde (4a, 4e, 4f) and 2-formylbenzenesulfonic acid (3a, 3e, 3f). The aliphatic aldehyde-derived hydrazones displayed a broad pH range (approx. pH 6 to 8) over which high CEST signal production was observed, with maximum signal occurring between pH 6.5 and 7.5. The 5-methoxy-substituted probe (4f) produced significantly higher CEST signal at all pH values tested. Note that 4f was not soluble at 40 mM at pH 6.5, however both 4a and 4e were completely soluble from pH 6.0-8.0. In contrast, the % $MTR_{asym}$ from aromatic aldehyde-derived hydrazones was substantially reduced above pH 6.5-7.0, with maximum signal generation occurring below pH 6.5. The hydroxy- and methoxy-substituted aryl-hydrazones (3e, 3f) gave better CEST signal production from pH 6.5-8.0, but both were insoluble at 40 mM at pH 6.0. The differential pH responses associated with the Hydrazo-CEST probes studied are justified by the higher predicted electron density around the ring-proximal nitrogen of the aliphatic versus aromatic hydrazones, which would favor the protonated form of the hydrazo moiety at higher pH values. Since the majority of endogenously formed aldehydes are non-aromatic, the 5-methoxy-substituted analog (2f) was selected as the lead compound for endogenous aldehyde detection with Hydrazo-CEST due to its superior dynamic range with aliphatic aldehydes and enhanced signal generation at neutral pH.

Detection of Endogenous Carbonyls

Having optimized the Hydrazo-CEST probe chemistry for high signal production in physiological conditions, signal generation from endogenous carbonyls was explored.

Figure 28:
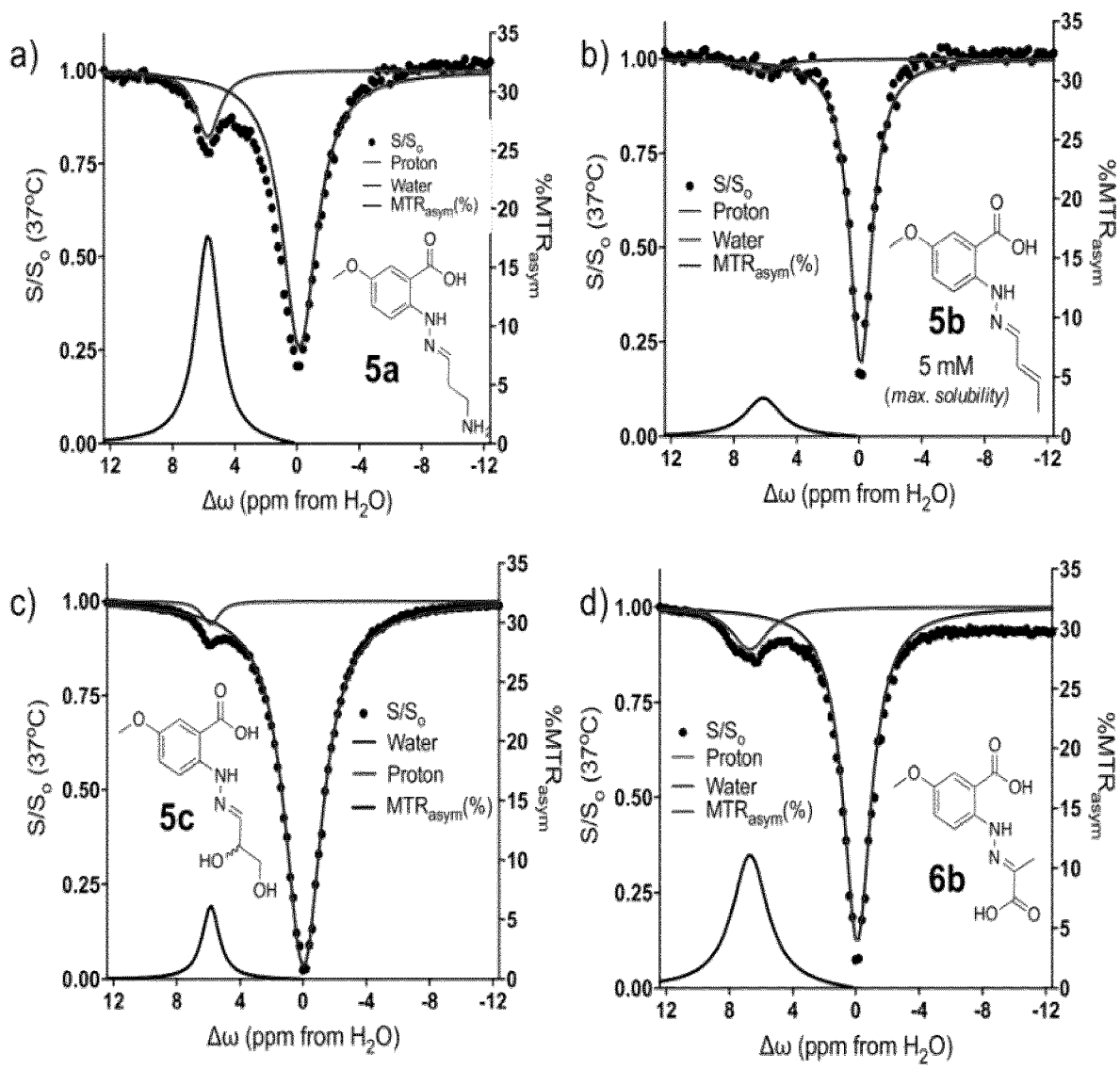
FIG. 28 shows Hydrazo-CEST signal production from endogenous carbonyls. Hydrazones were formed between a hydrazine (20 and (Panel A) 3-aminopropanal, (Panel B) crotonaldehyde, (Panel C) glyceraldehyde, and (Panel D) pyruvate.

FIG. 28 shows Hydrazo-CEST signal production from endogenous carbonyls. Z-spectra were acquired on a 300 MHz NMR in 10:1 PBS:$D_2O$ at 37° C., pH 7.4, at 40 mM, or the indicated concentration providing maximum solubility. Hydrazones were formed between 2f and (Panel A) 3-aminopropanal, (Panel B) crotonaldehyde, (Panel C) glyceraldehyde, and (Panel D) pyruvate.

Z-spectra were generated for a variety of hydrazones formed from 2f and endogenous aldehydes and ketones: 5a is the hydrazone of 3-aminopropanal, a product of polyamine catabolism suggested to be elevated following traumatic brain injury (FIG. 28, Panel A); 5b is the hydrazone product of crotonaldehyde, a terminal product of lipid peroxide catabolism following cell stress (FIG. 28, Panel B); 5c is the hydrazone formed from glyceraldehyde, the glycolytic intermediate required for phospholipid biogenesis (FIG. 28, Panel C); 6b is the hydrazone product of 2f and pyruvate, a key biochemical intermediate for a variety of biosynthetic and metabolic pathways including anaerobic glycolysis (FIG. 28, Panel D). Importantly, there was no hydrazone formation between 2f and D-glucose under physiological conditions (37° C., 1 PBS, pH=7.4) within 4 h of incubation, illustrating that glucose did not interfere with aldehyde sensing by Hydrazo-CEST.

Previous work imaging lung fibrosis-associated aldehydes demonstrated that, using gadolinium-based MRI contrast agents, pathologically-derived aldehydes could be effectively detected in live animals. CEST contrast agents have an inherent mechanism of signal amplification not available to gadolinium chelates, which derives from the >500 proton exchanges per second with water molecules (FIG. 13) and the 3-5 s saturation pulse applied. For each molecule of activated Hydrazo-CEST contrast agent, 1500-2500 molecules of water will bear a spin-saturated proton. As pathologically-relevant levels of aldehydes, for example 3-aminopropanal in the cerebrospinal fluid of humans following head trauma, have been measured at 0.1-0.3 mM, the signal amplification inherent to CEST-MRI should allow these aldehydes to be readily detectable by Hydrazo-CEST. Given the substantial signal production (approx. 20% $MTR_{asym}$) by the 3-aminopropanal-derived hydrazone (5a), the limited signal production by metabolic aldehyde (glyceraldehyde, 5c), and the limited hydrazone formation rates between 2f and ketones, such as pyruvate (6b), this supports the value of Hydrazo-CEST as a first-in-class, aldehyde-activated MRI contrast agent for mapping these endogenous markers of tissue stress.

Hydrazo-CEST MRI

As further support of this novel class of contrast agent for aldehyde-activated imaging, the performance of Hydrazo-CEST was validated in a 3 T and 7 T MRI.

Figure 29:
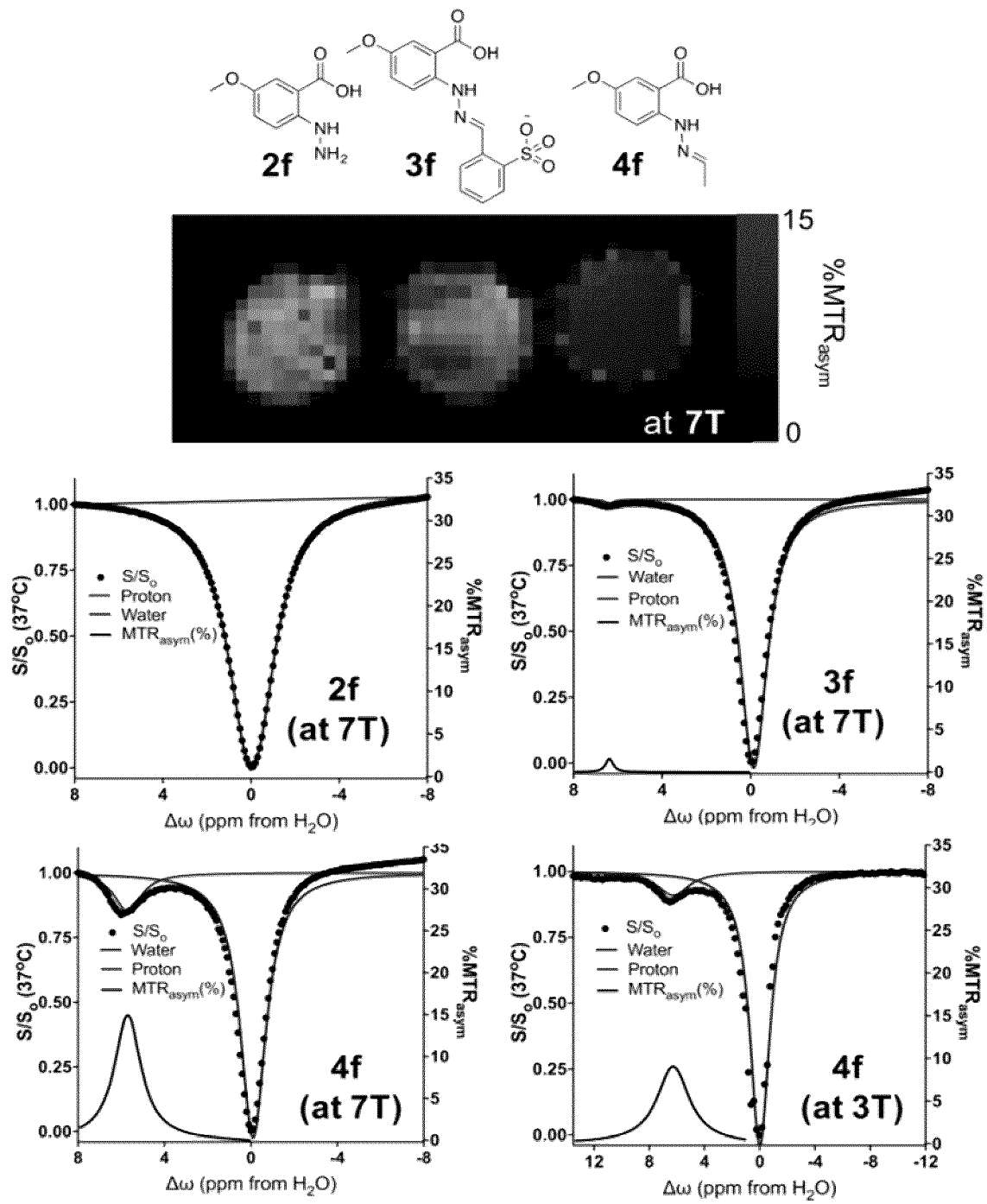
FIG. 29 shows a phantom image and Z-spectra of hydrazine (2f) and hydrazones (30 and (4f) according to Example 9.

FIG. 29 shows that Hydrazo-CEST probes provide high contrast and rapidly form hydrazones in situ. In the upper panel, a Phantom image and Z-spectra of hydrazine 2f and hydrazones 3f and 4f were acquired at the indicated field strength, 37° C., pH 7.4, and 40 mM concentration.

Figure 30:
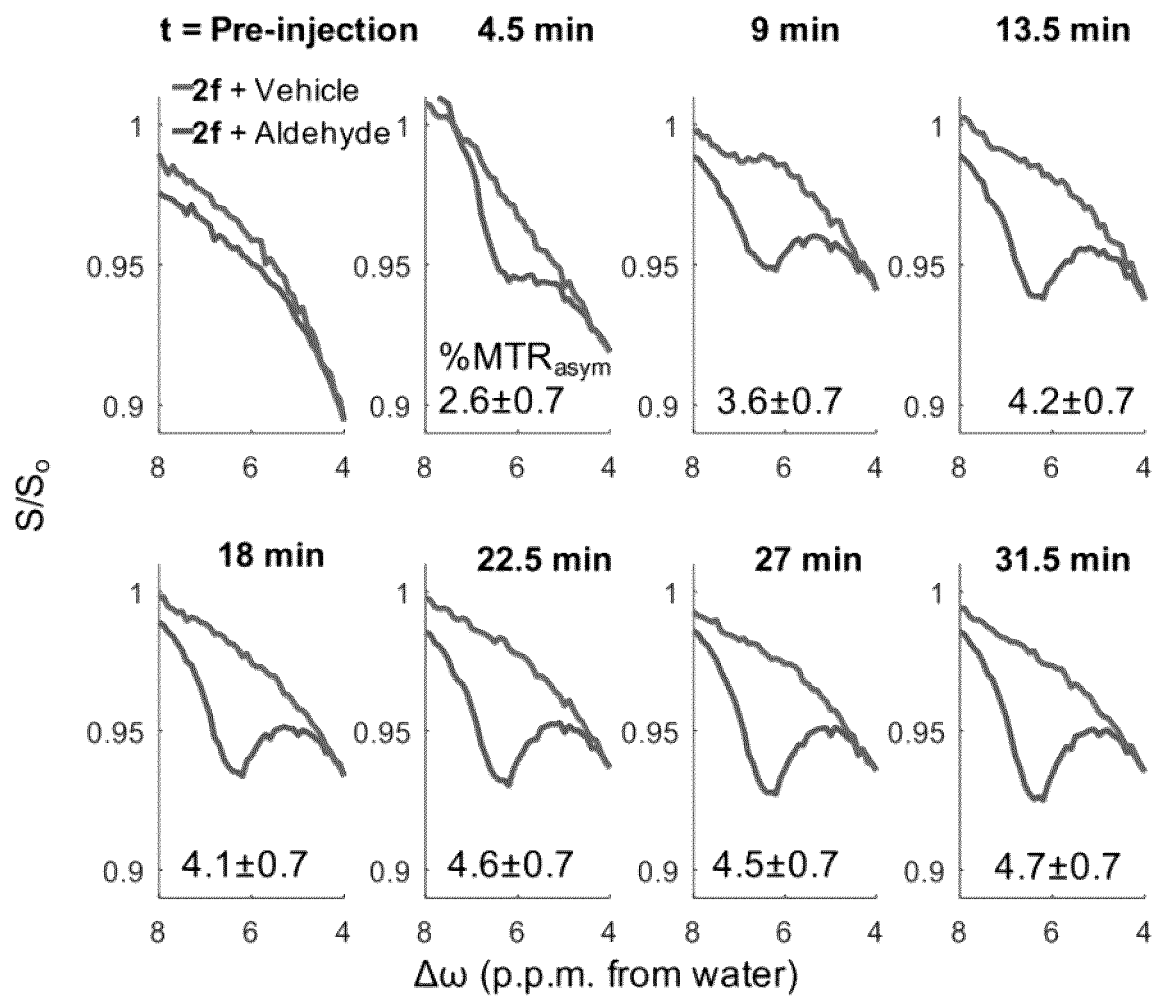
FIG. 30 shows Z-spectra acquired following the addition of vehicle or 2-FB to a 40 mM solution of hydrazine 2f at 37° C. and pH 7.4 at different times.

FIG. 30 shows Z-spectra acquired following the addition of vehicle or 2-FB to a 40 mM solution of hydrazine 2f at 37° C. and pH 7.4. Values indicate the % $MTR_{asym}$±the standard deviation of the off-resonance measurements once the system had reached steady state.

Just as observed in the NMR, the hydrazine form of the probe (2f) produced no CEST contrast (FIG. 29, left), however signal production was substantially increased following hydrazone formation from either aliphatic (4f) or aromatic aldehydes (3f) with a frequency offset from water of 6.4 ppm. The kinetics of Hydrazo-CEST signal production through hydrazone formation were also evaluated in the MRI at 37° C. in 1×PBS at pH=7.4 (FIG. 28). Either PBS or a PBS solution of 2-formylbenzenesulfonic acid at a final concentration of 20 mM was injected into the imaging phantom, and Z-spectra were acquired every 4.5 min to monitor hydrazone formation.

A single saturation peak at 6.4 ppm was observed 4.5 min after aldehyde injection. The Hydrazo-CEST signal increased rapidly, surpassing 50% maximal signal within the first 4.5 min, and reaching a maximum plateau (% $MTR_{asym}$ 4.6±0.7) by 18 to 22.5 minutes after aldehyde addition. This MRI data confirms that Hydrazo-CEST probes are rapidly activated by aldehydes under physiological conditions, and are readily detectable by 7 T MRI. Both hydrazine and hydrazone functionalities are utilized in medications broadly spanning indications from anti-infectives and anti-parasitics, to anti-cancer agents. This data, taken together with preliminary in vitro toxicity assays demonstrating the initial safety of 2f, suggest a viable potential of Hydrazo-CEST for the mapping of endogenous aldehydes in living subjects.

CONCLUSIONS

In conclusion, a new class of CEST-MRI contrast agents is described, derived from N-amino anthranilic acids. These agents are termed Hydrazo-CEST, herein. These agents conditionally respond to the presence of aldehydes upon in situ transformation from hydrazine to hydrazone. The 'turn-on' mechanism of aldehyde reporting utilized by Hydrazo-CEST is independent of the anchorage of target aldehydes, and would be capable of mapping freely diffusing small molecule aldehydes as well as those derived from oxidized residues of bio-macromolecules. The importance of the carboxylic acid ortho to the α-nucleophile was investigated, demonstrating its requirement for signal production, as well as for rapid hydrazone formation and extended product stability under physiological conditions. Additionally, the electronic requirements providing optimal CEST contrast have been identified, with electron-donating substituents at the 5-position (i.e. hydroxy and methoxy) providing superior performance in terms of signal generation over the ranges of concentrations and pH expected in living subjects. The rapid reaction with aldehydes and high CEST MRI signal production at 3 T and 7 T support the use of these probes for the detection and mapping of endogenous aldehydes in living subjects. With Hydrazo-CEST, small molecule, endogenous aldehyde biomarkers of disease are accessible to mapping, allowing chemical biological investigations of these important biomolecules.

In the preceding description, for purposes of explanation, numerous details are set forth in order to provide a thorough understanding of the embodiments. However, it will be apparent to one skilled in the art that these specific details are not required. Specific details are not provided as to whether the embodiments of imaging or diagnostic products described herein are implemented as a software routine, hardware circuit, firmware, or a combination thereof.

Embodiments described herein can be represented as or may involve a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

US Patent Publication No. 2016/0082133 A1
US Patent Publication No. 2014/0294772 A1
Kool et al., Fast Hydrazone Reactants: Electronic and Acid/Base Effects Strongly Influence Rate at Biological pH. *J. Am. Chem. Soc.*, 2013, 135 (47), pp 17663-6.
Wood et al., Neurotoxicity of reactive aldehydes. *Brain Res.* 1095(2006) 190-9.
Wu et al., An overview of CEST MRI for non-MR physicists. *EJNMMI Phys.* 2016 December; 3(1):19. Published online Aug. 26, 2016. doi: 10.1186/s40658-016-0155-2.

The invention claimed is:

1. A method of detecting a freely diffusing small molecule aldehyde in a subject comprising administering an aldehyde-binding compound of Formula I to the subject and detecting the product of the compound of Formula I and the freely diffusing small molecule aldehyde using magnetic resonance imaging (MRI), CEST-MRI or positron emission tomography (PET) imaging;

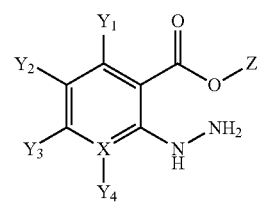

Formula I wherein:
X is C or N;
Z is H, alkyl, cycloalkyl, or aryl;
$Y_1$ and $Y_3$ are H;
$Y_2$ is $CHs^3$—O—; and Y4 is independently:
  H;
  a substituent selected from the group consisting of Br, Cl, I, nitro, sulfo, carboxy, hydroxyl, alkoxy, cycloalkoxy, aryloxy, C1-6 alkyl, aryl, cycloalkyl, alkyne, propargyl, and tetrazine;
  wherein detection of said freely diffusing small molecule aldehyde is indicative of a brain injury or of cell death optionally wherein the aldehyde-binding compound additionally comprises a radio-label for use in positron emission tomography imaging.

2. The method according to claim 1, wherein Z is H or CH₃.

3. The method according to claim 1, wherein the aldehyde-binding compound comprises any one of:

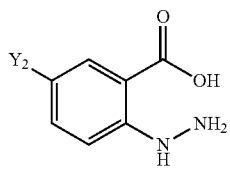

Formula I-A

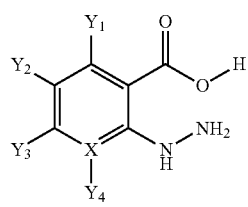

Formula I-B wherein X, Z, and Y₁, Y₂, Y₃ and Y₄ are as defined in claim 1.

4. The method of claim 1, wherein the freely diffusing small molecule aldehyde is glycolic acid, acetone, H₂N—CH—CH—CO—H, malondialdehyde, crotonaldehyde, pyruvate, glyoxal, glyceraldehyde, DL-glyceraldehyde, glycoaldehyde, acetaldehyde, o-sulfobenzaldehyde, a secosterol, or 3-aminopropanal.

5. The method according to claim 1, wherein the brain injury comprises a concussion, traumatic brain injury, or anoxic brain injury.

6. The method according to claim 1, wherein the cell death is from chemotherapeutic killing of a tumour cell.

7. The method according to claim 1, wherein the product detected comprises one of the following compounds:

301-Z

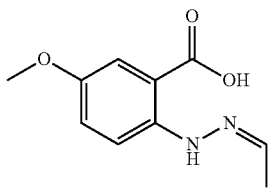

301-E

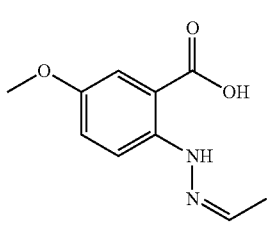

-continued

302

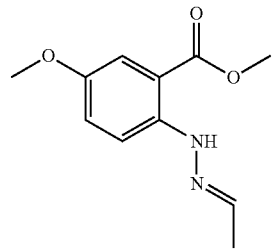

308-Z

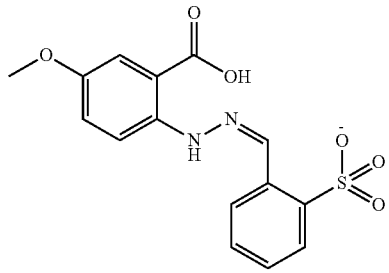

308-E

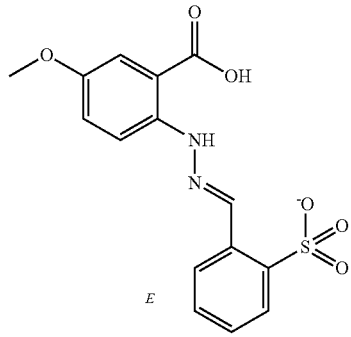

313

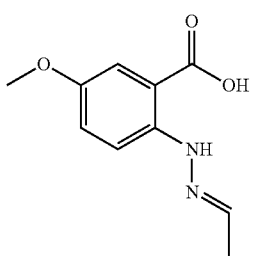

314

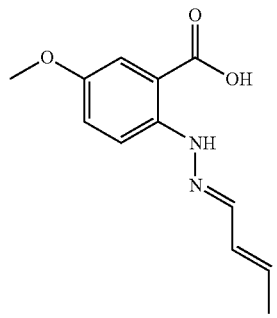

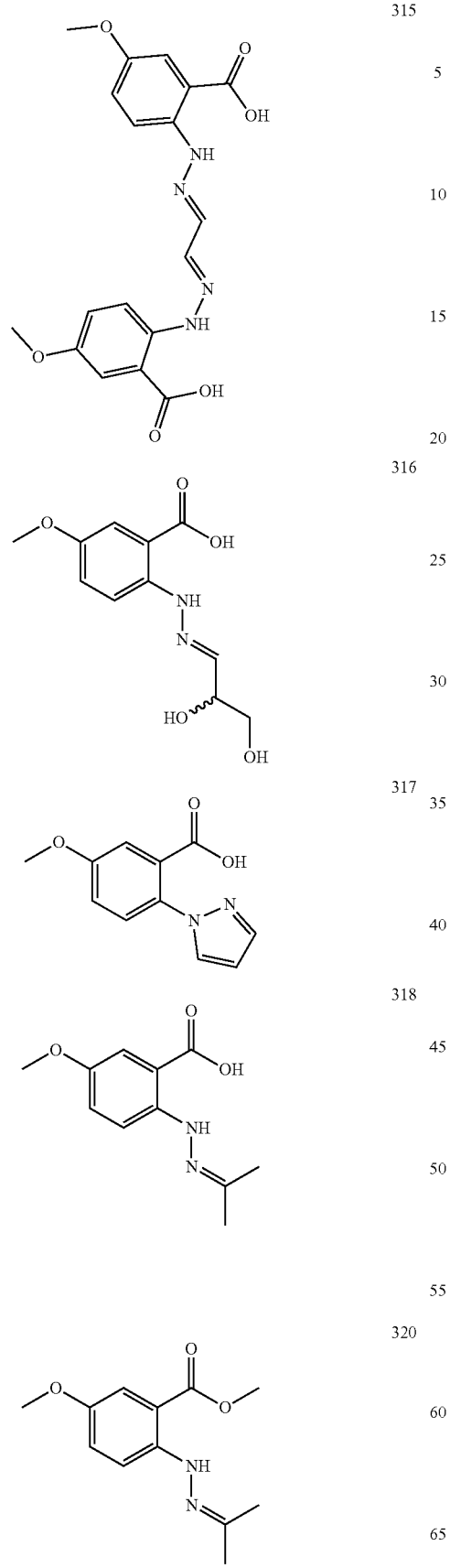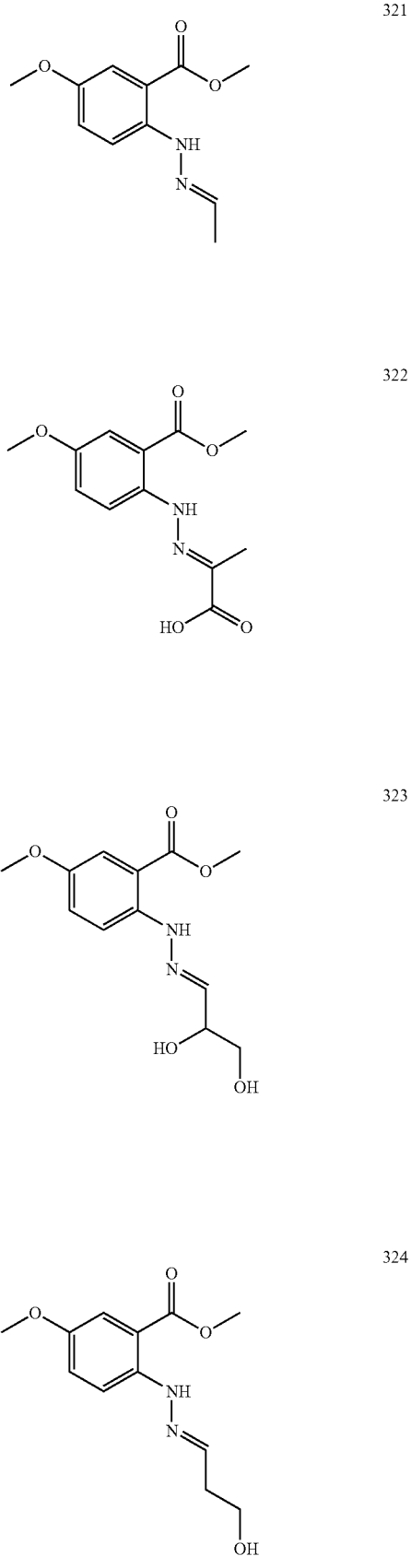

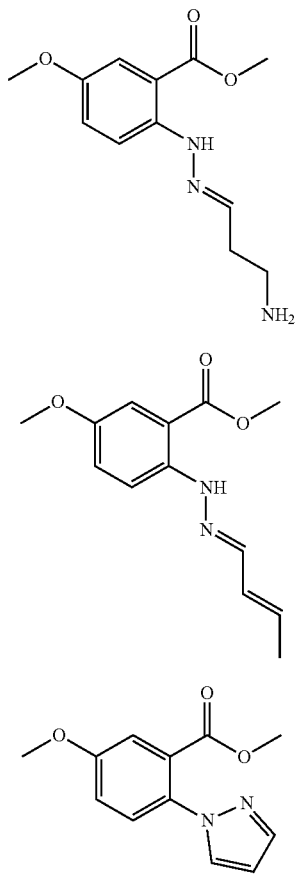

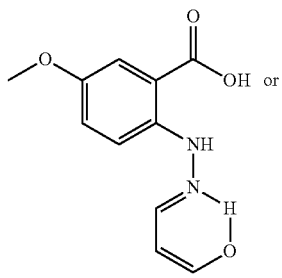

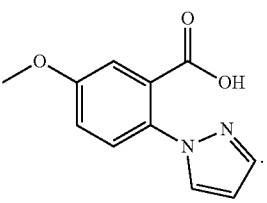

8. The method of claim 1, wherein the freely diffusing small molecule aldehyde is endogenous.

9. The method of claim 1, wherein the freely diffusing small molecule aldehyde has a molecular weight (MVV) of less than 100.

10. The method of claim 1, wherein the freely diffusing small molecule aldehyde to be detected is unbound to protein.

11. The method of claim 1, wherein the cell death is death of a cancer cell.

* * * * *